United States Patent
Filla et al.

[11] Patent Number: 5,874,427
[45] Date of Patent: Feb. 23, 1999

[54] SUBSTITUTED HETEROAROMATIC 5-HT$_{1F}$ AGONISTS

[75] Inventors: Sandra A. Filla, Franklin; Joseph H. Krushinski, Jr., Indianapolis; John Mehnert Schaus, Zionsville, all of Ind.

[73] Assignee: Eli Lilly and Company, Indianapolis, Ind.

[21] Appl. No.: 59,768

[22] Filed: Apr. 14, 1998

Related U.S. Application Data

[60] Provisional application No. 60/043,624 Apr. 14, 1997.

[51] Int. Cl.$^6$ .......... A61K 31/55; A61K 31/435; C07D 471/04
[52] U.S. Cl. .......... 514/214; 514/299; 514/300; 514/305; 540/593; 546/112; 546/113; 546/138
[58] Field of Search .......... 546/112, 113, 546/138; 514/299, 300, 305, 214; 540/593

[56] References Cited

U.S. PATENT DOCUMENTS

| | | | |
|---|---|---|---|
| 5,051,412 | 9/1991 | Macor | 514/300 |
| 5,169,947 | 12/1992 | Macor | 548/113 |
| 5,521,196 | 5/1996 | Audia et al. | 514/323 |
| 5,521,197 | 5/1996 | Audia | 514/323 |
| 5,604,240 | 2/1997 | Chambers et al. | 514/300 |
| 5,708,008 | 1/1998 | Audia et al. | 514/323 |

FOREIGN PATENT DOCUMENTS

| | | |
|---|---|---|
| 0379314 | 7/1990 | European Pat. Off. . |
| 2295615 | 6/1996 | United Kingdom . |
| WO 96/29075 | 9/1996 | WIPO . |

*Primary Examiner*—Bernard Dentz
*Attorney, Agent, or Firm*—Robert D. Titus; David E. Boone

[57] ABSTRACT

This invention provides novel 5-HT$_{1F}$ agonists of the Formula

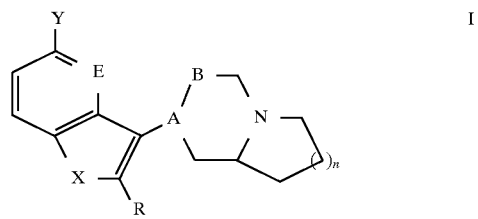

in which X, Y, E, R, A, B, and n are as defined in the specification, which are useful for the treatment of migraine and associated disorders.

9 Claims, No Drawings

SUBSTITUTED HETEROAROMATIC 5-HT$_{1F}$ AGONISTS

PRIORITY CLAIM

This application claims the benefit of U.S. Provisional Patent Application Ser. No. 60/043,624 filed Apr. 14, 1997.

BACKGROUND OF THE INVENTION

Theories regarding the pathophysiology of migraine have been dominated since 1938 by the work of Graham and Wolff (*Arch. Neurol. Psychiatry*, 39, 737–63 (1938)). They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. (Humphrey, et al., *Ann. NY Acad. Sci.*, 600, 587–600 (1990)). Recent work by Moskowitz has shown, however, that the occurrence of migraine headaches is independent of changes in vessel diameter (*Cephalalgia*, 12, 5–7, (1992)).

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)).

Serotonin (5-HT) exhibits diverse physiological activity mediated by at least four receptor classes, the most heterogeneous of which appears to be 5-HT$_1$. A human gene which expresses a fifth 5-HT$_1$ subtype, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention provides novel 5-HT$_{1F}$ agonists which inhibit peptide extravasation due to stimulation of the trigeminal ganglia, and are therefore useful for the treatment of migraine and associated disorders.

SUMMARY OF THE INVENTION

The present invention provides novel substituted indoles, pyrrolo[3,2-b]pyridines, benzofurans, and benzothiophenes of Formula I:

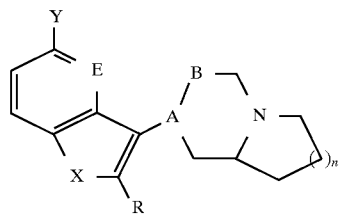

I in which

A—B is —CH—CH$_2$— or —C=CH—;

n is 1, 2, or 3;

R is hydrogen or C$_1$–C$_4$ alkyl;

X is N—H, O, or S;

Y is hydrogen, hydroxy, amino, halo, —S—R$^1$, —C(O)R$^2$, —C(O)NR$^3$R$^4$, —NR$^5$SO$_2$R$^6$, —NHC(Q)NR$^7$R$^8$, —NHC(O)OR$^9$, or —NR$^5$C(O)R$^{10}$;

wherein:

Q is O or S;

R$^1$ is phenyl, substituted phenyl, phenyl(C$_1$–C$_4$ alkylene), phenyl(C$_1$–C$_4$ alkylene) substituted in the phenyl ring, or pyridinyl;

R$^2$ is C$_1$–C$_6$ alkyl, phenyl(C$_1$–C$_4$ alkylene), phenyl (C$_1$–C$_4$ alkylene) substituted in the phenyl ring, naphthyl, amino, N-methyl-N-methoxyamino, heteroaryl, substituted heteroaryl, heteroaryl(C$_1$–C$_4$ alkyl), or substituted heteroaryl(C$_1$–C$_4$ alkyl);

R$^3$ is hydrogen, C$_1$–C$_6$ alkyl, heteroaryl, substituted heteroaryl, heteroaryl(C$_1$–C$_4$ alkyl), or substituted heteroaryl(C$_1$–C$_4$ alkyl);

R$^4$ is hydrogen or C$_1$–C$_6$ alkyl; or

R$^3$ and R$^4$ taken together with the nitrogen atom, to which they are attached, form a pyrrolidine, piperidine, substituted piperidine, piperazine, 4-substituted piperazine, morpholine or thiomorpholine ring;

R$^5$ is hydrogen or C$_1$–C$_4$ alkyl;

R$^6$ is C$_1$–C$_4$ alkyl, phenyl, substituted phenyl, or di(C$_1$–C$_4$ alkyl)amino;

R$^7$ and R$^8$ are independently selected from the group consisting of C$_1$–C$_6$ alkyl, C$_3$–C$_6$ alkenyl, C$_3$–C$_8$ cycloalkyl, phenyl, substituted phenyl, phenyl(C$_1$–C$_4$ alkylene), phenyl(C$_1$–C$_4$ alkylene) substituted in the phenyl ring, ((C$_1$–C$_4$ alkyl or C$_1$–C$_4$ alkoxycarbonyl substituted)C$_1$–C$_4$ alkyl)phenyl, C$_1$–C$_4$ alkyl a-substituted with C$_1$–C$_4$ alkoxycarbonyl; or R$^7$ and R$^8$ taken together with the nitrogen atom form a pyrrolidine, piperidine, piperazine, 4-substituted piperazine, morpholine or thiomorpholine ring;

R$^9$ is C$_1$–C$_6$ alkyl, C$_3$–C$_6$ alkenyl, phenyl, substituted phenyl, C$_3$–C$_8$ cycloalkyl, C$_1$–C$_4$ alkyl w-substituted with C$_1$–C$_4$ alkoxy;

R$^{10}$ is C$_1$–C$_{10}$ alkyl optionally substituted with up to three substituents selected from the group consisting of hydroxy, C$_1$–C$_4$ alkoxy, halo, aryloxy, C$_1$–C$_4$ alkoxycarbonyl and heteroaryloxy, C$_2$–C$_{10}$ alkenyl, C$_2$–C$_{10}$ alkynyl, C$_3$–C$_8$ cycloalkyl, phenyl, substituted phenyl, naphthyl, phenyl(C$_1$–C$_4$ alkylene), phenyl(C$_1$–C$_4$ alkylene) substituted on the phenyl ring, 2-phenylethylen-1-yl, diphenylmethyl, benzofused C$_4$–C$_8$ cycloalkyl, C$_1$–C$_4$ alkylene w-substituted with C$_3$–C$_6$ cycloalkyl, or a heterocycle;

E is —CH— or N provided that E may not be N when X is O or S; and pharmaceutically acceptable acid addition salts and solvates thereof.

This invention also provides a pharmaceutical formulation which comprises, in association with a pharmaceutically acceptable carrier, diluent or excipient, a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, dysphoric disorder, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of Formula I.

The use of a compound of Formula I for the activation of the 5-HT$_{1F}$ receptor, for the inhibition of peptide extravasation in general or due to stimulation of the trigeminal ganglia specifically, and for the treatment of any of the disorders described supra, are all embodiments of the present invention.

DETAILED DESCRIPTION OF THE INVENTION

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pentyl-, 3-pentyl-, neopentyl, hexyl, heptyl, octyl and the like. The term "alkoxy" includes such groups as methoxy, ethoxy, n-propoxy, isopropoxy, n-butoxy, isobutoxy, sec-butoxy, tert-butoxy, pentoxy, 2-pentoxy-, 3-pentoxy-, neopentoxy, hexoxy, heptoxy, octoxy and the like. The term alkylthio includes such groups as methylthio, ethylthio, n-propylthio, isopropylthio, n-butylthio, isobutylthio, sec-butylthio, tert-butylthio, pentylthio, 2-pentylthio, 3-pentylthio, neopentylthio, hexylthio, heptylthio, octylthio and the like. The term "alkenyl" includes vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like. The term "alkynyl" includes acetylenyl, propynyl, 2-butyn-4-yl, 1-butyn-4-yl, 1-pentyn-5-yl, 2-pentyn-5-yl and the like. The term "acyl" includes, for example, formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "phenyl($C_1$–$C_4$ alkylene)" includes such groups as benzyl, phenethyl, phenpropyl and phenbutyl. The term "($C_1$–$C_4$ alkyl)sulfonyl" includes methanesulfonyl, ethanesulfonyl propanesulfonyl, isopropanesulfonyl, butanesulfonyl and the like. The term "halo" includes fluoro, chloro, bromo and iodo.

The term "substituted phenyl" or "phenyl($C_1$–$C_4$ alkylene) substituted in the phenyl ring" is taken to mean the phenyl moiety may be substituted with one substituent selected from the group consisting of halo, $C_1$–$C_4$ alkyl, $C_1$–$C_8$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sulfonyl, or two to three substituents independently selected from the group consisting of halo, nitro, $C_1$–$C_4$ alkyl, or $C_1$–$C_4$ alkoxy.

The term "heterocycle" is taken to mean stable aromatic and non-aromatic 5- and 6-membered rings containing from 1 to 3 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2. Non-aromatic rings include, for example, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl and the like. Aromatic rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused aromatic rings include isoquinolinyl, benzoxazolyl, benzthiazolyl, quinolinyl, benzofuranyl, thionaphthyl, indolyl and the like.

The term "heteroaryl" is taken to mean an aromatic or benzofused aromatic heterocycle as defined in the previous paragraph. The term "substituted heteroaryl" is taken to mean an aromatic or benzofused aromatic heterocycle as defined in the previous paragraph substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2. The term "heteroaryl($C_1$–$C_4$ alkyl)" is taken to mean a branched or linear alkyl chain of 1 to 4 carbon atoms substituted at some point with an aromatic or benzofused aromatic heterocycle moiety. The term "substituted heteroaryl($C_1$–$C_4$ alkyl)" is taken to mean a branched or linear alkyl chain of 1 to 4 carbon atoms substituted at some point with an aromatic or benzofused aromatic heterocycle moiety which is substituted with up to three substituents independently selected from the group consisting of halo, $C_1$–$C_4$ alkoxy, $C_1$–$C_4$ alkyl, cyano, nitro, hydroxy, —S(O)$_m$—($C_1$–$C_4$ alkyl) and —S(O)$_m$-phenyl where m is 0, 1 or 2.

The term "heteroaryloxy" is taken to mean a heteroaryl or substituted heteroaryl group, as defined in the previous paragraph, bonded to an oxygen atom.

The term "aryloxy" is taken to mean a phenyl or substituted phenyl group bonded to an oxygen atom.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl($C_1$–$C_4$ alkylene) substituted in the phenyl ring, heteroaryl, and heteroaryl ($C_1$–$C_4$ alkylene).

The term "substituted piperidine" is taken to mean a piperidine ring optionally substituted with a substituent selected from the group consisting of hydroxy, hydroxymethyl, and N,N-di($C_1$–$C_4$ alkyl)carboxamido.

The term "benzofused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

All of the compounds of the invention contain a chiral center located in the moiety attached at the 3 position of the compounds of the invention. This chiral center specifically is located at the bridgehead carbon in the indolizinyl, quinolizinyl, or 1-azabicyclo[5.4.0]undecanyl ring system. Such centers are designated "R" or "S" in accord with accepted norms of nomenclature. For the purposes of the present application, the numbering system for naming the substituents around the indole, pyrrolo[3,2-b]pyridine, benzofuran, and benzothiophene rings, as well as the R and S enantiomers of the invention are illustrated below, where A, B, n, R, X, Y, and Z are as defined supra.

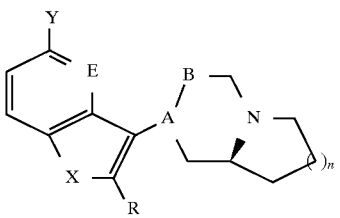

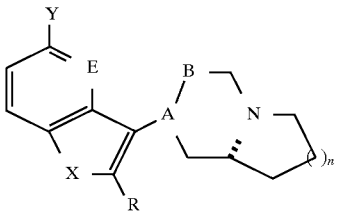

Both enantiomers, and mixtures thereof, are included within the scope of the present invention. While either single enantiomer and all mixtures thereof are useful 5-HT$_{1F}$ agonists, single enantiomers are preferred.

The skilled artisan will appreciate that those compounds of the invention where A—B is —CH—CH$_2$— contain a second symmetric carbon where the indole, pyrrolo[3,2-b]indole, benzofuran, or benzothiophene nucleus attaches to the indolizinyl, quinolizinyl, or 1-azabicyclo[5.4.0]undecanyl ring systems. This second asymmetric center gives rise to the following diastereomeric pairs, where n, R, X, Y, and Z are as defined supra.

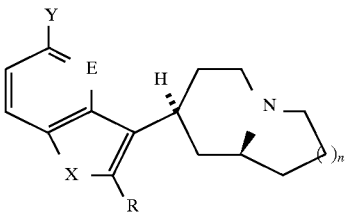

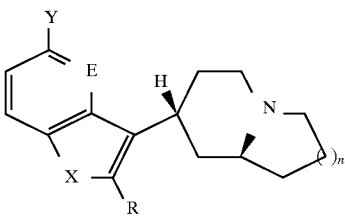

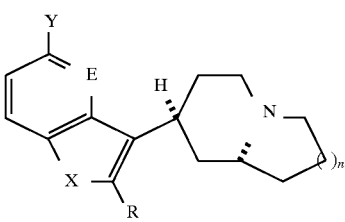

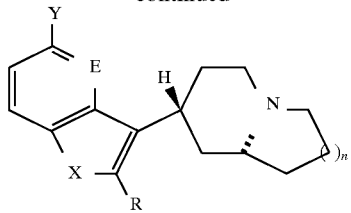

All diastereomers, and mixtures thereof, are included within the scope of the present invention. While any single diastereomer and all mixtures thereof are useful 5-HT$_{1F}$ agonists, single diasteromers are preferred.

While all of the compounds of this invention are useful as 5-HT$_{1F}$ agonists, certain classes are preferred. The following paragraphs describe such preferred classes.

aa) A—B is —C=CH—;
ab) A—B is —CH—CH$_2$—;
ac) R is methyl;
ad) R is hydrogen;
ae) n is 1;
af) n is 2;
ag) X is N—H;
ah) X is O;
ai) X is S;
aj) Y is hydrogen;
ak) Y is halo;
al) Y is amino;
am) Y is hydroxyl;
an) Y is —S—R$^1$;
ao) Y is —C(O)R$^2$;
ap) Y is —C(O)NR$^3$R$^4$;
aq) Y is —NR$^5$SO$_2$R$^6$;
ar) Y is —NHC(Q)NR$^7$R$^8$;
as) Y is —NHC(O)OR$^9$;
at) Y is —NR$^5$C(O)R$^{10}$;
au) Q is O;
av) R$^1$ is phenyl monosubstituted with halo;
aw) R$^1$ is 4-chlorophenyl;
ax) R$^1$ is phenyl(C$_1$–C$_4$ alkylene);
ay) R$^1$ is benzyl;
az) R$^1$ is pyridinyl;
ba) R$^1$ is 2-pyridinyl;
bb) R$^2$ is C$_1$–C$_4$ alkyl;
bc) R$^2$ is methyl;
bd) R$^2$ is butyl;
be) R$^2$ is phenyl(C$_1$–C$_4$ alkylene);
bf) R$^2$ is benzyl;
bg) R$^2$ is phenyl;
bh) R$^2$ is heteroaryl;
bi) R$^3$ is heteroaryl or substituted heteroaryl;
bj) R$^3$ is heteroaryl(C$_1$–C$_4$ alkyl) or substituted heteroaryl (C$_1$–C$_4$ alkyl);
bk) R$^4$ is hydrogen;
bl) R$^4$ is C$_1$–C$_4$ alkyl;
bm) R$^4$ is C$_1$–C$_6$ alkyl;
bn) R$^4$ is methyl;
bo) R$^4$ is butyl;

bp) $R^4$ is isopropyl;
bq) $R^3$ and $R^4$ taken together with the nitrogen atom form a pyrrolidine ring;
br) $R^3$ and $R^4$ taken together with the nitrogen atom form a piperidine ring;
bs) $R^3$ and $R^4$ taken together with the nitrogen atom form a substituted piperidine ring;
bt) $R^3$ and $R^4$ taken together with the nitrogen atom form a piperazine ring;
bu) $R^3$ and $R^4$ taken together with the nitrogen atom form a 4-substituted piperazine ring;
bv) $R^3$ and $R^4$ taken together with the nitrogen atom form a morpholine ring;
bw) $R^3$ and $R^4$ taken together with the nitrogen atom form a thiomorpholine ring;
bx) $R^5$ is $C_1$–$C_4$ alkyl;
by) $R^5$ is methyl;
bz) $R^5$ is hydrogen;
ca) $R^6$ is $C_1$–$C_4$ alkyl;
cb) $R^6$ is methyl;
cc) $R^6$ is ethyl;
cd) $R^6$ is phenyl;
ce) $R^6$ is di($C_1$–$C_4$ alkyl)amino;
cf) $R^6$ is dimethylamino;
cg) $R^7$ is hydrogen;
ch) $R^8$ is $C_1$–$C_4$ alkyl;
ci) $R^8$ is methyl;
cj) $R^8$ is ethyl;
ck) $R^8$ is propyl;
cl) $R^8$ is isopropyl;
cm) $R^8$ is phenyl;
cn) $R^8$ is $C_3$–$C_8$ alkenyl;
co) $R^8$ is allyl;
cp) $R^8$ is phenyl monosubstituted with halo;
cq) $R^8$ is 4-fluorophenyl;
cr) $R^8$ is 4-chlorophenyl;
cs) $R^8$ is phenyl($C_1$–$C_4$ alkylene)
ct) $R^8$ is benzyl;
cu) $R^8$ is phenethyl;
cv) $R^7$ and $R^8$ taken together with nitrogen form a morpholine ring;
cw) $R^7$ and $R^8$ taken together with nitrogen form a thiomorpholine ring;
cw) $R^7$ and $R^8$ taken together with nitrogen form a pyrrolidine ring;
cy) $R^7$ and $R^8$ taken together with nitrogen form a piperidine ring;
cz) $R^7$ and $R^8$ taken together with nitrogen form a pyrrolidine ring;
da) $R^7$ and $R^8$ taken together with nitrogen form a piperazine ring;
db) $R^7$ and $R^8$ taken together with nitrogen form a 4-substituted piperazine ring;
dc) $R^9$ is $C_1$–$C_4$ alkyl;
dd) $R^9$ is methyl;
de) $R^9$ is ethyl;
df) $R^9$ is propyl;
dg) $R^9$ is $C_3$–$C_6$ alkenyl;
dh) $R^9$ is allyl;
di) $R^9$ is $C_3$–$C_8$ cycloalkyl;
dj) $R^9$ is cyclopentyl;
dk) $R^9$ is phenyl monosubstituted with $C_1$–$C_4$ alkoxy;
dl) $R^9$ is 4-methoxyphenyl;
dm) $R^{10}$ is $C_3$–$C_6$ alkenyl;
dn) $R^{10}$ is allyl;
do) $R^{10}$ is $C_3$–$C_6$ cycloalkyl;
dp) $R^{10}$ is cyclopropyl;
dq) $R^{10}$ is cyclobutyl;
dr) $R^{10}$ is phenyl($C_1$–$C_4$ alkylene);
ds) $R^{10}$ is $C_1$–$C_4$ alkyl w-substituted with phenoxy;
dt) $R^{10}$ is $C_1$–$C_4$ alkyl w-substituted with $C_1$–$C_4$ alkoxy;
du) $R^{10}$ is methoxymethyl;
dv) $R^{10}$ is ethoxymethyl;
dw) $R^{10}$ is phenyl;
dx) $R^{10}$ is 2-phenylethylen-1-yl;
dy) $R^{10}$ is phenyl monosubstituted with halo;
dz) $R^{10}$ is phenyl monosubstituted with chloro;
ea) $R^{10}$ is phenyl monosubstituted with fluoro;
eb) $R^{10}$ is 4-fluorophenyl;
ec) $R^{10}$ is 2-chlorophenyl;
ed) $R^{10}$ is phenyl monosubstituted with $C_1$–$C_4$ alkoxy;
ee) $R^{10}$ is phenyl monosubstituted with methoxy;
ef) $R^{10}$ is 4-methoxyphenyl;
eg) $R^{10}$ is phenyl monosubstituted with $C_1$–$C_4$ alkyl;
eh) $R^{10}$ is phenyl monosubstituted with methyl;
ei) $R^{10}$ is phenyl monosubstituted with trifluoromethyl, $C_1$–$C_4$ alkylthio, cyano, nitro, phenyl, $C_1$–$C_4$ acyl or benzoyl;
ej) $R^{10}$ is 4-cyanophenyl;
ek) $R^{10}$ is 4-nitrophenyl;
el) $R^{10}$ is 4-phenylphenyl;
em) $R^{10}$ is phenyl disubstituted with substitutents selected from halo, $C_1$–$C_4$ alkyl, $C_1$–$C_4$ alkoxy and nitro;
en) $R^{10}$ is phenyl disubstituted with halo;
eo) $R^{10}$ is 2,4-dichlorophenyl;
ep) $R^{10}$ is a heterocycle;
eq) $R^{10}$ is furyl optionally substituted with $C_1$–$C_4$ alkyl, $C_1$–$C_4$ alkoxy, or halo;
er) $R^{10}$ is 2-furyl;
es) $R^{10}$ is 3-furyl;
et) $R^{10}$ is thienyl optionally substituted with halo, $C_1$–$C_4$ alkyl or $C_1$–$C_4$ alkoxy;
eu) $R^{10}$ is 2-thienyl;
ev) $R^{10}$ is 3-thienyl;
ew) $R^{10}$ is 3-methyl-2-thienyl;
ex) $R^{10}$ is 5-methyl-2-thienyl;
ey) $R^{10}$ is pyridinyl optionally substituted with halo, $C_1$–$C_4$ alkyl or $C_1$–$C_4$ alkoxy;
ez) $R^{10}$ is 3-pyridinyl;
fa) $R^{10}$ is 4-pyridinyl;
fb) $R^{10}$ is 6-halo-3-pyridinyl;
fc) $R^{10}$ is pyrazinyl;
fd) $R^{10}$ is isoxazolyl;
fe) $R^{10}$ is 2-benzofuranyl;
ff) The compound is a free base;
fg) The compound is a salt;

fh) The compound is the hydrochloride salt;
fi) The compound is the fumarate salt;
fj) The compound is the oxalate salt;
fk) The compound is a racemate;
fl) The compound is the R-enantiomer;
fm) The compound is the S-enantiomer;
fn) X is N—H and E is —CH—;
fo) X is N—H and E is N.

It will be understood that the above classes may be combined to form additional preferred classes.

The compounds of this invention are useful in a method for increasing activation of the 5-HT$_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, b-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, oxalic acid or fumaric acid.

The following group is illustrative of compounds contemplated within the scope of this invention:

5-amino-3-(1,2,3,4,5,8-hexahydroindolizin-7-yl)-1H-indole
5-amino-3-(octahydroindolizin-7-yl)-1H-indole
5-amino-3-(1,2,3,4,5,8-hexahydroindolizin-7-yl)-benzofuran
5-amino-3-(octahydroindolizin-7-yl)-benzofuran
5-amino-3-(1,2,3,4,5,8-hexahydroindolizin-7-yl)-benzothiophene
5-amino-3-(octahydroindolizin-7-yl)-benzothiophene
5-(4-fluorophenyl)thio-3-(1,2,3,4,5,8-hexahydroindolizin-7-yl)-1H-indole
5-(3-chlorophenyl)thio-3-(1,4,5,6,7,8,9-heptahydroquinolizin-2-yl)-2-methyl-benzofuran
5-(2-bromophenyl)thio-3-(1-azabicyclo[5.4.0]undec-3-en-4-yl)-benzothiophene
5-(2-iodophenyl)thio-3-(1,2,3,4,5,8-hexahydroindolizin-7-yl)-1H-indole
5-(3-methoxyphenyl)thio-3-(1,4,5,6,7,8,9-heptahydroquinolizin-2-yl)-benzofuran
5-(4-iodophenyl)thio-3-(1-azabicyclo[5.4.0]undec-3-en-4-yl)-benzothiophene
5-(2-ethoxyphenyl)thio-3-(1,2,3,4,5,8-hexahydroindolizin-7-yl)-1H-indole
5-(4-ethoxyphenyl)thio-3-(1,4,5,6,7,8,9-heptahydroquinolizin-2-yl)-benzofuran
5-(3-propoxyphenyl)thio-3-(1-azabicyclo[5.4.0]undec-3-en-4-yl)-benzothiophene hydrochloride
5-(2-isopropoxyphenyl)thio-3-(1,2,3,4,5,8-hexahydroindolizin-7-yl)-1H-indole
5-(4-isopropoxyphenyl)thio-3-(1,4,5,6,7,8,9-heptahydroquinolizin-2-yl)-benzofuran hydrobromide
5-(3-butoxyphenyl)thio-3-(1-azabicyclo[5.4.0]undec-3-en-4-yl)-benzothiophene hydroiodide
5-(2-isobutoxyphenyl)thio-3-(1,2,3,4,5,8-hexahydroindolizin-7-yl)-1H-indole
5-(4-isobutoxyphenyl)thio-3-(1,4,5,6,7,8,9-heptahydroquinolizin-2-yl)-benzofuran acetate
5-(3-sec-butoxyphenyl)thio-3-(l-azabicyclo[5.4.0]undec-3-en-4-yl)-benzothiophene
5-(2-tert-butoxyphenyl)thio-3-(1,2,3,4,5,8-hexahydroindolizin-7-yl)-1H-indole propionate
5-(4-tert-butoxyphenyl)thio-3-(1,4,5,6,7,8,9-heptahydroquinolizin-2-yl)-benzofuran
5-(2-pyridinyl)thio-3-(1-azabicyclo[5.4.0]undec-3-en-4-yl)-benzothiophene decanoate
5-(4-pyridinyl)thio-3-(1,2,3,4,5,8-hexahydroindolizin-7-yl)-1H-indole
5-(2-phenethyl)thio-3-(1,4,5,6,7,8,9-heptahydroquinolizin-2-yl)-benzofuran caprylate
5-(4-phenbutyl)thio-3-(1-azabicyclo[5.4.0]undec-3-en-4-yl)-benzothiophene
5-(2-chlorophenyl)thio-3-(octahydroindolizin-7-yl)-1H-indole acrylate
5-(4-bromophenyl)thio-3-(octahydro-2H-quinolizin-2-yl)-benzofuran
5-(2-bromophenyl)thio-3-(1-azabicyclo[5.4.0]undecan-4-yl)-benzothiophene formate
5-(3-iodophenyl)thio-3-(octahydroindolizin-7-yl)-1H-indole
5-(2-methoxyphenyl)thio-3-(octahydro-2H-quinolizin-2-yl)-benzofuran isobutyrate
5-(4-methoxyphenyl)thio-3-(1-azabicyclo[5.4.0]undecan-4-yl)-benzothiophene
5-(3-ethoxyphenyl)thio-3-(octahydroindolizin-7-yl)-2-methyl-1H-indole caproate
5-(2-propoxyphenyl)thio-3-(octahydro-2H-quinolizin-2-yl)-benzofuran
5-(4-propoxyphenyl)thio-3-(1-azabicyclo[5.4.0]undecan-4-yl)-benzothiophene heptanoate
5-(3-isopropoxyphenyl)thio-3-(octahydroindolizin-7-yl)-1H-indole
5-(2-butoxyphenyl)thio-3-(octahydro-2H-quinolizin-2-yl)-benzofuran propiolate
5-(4-butoxyphenyl)thio-3-(1-azabicyclo[5.4.0]undecan-4-yl)-benzothiophene
5-(2-sec-butoxyphenyl)thio-3-(octahydroindolizin-7-yl)-1H-indole oxalate
5-(4-sec-butoxyphenyl)thio-3-(octahydro-2H-quinolizin-2-yl)-benzofuran
5-(2-tert-butoxyphenyl)thio-3-(1-azabicyclo[5.4.0]undecan-4-yl)-benzothiophene malonate
5-(3-pyridinyl)thio-3-(octahydroindolizin-7-yl)-1H-indole
5-benzylthio-3-(octahydro-2H-quinolizin-2-yl)-benzofuran succinate 5-(3-phenpropyl)thio-3-(1-azabicyclo[5.4.0]undecan-4-yl)-benzothiophene 5-propanoyl-3-(1,2,3,4,5,8-hexahydroindolizin-7-yl)-1H-indole suberate 5-(2-methylpropanoyl)-3-(1,4,5,6,7,8,9-heptahydroquinolizin-2-yl)-benzofuran 5-butanoyl-3-(1-azabicyclo[5.4.0]undec-3-en-4-yl)-benzothiophene sebacate 5-(sec-butanoyl)-3-(1,2,3,4,5,8-hexahydroindolizin-7-yl)-1H-indole 5-(2-methylbutanoyl)-3-(1,4,5,6,7,8,9-heptahydroquinolizin-2-yl)-2-methyl-benzofuran fumarate 5-(3,3-dimethylbutanoyl)-3-(1-azabicyclo[5.4.0]undec-3-en-4-yl)-benzothiophene 5-heptanoyl-3-(1,2,3,4,5,8-hexahydroindolizin-7-yl)-1H-indole butyne-1,4-dioate 5-(3-chlorobenzoyl)-3-(1,4,5,6,7,8,9-heptahydroquinolizin-2-yl)-benzofuran 5-(3-fluorobenzoyl)-3-(1-azabicyclo[5.4.0]undec-3-en-4-yl)-benzothiophene 5-(3-bromobenzoyl)-3-(1,2,3,4,5, 8-hexahydroindolizin-7-yl)-1H-indole hydrobromide 5-(2-bromobenzoyl)-3-(1,4,5,6,7,8,9-heptahydroquinolizin-2-yl)-benzofuran 5-(3-iodobenzoyl)-3-(1-azabicyclo[5.4.0]undec-3-en-4-yl)-benzothiophene 5-(3-methoxybenzoyl)-3-(1,2,3,4,5,8-hexahydroindolizin-7-yl)-1H-indole 5-(2-ethoxybenzoyl)-3-(1,4,5,6,7,8,9-heptahydroquinolizin-2-yl)-benzofuran 5-(4-ethoxybenzoyl)-3-(1-azabicyclo[5.4.0]undec-3-en-4-yl)-benzothiophene 5-(2-propoxybenzoyl)-3-(1,2,3,4,5,8-hexahydroindolizin-7-yl)-1H-indole hydrochloride 5-(3-propoxybenzoyl)-3-(1,4,5,6,7,8,9-heptahydroquinolizin-2-yl)-benzofuran 5-(3-butoxybenzoyl)-3-(1-azabicyclo[5.4.0]undec-3-en-4-yl)-benzothiophene 5-(2-methylbenzoyl)-3-(1,2,3,4,5,8-hexahydroindolizin-7-yl)- 1H-indole 5-(3-ethylbenzoyl)-3-(1,4,5,6,7,8,9-heptahydroquinolizin-2-yl)-benzofuran 5-(4-propylbenzoyl)-3-(1-azabicyclo[5.4.0]undec-3-en-4-yl)-benzothiophene 5-(2-propylbenzoyl)-3-(1,2,3,4,5,8-hexahydroindolizin-7-yl)-1H-indole 5-(3-butylbenzoyl)-3-(1,4,5,6,7,8,9-heptahydroquinolizin-2-yl)-benzofuran 5-(3-trifluoromethylbenzoyl)-3-(1-azabicyclo[5.4.0]undec-3-en-4-yl)-benzothiophene 5-(3-trifluoromethoxybenzoyl)-3-(1,2,3,4,5,8-hexahydroindolizin-7-yl)-1H-indole 5-(3-dimethylaminobenzoyl)-3-(1,4,5,6,7,8,9-heptahydroquinolizin-2-yl)-benzofuran 5-(3-phenylpropanoyl)-3-(1-azabicyclo[5.4.0]undec-3-en-4-yl)-benzothiophene 5-(5-phenylpentanoyl)-3-(1,2,3,4,5,8-hexahydroindolizin-7-yl)-1H-indole 5-(3-pyridinecarbonyl)-3-(1,4,5,6,7,8,9-heptahydroquinolizin-2-yl)-benzofuran 5-(3-phenylpropanoyl)-3-(1-azabicyclo[5.4.0]undec-3-en-4-yl)-benzothiophene 5-butanoyl-3-(octahydroindolizin-7-yl)-1H-indole 5-(3-methyl)butanoyl-3-(octahydro-2H-quinolizin-2-yl)-2-methyl-benzofuran 5-(2,2-dimethyl)propanoyl-3-(1-azabicyclo[5.4.0]undecan-4-yl)-benzothiophene fumarate 5-hexanoyl-3-(octahydroindolizin-7-yl)-1H-indole 5-(2-ethyl)butanoyl-3-(octahydro-2H-quinolizin-2-yl)-benzofuran 5-(2-chlorobenzoyl)-3-(1-azabicyclo[5.4.0]undecan-4-yl)-benzothiophene 5-(2-fluorobenzoyl)-3-(octahydroindolizin-7-yl)-1H-indole 5-(2-bromobenzoyl)-3-(octahydro-2H-quinolizin-2-yl)-benzofuran 5-(2-iodobenzoyl)-3-(1-azabicyclo[5.4.0]undecan-4-yl)-benzothiophene 5-(4-iodobenzoyl)-3-(octahydroindolizin-7-yl)-1H-indole 5-(2-methoxybenzoyl)-3-(octahydro-2H-quinolizin-2-yl)-benzofuran 5-(3-ethoxybenzoyl)-3-(1-azabicyclo[5.4.0]undecan-4-yl)-benzothiophene 5-(4-propoxybenzoyl)-3-(octahydroindolizin-7-yl)-1H-indole 5-(2-butoxybenzoyl)-3-(octahydro-2H-quinolizin-2-yl)-benzofuran hexyne-1,6-dioate 5-(4-butoxybenzoyl)-3-(1-azabicyclo[5.4.0]undecan-4-yl)-benzothiophene 5-(3-methylbenzoyl)-3-(octahydroindolizin-7-yl)-1H-indole 5-(4-ethylbenzoyl)-3-(octahydro-2H-quinolizin-2-yl)-benzofuran 5-(2-ethylbenzoyl)-3-(1-azabicyclo[5.4.0]undecan-4-yl)-benzothiophene benzoate 5-(3-propylbenzoyl)-3-(octahydroindolizin-7-yl)-1H-indole 5-(2-butylbenzoyl)-3-(octahydro-2H-quinolizin-2-yl)-benzofuran 5-(4-butylbenzoyl)-3-(1-azabicyclo[5.4.0]undecan-4-yl)-benzothiophene 5-(2-trifluoromethylbenzoyl)-3-(octahydroindolizin-7-yl)-1H-indole chlorobenzoate 5-(3-trifluoromethoxybenzoyl)-3-(octahydro-2H-quinolizin-2-yl)-benzofuran 5-(2-dimethylaminobenzoyl)-3-(1-azabicyclo[5.4.0]undecan-4-yl)-benzothiophene 5-(4-phenylbutanoyl)-3-(octahydroindolizin-7-yl)-1H-indole 4-methylbenzoate 5-(1-naphthoyl)-3-(octahydro-2H-quinolizin-2-yl)-benzofuran 5-(4-pyridinecarbonyl)-3-(1-azabicyclo[5.4.0]undecan-4-yl)-benzothiophene 5-(N-phenyl)carboxamido-3-(1,2,3,4,5,8-hexahydroindolizin-7-yl)-2-methyl-1H-indole 2,4-dinitrobenzoate 5-(N-benzyl)carboxamido-3-(1,4,5,6,7,8,9-heptahydroquinolizin-2-yl)-benzofuran 5-(N-(2-(4-chlorophenyl)ethyl))carboxamido-3-(1-azabicyclo[5.4.0]undec-3-en-4-yl)-benzothiophene 4-hydroxybenzoate 5-(N-(2-(3-methylphenyl)ethyl))carboxamido-3-(1,2,3,4,5,8-hexahydroindolizin-7-yl)-1H-indole 5-(N-(3-(2-methoxyphenyl)propyl))carboxamido-3-(1,4,5,6,7,8,9-heptahydroquinolizin-2-yl)-benzofuran 5-(N-(4-(4-trifluoromethylphenyl)butyl))carboxamido-3-(1-azabicyclo[5.4.0]undec-3-en-4-yl)-benzothiophene 3-methoxybenzoate 5-(N-(4-chlorophenyl))carboxamido-3-(octahydroindolizin-7-yl)-1H-indole 5-(N-benzyl)carboxamido-3-(octahydro-2H-quinolizin-2-yl)-benzofuran 5-(N-(2-phenethyl))carboxamido-3-(1-azabicyclo[5.4.0]undecan-4-yl)-2-methyl-benzothiophene 5-(N-(3-phenpropyl))carboxamido-3-(octahydroindolizin-7-yl)-1H-indole 5-(N-(3-phenpropyl))carboxamido-3-(octahydro-2H-quinolizin-2-yl)-benzofuran phthalate 5-(N-(4-phenbutyl))carboxamido-3-(1-azabicyclo[5.4.0]
undecan-4-yl)-benzothiophene
5-(N-methyl-N-ethanesulfonyl)amino-3-(1,2,3,4,5,8-
hexahydroindolizin-7-yl)-1H-indole
5-(N-ethyl-N-propanesulfonyl)amino-3-(1,4,5,6,7,8,9-
heptahydroquinolizin-2-yl)-benzofuran
5-(N-isopropanesulfonyl)amino-3-(1-azabicyclo[5.4.0]
undec-3-en-4-yl)-benzothiophene
5-(N-propyl-N-butanesulfonyl)amino-3-(1,2,3,4,5,8-
hexahydroindolizin-7-yl)-1H-indole
5-(N-isobutanesulfonyl)amino-3-(1,4,5,6,7,8,9-
heptahydroquinolizin-2-yl)-benzofuran methanesulfonate
5-(N-sec-butanesulfonyl)amino-3-(1-azabicyclo[5.4.0]
undec-3-en-4-yl)-benzothiophene
5-(N-tert-butanesulfonyl)amino-3-(1,2,3,4,5,8-
hexahydroindolizin-7-yl)-1H-indole
5-(N-butyl-N-benzenesulfonyl)amino-3-(1,4,5,6,7,8,9-
heptahydroquinolizin-2-yl)-benzofuran
5-(N,N-diethylaminosulfonyl)amino-3-(1-azabicyclo[5.4.0]
undec-3-en-4-yl)-2-methyl-benzothiophene
5-(N,N-dipropylaminosulfonyl)amino-3-(1,2,3,4,5,8-
hexahydroindolizin-7-yl)-1H-indole
5-(N,N-diisopropylaminosulfonyl)amino-3-(1,4,5,6,7,8,9-
heptahydroquinolizin-2-yl)-benzofuran
5-(N,N-dibutylaminosulfonyl)amino-3-(1-azabicyclo[5.4.0]
undec-3-en-4-yl)-benzothiophene
5-(N-ethanesulfonyl)amino-3-(octahydroindolizin-7-yl)-
1H-indole phenylsulfonate
5-(N-propanesulfonyl)amino-3-(octahydro-2H-quinolizin-
2-yl)-benzofuran
5-(N-isopropanesulfonyl)amino-3-(1-azabicyclo[5.4.0]
undecan-4-yl)-benzothiophene
5-(N-butanesulfonyl)amino-3-(octahydroindolizin-7-yl)-
1H-indole
5-(N-isobutanesulfonyl)amino-3-(octahydro-2H-quinolizin-
2-yl)-benzofuran
5-(N-isopropyl-N-sec-butanesulfonyl)amino-3-(1-
azabicyclo[5.4.0]undecan-4-yl)-benzothiophene
5-(N-(tert-butyl)sulfonyl)amino-3-(octahydroindolizin-7-
yl)-1H-indole
5-(N,N-diethylaminosulfonyl)amino-3-(octahydro-2H-
quinolizin-2-yl)-benzofuran
5-(N,N-dipropylaminosulfonyl)amino-3-(1-azabicyclo
[5.4.0]undecan-4-yl)-2-methyl-benzothiophene
5-(N,N-diisopropylaminosulfonyl)amino-3-
(octahydroindolizin-7-yl)-1H-indole
5-(N,N-dibutylaminosulfonyl)amino-3-(octahydro-2H-
quinolizin-2-yl)-benzofuran
N-ethyl-N'-(3-(1,2,3,4,5,8-hexahydroindolizin-7-yl)-1H-
indol-5-yl)thiourea
N-isopropyl-N'-(3-(1,4,5,6,7,8,9-heptahydroquinolizin-2-
yl)-1H-indol-5-yl)thiourea
N-(3-methoxy)phenyl-N'-(3-(1-azabicyclo[5.4.0]undec-3-
en-4-yl)-1H-indol-5-yl)thiourea
N-(2-ethoxy)phenyl-N'-(2-methyl-3-(1,2,3,4,5,8-
hexahydroindolizin-7-yl)-1H-indol-5-yl)thiourea
N-(2-ethoxy)phenyl-N'-(3-(1,4,5,6,7,8,9-
heptahydroquinolizin-2-yl)-1H-indol-5-yl)thiourea
N-(3-ethoxy)phenyl-N'-(3-(1-azabicyclo[5.4.0]undec-3-en-
4-yl)-1H-indol-5-yl)thiourea
N-(3-propoxy)phenyl-N'-(3-(1,2,3,4,5,8-
hexahydroindolizin-7-yl)-1H-indol-5-yl)thiourea
N-(3-isopropoxy)phenyl-N'-(3-(1,4,5,6,7,8,9-
heptahydroquinolizin-2-yl)-1H-indol-5-yl)thiourea
N-(4-isopropoxy)phenyl-N'-(3-(1-azabicyclo[5.4.0]undec-
3-en-4-yl)-1H-indol-5-yl)thiourea phenylacetate
N-(3-butoxy)phenyl-N'-(3-(1,2,3,4,5,8-hexahydroindolizin-
7-yl)-1H-indol-5-yl)thiourea hydrochloride
N-(2,3-dibromo)phenyl-N'-(3-(1,4,5,6,7,8,9-
heptahydroquinolizin-2-yl)-1H-indol-5-yl)thiourea
N-(2-bromo-3-iodo)phenyl-N'-(3-(1-azabicyclo[5.4.0]
undec-3-en-4-yl)-1H-indol-5-yl)thiourea
N-(3,4-difluoro)phenyl-N'-(3-(1,2,3,4,5,8-
hexahydroindolizin-7-yl)-1H-indol-5-yl)thiourea
N-(3-chloro-4-bromo)phenyl-N'-(3-(1,4,5,6,7,8,9-
heptahydroquinolizin-2-yl)-1H-indol-5-yl)thiourea
N-(2-bromo-4-fluoro)phenyl-N'-(3-(1-azabicyclo[5.4.0]
undec-3-en-4-yl)-1H-indol-5-yl)thiourea
N-(2,4-diiodo)phenyl-N'-(3-(1,2,3,4,5,8-
hexahydroindolizin-7-yl)-1H-indol-5-yl)thiourea
N-(2-chloro-5-iodo)phenyl-N'-(3-(1,2,3,4,5,8-
hexahydroindolizin-7-yl)-1H-indol-5-yl)thiourea
N-(2-fluoro-6-iodo)phenyl-N'-(3-(1,4,5,6,7,8,9-
heptahydroquinolizin-2-yl)-1H-indol-5-yl)thiourea
N-(3-fluoro-5-chloro)phenyl-N'-(3-(1-azabicyclo[5.4.0]
undec-3-en-4-yl)-1H-indol-5-yl)thiourea
N-phenethyl-N'-(3-[1,2,3,4,5,8-hexahydroindolizin-7-yl]-
1H-indol-5-yl)thiourea
N-(4-phenbutyl)-N'-(3-(1,4,5,6,7,8,9-heptahydroquinolizin-
2-yl)-1H-indol-5-yl)thiourea
N-(2-trifluoromethyl)phenyl-N'-(3-(1-azabicyclo[5.4.0]
undec-3-en-4-yl)-1H-indol-5-yl)thiourea
N-(3-phenyl)phenyl-N'-(3-(1,2,3,4,5,8-hexahydroindolizin-
7-yl)-1H-indol-5-yl)thiourea
N-propyl-N'-(3-(1-azabicyclo[5.4.0]undecan-4-yl)-1H-
indol-5-yl)thiourea
N-butyl-N'-(3-(octahydroindolizin-7-yl)-1H-indol-5-yl)
thiourea
N-(2-methoxy)phenyl-N'-(3-(octahydro-2H-quinolizin-2-
yl)-1H-indol-5-yl)thiourea
N-(4-ethoxy)phenyl-N'-(3-(1-azabicyclo[5.4.0]undecan-4-
yl)-1H-indol-5-yl)thiourea
N-(4-propoxy)phenyl-N'-(2-methyl-3-(octahydroindolizin-
7-yl)-1H-indol-5-yl)thiourea
N-(2-propoxy)phenyl-N'-(3-(octahydro-2H-quinolizin-2-yl)
-1H-indol-5-yl)thiourea
N-(2-isopropoxy)phenyl-N'-(3-(1-azabicyclo[5.4.0]
undecan-4-yl)-1H-indol-5-yl)thiourea
N-(4-butoxy)phenyl-N'-(3-(octahydroindolizin-7-yl)-1H-
indol-5-yl)thiourea
N-(2-butoxy)phenyl-N'-(3-(octahydro-2H-quinolizin-2-yl)-
1H-indol-5-yl)thiourea fumarate
N-(2-methoxy)phenyl-N'-(3-(1-azabicyclo[5.4.0]undecan-
4-yl)-1H-indol-5-yl)thiourea
N-(2,3-dibromo)phenyl-N'-(3-(octahydroindolizin-7-yl)-
1H-indol-5-yl)thiourea
N-(2-bromo-3-iodo)phenyl-N'-(3-(octahydro-2H-
quinolizin-2-yl)-1H-indol-5-yl)thiourea
N-(3,4-difluoro)phenyl-N'-(3-(1-azabicyclo[5.4.0]undecan-
4-yl)-1H-indol-5-yl)thiourea
N-(3-chloro-4-bromo)phenyl-N'-(3-(octahydroindolizin-7-
yl)-1H-indol-5-yl)thiourea
N-(2-bromo-4-fluoro)phenyl-N'-(3-(octahydro-2H-
quinolizin-2-yl)-1H-indol-5-yl)thiourea
N-(2,4-diiodo)phenyl-N'-(3-(1-azabicyclo[5.4.0]undecan-4-
yl)-1H-indol-5-yl)thiourea
N-(2-chloro-5-iodo)phenyl-N'-(3-(octahydroindolizin-7-yl)-
1H-indol-5-yl)thiourea
N-(2-fluoro-6-iodo)phenyl-N'-(3-(octahydro-2H-quinolizin-
2-yl)-1H-indol-5-yl)thiourea
N-(3-fluoro-5-chloro)phenyl-N'-(3-(1-azabicyclo[5.4.0]
undecan-4-yl)-1H-indol-5-yl)thiourea
N-(3-phenpropyl)-N'-(3-(octahydroindolizin-7-yl)-1H-
indol-5-yl)thiourea
N-(4-trifluoromethyl)phenyl-N'-(3-(octahydro-2H-
quinolizin-2-yl)-1H-indol-5-yl)thiourea N-(4-phenyl)phenyl-N'-(3-(1-azabicyclo[5.4.0]undecan-4-yl)-1H-indol-5-yl)thiourea
N-(2-bromo-3-iodo)phenyl-N'-(3-(1-azabicyclo[5.4.0]undec-3-en-4-yl)-1H-indol-5-yl)urea
N-(3,4-difluoro)phenyl-N'-(3-(1,2,3,4,5,8-hexahydroindolizin-7-yl)-1H-indol-5-yl)urea
N-(3-chloro-4-bromo)phenyl-N'-(3-(1,4,5,6,7,8,9-heptahydroquinolizin-2-yl)-1H-indol-5-yl)urea
N-(2-bromo-4-fluoro)phenyl-N'-(3-(1-azabicyclo[5.4.0]undec-3-en-4-yl)-1H-indol-5-yl)urea
N-(2,4-diiodo)phenyl-N'-(3-(1,2,3,4,5,8-hexahydroindolizin-7-yl)-1H-indol-5-yl)urea
N-(2-chloro-5-iodo)phenyl-N'-(3-(1,4,5,6,7,8,9-heptahydroquinolizin-2-yl)-1H-indol-5-yl)urea
N-(2-fluoro-6-iodo)phenyl-N'-(3-(1-azabicyclo[5.4.0]undec-3-en-4-yl)-1H-indol-5-yl)urea
N-(3-fluoro-5-chloro)phenyl-N'-(3-(1,2,3,4,5,8-hexahydroindolizin-7-yl)-1H-indol-5-yl)urea
N-(4-phenbutyl)-N'-(3-(1,4,5,6,7,8,9-heptahydroquinolizin-2-yl)-1H-indol-5-yl)urea
N-phenyl-N-propyl-N'-(3-(1-azabicyclo[5.4.0]undec-3-en-4-yl)-1H-indol-5-yl)urea
N-phenyl-N-butyl-N'-(3-(1,2,3,4,5,8-hexahydroindolizin-7-yl)-1H-indol-5-yl)urea
N-methyl-N-propyl-N'-(3-(1,4,5,6,7,8,9-heptahydroquinolizin-2-yl)-1H-indol-5-yl)urea
N-ethyl-N-isopropyl-N'-(3-(1-azabicyclo[5.4.0]undec-3-en-4-yl)-1H-indol-5-yl)urea
N,N-dipropyl-N'-(3-(1,2,3,4,5,8-hexahydroindolizin-7-yl)-1H-indol-5-yl)urea
N-butyl-N-propyl-N'-(3-(1,4,5,6,7,8,9-heptahydroquinolizin-2-yl)-1H-indol-5-yl)urea
N-butyl-N-isopropyl-N'-(3-(1-azabicyclo[5.4.0]undec-3-en-4-yl)-1H-indol-5-yl)urea
N-hexyl-N'-(3-(octahydroindolizin-7-yl)-1H-indol-5-yl)urea
N-(2-buten-4-yl)-N'-(3-(octahydro-2H-quinolizin-2-yl)-1H-indol-5-yl)urea
N-(2-penten-5-yl)-N'-(3-(1-azabicyclo[5.4.0]undecan-4-yl)-1H-indol-5-yl)urea
N-(1-hexen-6-yl)-N'-(3-(octahydroindolizin-7-yl)-1H-indol-5-yl)urea
N-(3-hexen-6-yl)-N'-(3-(1-(octahydro-2H-quinolizin-2-yl)-1H-indol-5-yl)urea
N-cyclopropyl-N'-(3-(1-azabicyclo[5.4.0]undecan-4-yl)-1H-indol-5-yl)urea
N-cyclopentyl-N'-(3-(octahydroindolizin-7-yl)-1H-indol-5-yl)urea
N-cyclooctyl-N'-(3-(octahydro-2H-quinolizin-2-yl)-1H-indol-5-yl)urea
N-(2-chloro)phenyl-N'-(3-(1-azabicyclo[5.4.0]undecan-4-yl)-1H-indol-5-yl)urea
N-(3-bromo)phenyl-N'-(3-(octahydroindolizin-7-yl)-1H-indol-5-yl)urea
N-(3-fluoro)phenyl-N'-(3-(octahydro-2H-quinolizin-2-yl)-1H-indol-5-yl)urea
N-(3-iodo)phenyl-N'-(2-methyl-3-(1-azabicyclo[5.4.0]undecan-4-yl)-1H-indol-5-yl)urea
N-(3-phenyl)phenyl-N'-(3-(octahydroindolizin-7-yl)-1H-indol-5-yl)urea
N-(4-ethoxy)phenyl-N'-(3-(octahydro-2H-quinolizin-2-yl)-1H-indol-5-yl)urea
N-(2-ethoxy)phenyl-N'-(3-(1-azabicyclo[5.4.0]undecan-4-yl)-1H-indol-5-yl)urea
N-(3-propoxy)phenyl-N'-(3-(octahydroindolizin-7-yl)-1H-indol-5-yl)urea
N-(2-isopropoxy)phenyl-N'-(3-(octahydro-2H-quinolizin-2-yl)-1H-indol-5-yl)urea
N-(4-isopropoxy)phenyl-N'-(3-(1-azabicyclo[5.4.0]undecan-4-yl)-1H-indol-5-yl)urea
N-(3-butoxy)phenyl-N'-(3-(octahydroindolizin-7-yl)-1H-indol-5-yl)urea
N-(4-formyl)phenyl-N'-(3-(octahydro-2H-quinolizin-2-yl)-1H-indol-5-yl)urea
N-(2-formyl)phenyl-N'-(3-(1-azabicyclo[5.4.0]undecan-4-yl)-1H-indol-5-yl)urea
N-(3-acetyl)phenyl-N'-(3-(octahydroindolizin-7-yl)-1H-indol-5-yl)urea phenylpropionate
N-(3-propanoyl)phenyl-N'-(3-(octahydro-2H-quinolizin-2-yl)-1H-indol-5-yl)urea
N-(3-ethylthio)phenyl-N'-(3-(1-azabicyclo[5.4.0]undecan-4-yl)-1H-indol-5-yl)urea
N-(2-ethylthio)phenyl-N'-(3-(octahydroindolizin-7-yl)-1H-indol-5-yl)urea
N-(3-propylthio)phenyl-N'-(3-(octahydro-2H-quinolizin-2-yl)-1H-indol-5-yl)urea
N-(3-isopropylthio)phenyl-N'-(3-(1-azabicyclo[5.4.0]undecan-4-yl)-1H-indol-5-yl)urea
N-(2-methyl)phenyl-N'-(3-(octahydroindolizin-7-yl)-1H-indol-5-yl)urea
N-(3-ethyl)phenyl-N'-(3-(octahydro-2H-quinolizin-2-yl)-1H-indol-5-yl)urea
N-(2-propyl)phenyl-N'-(3-(1-azabicyclo[5.4.0]undecan-4-yl)-1H-indol-5-yl)urea
N-(3-isopropyl)phenyl-N'-(3-(octahydroindolizin-7-yl)-1H-indol-5-yl)urea
N-(4-butyl)phenyl-N'-(3-(octahydro-2H-quinolizin-2-yl)-1H-indol-5-yl)urea
N-(2-butyl)phenyl-N'-(3-(1-azabicyclo[5.4.0]undecan-4-yl)-1H-indol-5-yl)urea
N-(3-methoxycarbonyl)phenyl-N'-(3-(octahydroindolizin-7-yl)-1H-indol-5-yl)urea
N-(2-ethoxycarbonyl)phenyl-N'-(3-(octahydro-2H-quinolizin-2-yl)-1H-indol-5-yl)urea
N-(4-ethoxycarbonyl)phenyl-N'-(3-(1-azabicyclo[5.4.0]undecan-4-yl)-1H-indol-5-yl)urea
N-(3-propoxycarbonyl)phenyl-N'-(3-(octahydroindolizin-7-yl)-1H-indol-5-yl)urea
N-(2-butoxycarbonyl)phenyl-N'-(3-(octahydro-2H-quinolizin-2-yl)-1H-indol-5-yl)urea
N-(2,3-dibromo)phenyl-N'-(3-(1-azabicyclo[5.4.0]undecan-4-yl)-1H-indol-5-yl)urea
N-(2-bromo-3-iodo)phenyl-N'-(3-(octahydroindolizin-7-yl)-1H-indol-5-yl)urea
N-(3,4-difluoro)phenyl-N'-(3-(octahydro-2H-quinolizin-2-yl)-1H-indol-5-yl)urea
N-(3-chloro-4-bromo)phenyl-N'-(3-(1-azabicyclo[5.4.0]undecan-4-yl)-1H-indol-5-yl)urea
N-(2-bromo-4-fluoro)phenyl-N'-(3-(octahydroindolizin-7-yl)-1H-indol-5-yl)urea
N-(2,4-diiodo)phenyl-N'-(3-(octahydro-2H-quinolizin-2-yl)-1H-indol-5-yl)urea
N-(2-chloro-5-iodo)phenyl-N'-(3-(1-azabicyclo[5.4.0]undecan-4-yl)-1H-indol-5-yl)urea
N-(2-fluoro-6-iodo)phenyl-N'-(3-(octahydroindolizin-7-yl)-1H-indol-5-yl)urea
N-(3-fluoro-5-chloro)phenyl-N'-(3-(octahydro-2H-quinolizin-2-yl)-1H-indol-5-yl)urea
N-(3-phenpropyl)-N'-(3-(1-azabicyclo[5.4.0]undecan-4-yl)-1H-indol-5-yl)urea
N-ethyl-N-phenyl-N'-(3-(octahydroindolizin-7-yl)-1H-indol-5-yl)urea
N-isopropyl-N-phenyl-N'-(3-(octahydro-2H-quinolizin-2-yl)-1H-indol-5-yl)urea
N-ethyl-N-methyl-N'-(3-(1-azabicyclo[5.4.0]undecan-4-yl)-1H-indol-5-yl)urea N-methyl-N-isopropyl-N'-(3-(octahydroindolizin-7-yl)-1H-indol-5-yl)urea
N-ethyl-N-propyl-N'-(3-(octahydro-2H-quinolizin-2-yl)-1H-indol-5-yl)urea
N-ethyl-N-butyl-N'-(3-(1-azabicyclo[5.4.0]undecan-4-yl)-1H-indol-5-yl)urea
N-propyl-N-isopropyl-N'-(3-(octahydroindolizin-7-yl)-1H-indol-5-yl)urea
N,N-diisopropyl-N'-(3-(octahydro-2H-quinolizin-2-yl)-1H-indol-5-yl)urea
N,N-dibutyl-N'-(3-(1-azabicyclo[5.4.0]undecan-4-yl)-1H-indol-5-yl)urea
5-isopropoxycarbonylamino-3-(1,2,3,4,5,8-hexahydroindolizin-7-yl)-2-ethyl-benzothiophene
5-(1-buten-4-yloxy)carbonylamino-3-(1,4,5,6,7,8,9-heptahydroquinolizin-2-yl)-1H-indole hydrochloride
5-(1-penten-5-yloxy)carbonylamino-3-(1-azabicyclo[5.4.0]undec-3-en-4-yl)-benzofuran
5-(1-buten-4-yloxy)carbonylamino-3-(1,2,3,4,5,8-hexahydroindolizin-7-yl)-benzothiophene
5-(3-penten-5-yloxy)carbonylamino-3-(1,4,5,6,7,8,9-heptahydroquinolizin-2-yl)-1H-indole
5-(2-hexen-6-yloxy)carbonylamino-3-(1-azabicyclo[5.4.0]undec-3-en-4-yl)-benzofuran
5-(4-hexen-6-yloxy)carbonylamino-3-(1,2,3,4,5,8-hexahydroindolizin-7-yl)-benzothiophene
5-(2-chlorophenoxy)carbonylamino-3-(1,4,5,6,7,8,9-heptahydroquinolizin-2-yl)-1H-indole
5-(3-fluorophenoxy)carbonylamino-3-(1-azabicyclo[5.4.0]undec-3-en-4-yl)-benzofuran
5-(3-bromophenoxy)carbonylamino-3-(1,2,3,4,5,8-hexahydroindolizin-7-yl)-benzothiophene
5-(2-bromophenoxy)carbonylamino-3-(1,4,5,6,7,8,9-heptahydroquinolizin-2-yl)-1H-indole
5-(3-iodophenoxy)carbonylamino-3-(1-azabicyclo[5.4.0]undec-3-en-4-yl)-benzofuran
5-(3-methoxyphenoxy)carbonylamino-3-(1,2,3,4,5,8-hexahydroindolizin-7-yl)-benzothiophene
5-(4-ethoxyphenoxy)carbonylamino-3-(1,4,5,6,7,8,9-heptahydroquinolizin-2-yl)-1H-indole
5-(2-ethoxy)phenoxycarbonylamino-3-(1-azabicyclo[5.4.0]undec-3-en-4-yl)-benzofuran
5-(3-propoxyphenoxy)carbonylamino-3-(1,2,3,4,5,8-hexahydroindolizin-7-yl)-benzothiophene
5-(2-butoxyphenoxy)carbonylamino-3-(1,4,5,6,7,8,9-heptahydroquinolizin-2-yl)-1H-indole
5-(4-butoxyphenoxy)carbonylamino-3-(1-azabicyclo[5.4.0]undec-3-en-4-yl)-benzofuran
5-cyclobutoxycarbonylamino-3-(1,2,3,4,5,8-hexahydroindolizin-7-yl)-benzothiophene
5-cyclooctyloxycarbonylamino-3-(1,4,5,6,7,8,9-heptahydroquinolizin-2-yl)-1H-indole
5-(butoxymethoxy)carbonylamino-3-(1-azabicyclo[5.4.0]undec-3-en-4-yl)-benzofuran
5-(ethoxypropoxy)carbonylamino-3-(1,2,3,4,5,8-hexahydroindolizin-7-yl)-benzothiophene
5-butoxycarbonylamino-3-(octahydroindolizin-7-yl)-2-propyl-1H-indole
5-(2-buten-4-yloxy)carbonylamino-3-(octahydro-2H-quinolizin-2-yl)-benzofuran
5-(2-penten-5-yloxy)carbonylamino-3-(1-azabicyclo[5.4.0]undecan-4-yl)-benzothiophene
5-(1-hexen-6-yloxy)carbonylamino-3-(octahydroindolizin-7-yl)-1H-indole
5-(3-hexen-6-yloxy)carbonylamino-3-(octahydro-2H-quinolizin-2-yl)-benzofuran
5-(3-chlorophenoxy)carbonylamino-3-(1-azabicyclo[5.4.0]undecan-4-yl)-benzothiophene
5-(2-fluorophenoxy)carbonylamino-3-(octahydroindolizin-7-yl)-1H-indole
5-(4-fluorophenoxy)carbonylamino-3-(octahydro-2H-quinolizin-2-yl)-benzofuran
5-(4-bromophenoxy)carbonylamino-3-(1-azabicyclo[5.4.0]undecan-4-yl)-benzothiophene
5-(2-iodophenoxy)carbonylamino-3-(octahydroindolizin-7-yl)-1H-indole
5-(4-iodophenoxy)carbonylamino-3-(octahydro-2H-quinolizin-2-yl)-benzofuran
5-(3-chlorophenoxy)carbonylamino-3-(1-azabicyclo[5.4.0]undecan-4-yl)-benzothiophene
5-(2-methoxyphenoxy)carbonylamino-3-(octahydroindolizin-7-yl)-2-ethyl-1H-indole citrate
5-(3-ethoxyphenoxy)carbonylamino-3-(octahydro-2H-quinolizin-2-yl)-benzofuran
5-(4-propoxyphenoxy)carbonylamino-3-(1-azabicyclo[5.4.0]undecan-4-yl)-benzothiophene
5-(2-propoxyphenoxy)carbonylamino-3-(octahydroindolizin-7-yl)-1H-indole
5-(3-butoxyphenoxy)carbonylamino-3-(octahydro-2H-quinolizin-2-yl)-benzofuran
5-cyclopropoxycarbonylamino-3-(1-azabicyclo[5.4.0]undecan-4-yl)-benzothiophene
5-cyclohexyloxycarbonylamino-3-(octahydroindolizin-7-yl)-1H-indole
5-cyclooctyloxycarbonylamino-3-(octahydro-2H-quinolizin-2-yl)-benzofuran
5-(propoxyethoxy)carbonylamino-3-(1-azabicyclo[5.4.0]undecan-4-yl)-benzothiophene
5-(4-methoxybutoxy)carbonylamino(octahydroindolizin-7-yl)-1H-indole
5-(acetyl)amino-3-(1,4,5,6,7,8,9-heptahydroquinolizin-2-yl)-benzofuran
5-(butyroyl)amino-3-(1-azabicyclo[5.4.0]undec-3-en-4-yl)-benzothiophene
5-(pentanoyl)amino-3-(1,2,3,4,5,8-hexahydroindolizin-7-yl)-1H-indole glycollate
5-(2-methylbutanoyl)amino-3-(1,4,5,6,7,8,9-heptahydroquinolizin-2-yl)-benzofuran
5-(2,2-dimethylpropanoyl)amino-3-(1-azabicyclo[5.4.0]undec-3-en-4-yl)-benzothiophene
5-(heptanoyl)amino-3-(1,2,3,4,5,8-hexahydroindolizin-7-yl)-1H-indole
5-(cyclooctylcarbonyl)amino-3-(1,4,5,6,7,8,9-heptahydroquinolizin-2-yl)-benzofuran
5-(4-phenylbutanoyl)amino-3-(1-azabicyclo[5.4.0]undec-3-en-4-yl)-benzothiophene
5-(phenoxyacetyl)amino-3-(1,2,3,4,5,8-hexahydroindolizin-7-yl)-1H-indole
5-(4-phenoxybutanoyl)amino-3-(1,4,5,6,7,8,9-heptahydroquinolizin-2-yl)-benzofuran
5-(butoxyacetyl)amino-3-(1-azabicyclo[5.4.0]undec-3-en-4-yl)-benzothiophene
5-(4-ethoxybutanoyl)amino-3-(1,2,3,4,5,8-hexahydroindolizin-7-yl)-1H-indole tartrate
5-(butoxycarbonylacetyl)amino-3-(1,4,5,6,7,8,9-heptahydroquinolizin-2-yl)-benzofuran
5-(4-butoxycarbonylbutanoyl)amino-3-(1-azabicyclo[5.4.0]undec-3-en-4-yl)-benzothiophene
5-benzoylamino-3-(1,2,3,4,5,8-hexahydroindolizin-7-yl)-1H-indole hydrochloride
5-benzoylamino-3-(1,4,5,6,7,8,9-heptahydroquinolizin-2-yl)-benzofuran
5-benzoylamino-3-(1-azabicyclo[5.4.0]undec-3-en-4-yl)-benzothiophene
5-benzoylamino-3-(1,2,3,4,5,8-hexahydroindolizin-7-yl)-1H-indole 5-benzoylamino-3-(1,4,5,6,7,8,9-heptahydroquinolizin-2-yl)-benzofuran
5-benzoylamino-3-(1-azabicyclo[5.4.0]undec-3-en-4-yl)-benzothiophene
5-benzoylamino-3-(1,2,3,4,5,8-hexahydroindolizin-7-yl)-1H-indole
5-benzoylamino-3-(1,4,5,6,7,8,9-heptahydroquinolizin-2-yl)-benzofuran
5-benzoylamino-3-(1-azabicyclo[5.4.0]undec-3-en-4-yl)-benzothiophene
5-benzoylamino-3-(1,2,3,4,5,8-hexahydroindolizin-7-yl)-1H-indole
5-benzoylamino-3-(1,4,5,6,7,8,9-heptahydroquinolizin-2-yl)-benzofuran propanesulfonate
5-benzoylamino-3-(1-azabicyclo[5.4.0]undec-3-en-4-yl)-benzothiophene
5-(4-fluorobenzoyl)amino-3-(1,2,3,4,5,8-hexahydroindolizin-7-yl)-1H-indole fumarate
5-(4-fluorobenzoyl)amino-3-(1,4,5,6,7,8,9-heptahydroquinolizin-2-yl)-benzofuran
5-(4-fluorobenzoyl)amino-3-(1-azabicyclo[5.4.0]undec-3-en-4-yl)-benzothiophene
5-(4-fluorobenzoyl)amino-3-(1,2,3,4,5,8-hexahydroindolizin-7-yl)-1H-indole
5-(4-fluorobenzoyl)amino-3-(1,4,5,6,7,8,9-heptahydroquinolizin-2-yl)-benzofuran
5-(4-fluorobenzoyl)amino-3-(1-azabicyclo[5.4.0]undec-3-en-4-yl)-benzothiophene
5-(4-fluorobenzoyl)amino-3-(1,2,3,4,5,8-hexahydroindolizin-7-yl)-1H-indole
5-(4-fluorobenzoyl)-N-methylamino-3-(1,4,5,6,7,8,9-heptahydroquinolizin-2-yl)-benzofuran naphthalene-1-sulfonate
5-(4-fluorobenzoyl)amino-3-(1-azabicyclo[5.4.0]undec-3-en-4-yl)-benzothiophene
5-(4-fluorobenzoyl)amino-3-(1,2,3,4,5,8-hexahydroindolizin-7-yl)-1H-indole
5-(4-fluorobenzoyl)amino-3-(1,4,5,6,7,8,9-heptahydroquinolizin-2-yl)-benzofuran
5-(4-fluorobenzoyl)amino-3-(1-azabicyclo[5.4.0]undec-3-en-4-yl)-benzothiophene
5-(2-chlorobenzoyl)amino-3-(1,2,3,4,5,8-hexahydroindolizin-7-yl)-1H-indole
5-(2-chlorobenzoyl)amino-3-(1,4,5,6,7,8,9-heptahydroquinolizin-2-yl)-benzofuran
5-(2-chlorobenzoyl)amino-3-(1-azabicyclo[5.4.0]undec-3-en-4-yl)-benzothiophene
5-(2-chlorobenzoyl)amino-3-(1,2,3,4,5,8-hexahydroindolizin-7-yl)-1H-indole
5-(2-chlorobenzoyl)amino-3-(1,4,5,6,7,8,9-heptahydroquinolizin-2-yl)-benzofuran
5-(2-chlorobenzoyl)amino-3-(1-azabicyclo[5.4.0]undec-3-en-4-yl)-benzothiophene
5-(2-chlorobenzoyl)amino-3-(1,2,3,4,5,8-hehexahydroindolizin-7-yl)-1H-indole
5-(2-chlorobenzoyl)-N-ethylamino-3-(1,4,5,6,7,8,9-heptahydroquinolizin-2-yl)-benzofuran
5-(2-chlorobenzoyl)amino-3-(1-azabicyclo[5.4.0]undec-3-en-4-yl)-benzothiophene
5-(2-chlorobenzoyl)amino-3-(1,2,3,4,5,8-hexahydroindolizin-7-yl)-1H-indole
5-(2-chlorobenzoyl)amino-3-(1,4,5,6,7,8,9-heptahydroquinolizin-2-yl)-benzofuran
5-(2-chlorobenzoyl)amino-3-(1-azabicyclo[5.4.0]undec-3-en-4-yl)-benzothiophene
5-(3-bromobenzoyl)amino-3-(1,2,3,4,5,8-hexahydroindolizin-7-yl)-1H-indole
5-(2-iodobenzoyl)-N-propylamino-3-(1,4,5,6,7,8,9-heptahydroquinolizin-2-yl)-benzofuran
5-(3-ethylbenzoyl)amino-3-(1-azabicyclo[5.4.0]undec-3-en-4-yl)-benzothiophene
5-(4-propylbenzoyl)amino-3-(1,2,3,4,5,8-hexahydroindolizin-7-yl)-1H-indole
5-(2-propylbenzoyl)amino-3-(1,4,5,6,7,8,9-heptahydroquinolizin-2-yl)-benzofuran
5-(3-butylbenzoyl)amino-3-(1-azabicyclo[5.4.0]undec-3-en-4-yl)-benzothiophene
5-(4-ethoxybenzoyl)amino-3-(1,2,3,4,5,8-hexahydroindolizin-7-yl)-1H-indole
5-(2-ethoxybenzoyl)-N-isopropylamino-3-(1,4,5,6,7,8,9-heptahydroquinolizin-2-yl)-benzofuran
5-(3-propoxybenzoyl)amino-3-(1-azabicyclo[5.4.0]undec-3-en-4-yl)-benzothiophene
5-(2-butoxybenzoyl)amino-3-(1,2,3,4,5,8-hexahydroindolizin-7-yl)-benzofuran
5-(4-butoxybenzoyl)amino-3-(1,4,5,6,7,8,9-heptahydroquinolizin-2-yl)-1H-indole
5-(3-pentoxybenzoyl)amino-3-(1-azabicyclo[5.4.0]undec-3-en-4-yl)-benzothiophene
5-(3-hexyloxybenzoyl)amino-3-(1,2,3,4,5,8-hexahydroindolizin-7-yl)-benzofuran
5-(3-heptyloxybenzoyl)amino-3-(1,4,5,6,7,8,9-heptahydroquinolizin-2-yl)-1H-indole
5-(2-octyloxybenzoyl)amino-3-(1-azabicyclo[5.4.0]undec-3-en-4-yl)-benzothiophene
5-(4-octyloxybenzoyl)amino-3-(1,2,3,4,5,8-hexahydroindolizin-7-yl)-benzofuran
5-(3-octyloxybenzoyl)amino-3-(1,4,5,6,7,8,9-heptahydroquinolizin-2-yl)-1H-indole
5-(3-methylthiobenzoyl)amino-3-(1-azabicyclo[5.4.0]undec-3-en-4-yl)-benzothiophene
5-(4-propylthiobenzoyl)-N-butylamino-3-(1,2,3,4,5,8-hexahydroindolizin-7-yl)-benzofuran
5-(2-propylthiobenzoyl)amino-3-(1,4,5,6,7,8,9-heptahydroquinolizin-2-yl)-1H-indole
5-(3-butylthiobenzoyl)amino-3-(1-azabicyclo[5.4.0]undec-3-en-4-yl)-benzothiophene
5-(2-nitrobenzoyl)amino-3-(1,2,3,4,5,8-hexahydroindolizin-7-yl)-benzofuran
5-(2-cyanobenzoyl)amino-3-(1,4,5,6,7,8,9-heptahydroquinolizin-2-yl)-1H-indole
5-(2-(dimethylamino)benzoyl)amino-3-(1-azabicyclo[5.4.0]undec-3-en-4-yl)-benzothiophene
5-(3-(diethylamino)benzoyl)amino-3-(1,2,3,4,5,8-hexahydroindolizin-7-yl)-benzofuran
5-(4-(dipropylamino)benzoyl)amino-3-(1,4,5,6,7,8,9-heptahydroquinolizin-2-yl)-1H-indole
5-(2-trifluoromethoxybenzoyl)amino-3-(1-azabicyclo[5.4.0]undec-3-en-4-yl)-benzothiophene
5-(3-trifluoromethoxybenzoyl)amino-3-(1,2,3,4,5,8-hexahydroindolizin-7-yl)-benzofuran
5-(3-formylbenzoyl)amino-3-(1,4,5,6,7,8,9-heptahydroquinolizin-2-yl)-1H-indole
5-(3-acetylbenzoyl)amino-3-(1-azabicyclo[5.4.0]undec-3-en-4-yl)-benzothiophene
5-(2-(propanoyl)benzoyl)amino-3-(1,2,3,4,5,8-hexahydroindolizin-7-yl)-benzofuran
5-(4-(propanoyl)benzoyl)amino-3-(1,4,5,6,7,8,9-heptahydroquinolizin-2-yl)-1H-indole
5-(3-(butanoyl)benzoyl)amino-3-(1-azabicyclo[5.4.0]undec-3-en-4-yl)-benzothiophene
5-(3-(benzoyl)benzoyl)amino-3-(1,2,3,4,5,8-hexahydroindolizin-7-yl)-benzofuran
5-(3-methanesulfonylbenzoyl)amino-3-(1,4,5,6,7,8,9-heptahydroquinolizin-2-yl)-1H-indole 5-(3-ethanesulfonylbenzoyl)amino-3-(1-azabicyclo[5.4.0]
undec-3-en-4-yl)-benzothiophene
5-(2-butanesulfonylbenzoyl)amino-3-(1,2,3,4,5,8-
hexahydroindolizin-7-yl)-benzofuran
5-(3-butanesulfonylbenzoyl)amino-3-(1,4,5,6,7,8,9-
heptahydroquinolizin-2-yl)-1H-indole
5-(2-phenylbenzoyl)amino-3-(1-azabicyclo[5.4.0]undec-3-
en-4-yl)-benzothiophene
5-(2,3-dibromo)benzoylamino-3-(1,2,3,4,5,8-
hexahydroindolizin-7-yl)-benzofuran
5-(2-bromo-3-iodo)benzoylamino-3-(1,4,5,6,7,8,9-
heptahydroquinolizin-2-yl)-1H-indole
5-(3,4-difluoro)benzoylamino-3-(1-azabicyclo[5.4.0]undec-
3-en-4-yl)-benzothiophene
5-(3-chloro-4-bromo)benzoylamino-3-(1,2,3,4,5,8-
hexahydroindolizin-7-yl)-benzofuran
5-(2-bromo-4-fluoro)benzoylamino-3-(1,4,5,6,7,8,9-
heptahydroquinolizin-2-yl)-1H-indole
5-(2,4-diiodo)benzoylamino-3-(1-azabicyclo[5.4.0]undec-
3-en-4-yl)-benzothiophene
5-(2-chloro-5-iodo)benzoylamino-3-(1,2,3,4,5,8-
hexahydroindolizin-7-yl)-benzofuran
5-(2-fluoro-6-iodo)benzoylamino-3-(1,4,5,6,7,8,9-
heptahydroquinolizin-2-yl)-1H-indole
5-(3-fluoro-5-chloro)benzoylamino-3-(1-azabicyclo[5.4.0]
undec-3-en-4-yl)-benzothiophene
5-(2-thienoyl)amino-3-(1,2,3,4,5,8-hexahydroindolizin-7-
yl)-benzofuran
5-(2-thienoyl)amino-3-(1,4,5,6,7,8,9-heptahydroquinolizin-
2-yl)-1H-indole
5-(2-thienoyl)amino-3-(1-azabicyclo[5.4.0]undec-3-en-4-
yl)-benzothiophene
5-(2-thienoyl)amino-3-(1,2,3,4,5,8-hexahydroindolizin-7-
yl)-benzofuran
5-(2-thienoyl)amino-3-(1,4,5,6,7,8,9-heptahydroquinolizin-
2-yl)-1H-indole
5-(2-thienoyl)amino-3-(1-azabicyclo[5.4.0]undec-3-en-4-yl)-
benzothiophene
5-(2-thienoyl)amino-3-(1,2,3,4,5,8-hexahydroindolizin-7-
yl)-benzofuran
5-(2-thienoyl)amino-3-(1,4,5,6,7,8,9-heptahydroquinolizin-
2-yl)-1H-indole
5-(2-thienoyl)amino-3-(1-azabicyclo[5.4.0]undec-3-en-4-
yl)-benzothiophene
5-(2-thienoyl)amino-3-(1,2,3,4,5,8-hexahydroindolizin-7-
yl)-benzofuran
5-(2-thienoyl)amino-3-(1,4,5,6,7,8,9-heptahydroquinolizin-
2-yl)-1H-indole
5-(2-thienoyl)amino-3-(1-azabicyclo[5.4.0]undec-3-en-4-
yl)-benzothiophene
5-(3-thienoyl)amino-3-(1,2,3,4,5,8-hexahydroindolizin-7-
yl)-benzofuran
5-(3-thienoyl)amino-3-(1,4,5,6,7,8,9-heptahydroquinolizin-
2-yl)-1H-indole
5-(3-thienoyl)amino-3-(1-azabicyclo[5.4.0]undec-3-en-4-
yl)-benzothiophene
5-(3-thienoyl)amino-3-(1,2,3,4,5,8-hexahydroindolizin-7-
yl)-benzofuran
5-(3-thienoyl)amino-3-(1,4,5,6,7,8,9-heptahydroquinolizin-
2-yl)-1H-indole
5-(3-thienoyl)amino-3-(1-azabicyclo[5.4.0]undec-3-en-4-
yl)-benzothiophene
5-(3-thienoyl)amino-3-(1,2,3,4,5,8-hexahydroindolizin-7-
yl)-benzofuran
5-(3-thienoyl)amino-3-(1,4,5,6,7,8,9-heptahydroquinolizin-
2-yl)-1H-indole
5-(3-thienoyl)amino-3-(1-azabicyclo[5.4.0]undec-3-en-4-
yl)-benzothiophene
5-(3-thienoyl)amino-3-(1,2,3,4,5,8-hexahydroindolizin-7-
yl)-benzofuran
5-(3-thienoyl)amino-3-(1,4,5,6,7,8,9-heptahydroquinolizin-
2-yl)-1H-indole
5-(3-thienoyl)amino-3-(1-azabicyclo[5.4.0]undec-3-en-4-
yl)-benzothiophene
5-(2-furoyl)amino-3-(1,2,3,4,5,8-hexahydroindolizin-7-yl)-
benzofuran
5-(2-furoyl)amino-3-(1,4,5,6,7,8,9-heptahydroquinolizin-2-
yl)-1H-indole
5-(2-furoyl)amino-3-(1-azabicyclo[5.4.0]undec-3-en-4-yl)-
benzothiophene
5-(2-furoyl)amino-3-(1,2,3,4,5,8-hexahydroindolizin-7-yl)-
benzofuran
5-(2-furoyl)amino-3-(1,4,5,6,7,8,9-heptahydroquinolizin-2-
yl)-1H-indole
5-(2-furoyl)amino-3-(1-azabicyclo[5.4.0]undec-3-en-4-yl)-
benzothiophene
5-(2-furoyl)amino-3-(octahydro-2H-quinolizin-2-yl)-
benzofuran
5-(2-furoyl)amino-3-(1,2,3,4,5,8-hexahydroindolizin-7-yl)-
1H-indole
5-(2-furoyl)amino-3-(1,4,5,6,7,8,9-heptahydroquinolizin-2-
yl)-benzothiophene
5-(2-furoyl)amino-3-(1-azabicyclo[5.4.0]undec-3-en-4-yl)-
benzofuran
5-(2-furoyl)amino-3-(1,2,3,4,5,8-hexahydroindolizin-7-yl)-
1H-indole
5-(2-furoyl)amino-3-(1,4,5,6,7,8,9-heptahydroquinolizin-2-
yl)-benzothiophene
5-(3-furoyl)amino-3-(1-azabicyclo[5.4.0]undec-3-en-4-yl)-
benzofuran
5-(3-furoyl)amino-3-(1,2,3,4,5,8-hexahydroindolizin-7-yl)-
1H-indole
5-(3-furoyl)amino-3-(1,4,5,6,7,8,9-heptahydroquinolizin-2-
yl)-benzothiophene
5-(3-furoyl)amino-3-(1-azabicyclo[5.4.0]undec-3-en-4-yl)-
benzofuran
5-(3-furoyl)amino-3-(1,2,3,4,5,8-hexahydroindolizin-7-yl)-
1H-indole
5-(3-furoyl)amino-3-(1,4,5,6,7,8,9-heptahydroquinolizin-2-
yl)-benzothiophene
5-(3-furoyl)amino-3-(1-azabicyclo[5.4.0]undec-3-en-4-yl)-
benzofuran
5-(3-furoyl)amino-3-(1,2,3,4,5,8-hexahydroindolizin-7-yl)-
1H-indole
5-(3-furoyl)amino-3-(1,4,5,6,7,8,9-heptahydroquinolizin-2-
yl)-benzothiophene naphthalene-2-sulfonate
5-(3-furoyl)amino-3-(1-azabicyclo[5.4.0]undec-3-en-4-yl)-
benzofuran
5-(3-furoyl)amino-3-(1,2,3,4,5,8-hexahydroindolizin-7-yl)-
1H-indole
5-(3-furoyl)amino-3-(1,4,5,6,7,8,9-heptahydroquinolizin-2-
yl)-benzothiophene
5-(propanoyl)amino-3-(octahydroindolizin-7-yl)-
benzofuran mandalate
5-(2-methylpropanoyl)amino-3-(octahydro-2H-quinolizin-
2-yl)-1H-indole
5-(2-methyl-4-butyn-1-oyl)amino-3-(1-azabicyclo[5.4.0]
undecan-4-yl)-benzothiophene
5-(2-methylbutanoyl)-N-methylamino-3-
(octahydroindolizin-7-yl)-benzofuran
5-(hex-3-enoyl)amino-3-(octahydro-2H-quinolizin-2-yl)-
1H-indole
5-(cyclohexaneacetyl)amino-3-(1-azabicyclo[5.4.0]
undecan-4-yl)-benzothiophene
5-(cycloheptylcarbonyl)amino-3-(octahydroindolizin-7-yl)-
benzofuran 5-(4-phenylbutanoyl)amino-3-(octahydro-2H-quinolizin-2-yl)-1H-indole
5-(5-phenylpentanoyl)amino-3-(1-azabicyclo[5.4.0]undecan-4-yl)-benzothiophene
5-(3-phenoxypropanoyl)amino-3-(octahydroindolizin-7-yl)-benzofuran
5-(5-phenoxypentanoyl)amino-3-(octahydro-2H-quinolizin-2-yl)-1H-indole
5-(3-propoxypropanoyl)amino-3-(1-azabicyclo[5.4.0]undecan-4-yl)-benzothiophene
5-(5-methoxypentanoyl)amino-3-(octahydroindolizin-7-yl)-benzofuran
5-((3-propoxycarbonyl)propanoyl)amino-3-(octahydro-2H-quinolizin-2-yl)-1H-indole
5-((5-methoxycarbonyl)pentanoyl)amino-3-(1-azabicyclo[5.4.0]undecan-4-yl)-benzothiophene
5-(benzoyl-N-ethyl)amino-3-(octahydroindolizin-7-yl)-benzofuran
5-benzoylamino-3-(octahydro-2H-quinolizin-2-yl)-1H-indole
5-benzoylamino-3-(1-azabicyclo[5.4.0]undecan-4-yl)-benzothiophene
5-benzoylamino-3-(octahydroindolizin-7-yl)-benzofuran
5-benzoylamino-3-(octahydro-2H-quinolizin-2-yl)-1H-indole
5-benzoylamino-3-(1-azabicyclo[5.4.0]undecan-4-yl)-benzothiophene
5-benzoylamino-3-(octahydroindolizin-7-yl)-benzofuran
5-benzoylamino-3-(octahydro-2H-quinolizin-2-yl)-1H-indole hydrochloride
5-benzoyl-N-propylamino-3-(1-azabicyclo[5.4.0]undecan-4-yl)-benzothiophene
5-benzoylamino-3-(octahydroindolizin-7-yl)-benzofuran
5-benzoylamino-3-(octahydro-2H-quinolizin-2-yl)-1H-indole
5-benzoylamino-3-(1-azabicyclo[5.4.0]undecan-4-yl)-benzothiophene
5-benzoylamino-3-(octahydroindolizin-7-yl)-benzofuran
5-(4-fluorobenzoyl)amino-3-(octahydro-2H-quinolizin-2-yl)-1H-indole
5-(4-fluorobenzoyl)amino-3-(1-azabicyclo[5.4.0]undecan-4-yl)-benzothiophene
5-(4-fluorobenzoyl)amino-3-(octahydroindolizin-7-yl)-benzofuran
5-(4-fluorobenzoyl)amino-3-(octahydro-2H-quinolizin-2-yl)-1H-indole
5-(4-fluorobenzoyl)amino-3-(1-azabicyclo[5.4.0]undecan-4-yl)-benzothiophene
5-(4-fluorobenzoyl)amino-3-(octahydroindolizin-7-yl)-benzofuran
5-(4-fluorobenzoyl)amino-3-(octahydro-2H-quinolizin-2-yl)-1H-indole
5-(4-fluorobenzoyl)amino-3-(1-azabicyclo[5.4.0]undecan-4-yl)-benzothiophene
5-(4-fluorobenzoyl)amino-3-(octahydroindolizin-7-yl)-benzofuran
5-(4-fluorobenzoyl)amino-3-(octahydro-2H-quinolizin-2-yl)-1H-indole
5-(4-fluorobenzoyl)amino-3-(1-azabicyclo[5.4.0]undecan-4-yl)-benzothiophene fumarate
5-(4-fluorobenzoyl)amino-3-(octahydroindolizin-7-yl)-benzofuran
5-(2-chlorobenzoyl)amino-3-(octahydro-2H-quinolizin-2-yl)-1H-indole
5-(2-chlorobenzoyl)amino-3-(1-azabicyclo[5.4.0]undecan-4-yl)-benzothiophene
5-(2-chlorobenzoyl)amino-3-(octahydroindolizin-7-yl)-benzofuran
5-(2-chlorobenzoyl)amino-3-(octahydro-2H-quinolizin-2-yl)-1H-indole
5-(2-chlorobenzoyl)amino-3-(1-azabicyclo[5.4.0]undecan-4-yl)-benzothiophene
5-(2-chlorobenzoyl)amino-3-(octahydroindolizin-7-yl)-benzofuran
5-(2-chlorobenzoyl)amino-3-(octahydro-2H-quinolizin-2-yl)-1H-indole
5-(2-chlorobenzoyl)amino-3-(1-azabicyclo[5.4.0]undecan-4-yl)-benzothiophene
5-(2-chlorobenzoyl)amino-3-(octahydroindolizin-7-yl)-benzofuran
5-(2-chlorobenzoyl)amino-3-(octahydro-2H-quinolizin-2-yl)-1H-indole
5-(2-chlorobenzoyl)amino-3-(1-azabicyclo[5.4.0]undecan-4-yl)-benzothiophene
5-(2-chlorobenzoyl)amino-3-(octahydroindolizin-7-yl)-benzofuran
5-(2-bromobenzoyl)amino-3-(octahydro-2H-quinolizin-2-yl)-1H-indole
5-(4-ethylbenzoyl)amino-3-(1-azabicyclo[5.4.0]undecan-4-yl)-benzothiophene
5-(2-ethylbenzoyl)amino-3-(octahydroindolizin-7-yl)-benzofuran
5-(3-propylbenzoyl)amino-3-(octahydro-2H-quinolizin-2-yl)-1H-indole
5-(4-butylbenzoyl)amino-3-(1-azabicyclo[5.4.0]undecan-4-yl)-benzothiophene
5-(2-butylbenzoyl)amino-3-(octahydroindolizin-7-yl)-benzofuran
5-(3-ethoxybenzoyl)amino-3-(octahydro-2H-quinolizin-2-yl)-1H-indole
5-(2-propoxybenzoyl)amino-3-(1-azabicyclo[5.4.0]undecan-4-yl)-benzothiophene
5-(3-butoxybenzoyl)amino-3-(octahydroindolizin-7-yl)-benzofuran
5-(4-pentyloxybenzoyl)amino-3-(octahydro-2H-quinolizin-2-yl)-1H-indole
5-(2-pentyloxybenzoyl)amino-3-(1-azabicyclo[5.4.0]undecan-4-yl)-benzothiophene
5-(2-hexyloxybenzoyl)amino-3-(octahydroindolizin-7-yl)-benzofuran
5-(4-hexyloxybenzoyl)amino-3-(octahydro-2H-quinolizin-2-yl)-1H-indole
5-(2-methylthiobenzoyl)amino-3-(1-azabicyclo[5.4.0]undecan-4-yl)-benzothiophene
5-(2-ethylthiobenzoyl)amino-3-(octahydroindolizin-7-yl)-benzofuran
5-(3-propylthiobenzoyl)amino-3-(octahydro-2H-quinolizin-2-yl)-1H-indole
5-(3-nitrobenzoyl)amino-3-(1-azabicyclo[5.4.0]undecan-4-yl)-benzothiophene
5-(3-cyanobenzoyl)amino-3-(octahydroindolizin-7-yl)-benzofuran
5-(4-(dimethylamino)benzoyl)amino-3-(octahydro-2H-quinolizin-2-yl)-1H-indole
5-(2-(diethylamino)benzoyl)-N-propylamino-3-(1-azabicyclo[5.4.0]undecan-4-yl)-benzothiophene
5-(4-(diethylamino)benzoyl)amino-3-(octahydroindolizin-7-yl)-benzofuran
5-(3-(dibutylamino)benzoyl)amino-3-(octahydro-2H-quinolizin-2-yl)-1H-indole
5-(4-trifluoromethoxybenzoyl)amino-3-(1-azabicyclo[5.4.0]undecan-4-yl)-benzothiophene
5-(4-(formyl)benzoyl)amino-3-(octahydroindolizin-7-yl)-benzofuran
5-(2-(formyl)benzoyl)amino-3-(octahydro-2H-quinolizin-2-yl)-1H-indole 5-(2-(acetyl)benzoyl)amino-3-(1-azabicyclo[5.4.0]undecan-4-yl)-benzothiophene
5-(3-(propanoyl)benzoyl)amino-3-(octahydroindolizin-7-yl)-benzofuran
5-(3-(butanoyl)benzoyl)amino-3-(octahydro-2H-quinolizin-2-yl)-1H-indole
5-(2-(butanoyl)benzoyl)amino-3-(1-azabicyclo[5.4.0]undecan-4-yl)-benzothiophene
5-(2-(benzoyl)benzoyl)amino-3-(octahydroindolizin-7-yl)-benzofuran
5-(2-(methanesulfonyl)benzoyl)amino-3-(octahydro-2H-quinolizin-2-yl)-1H-indole
5-(3-(propanesulfonyl)benzoyl)amino-3-(1-azabicyclo[5.4.0]undecan-4-yl)-benzothiophene
5-(2-butanesulfonylbenzoyl)amino-3-(octahydroindolizin-7-yl)-benzofuran
5-(3-phenylbenzoyl)amino-3-(octahydro-2H-quinolizin-2-yl)-1H-indole
5-(2,3-dibromo)benzoyl-N-isopropylamino-3-(1-azabicyclo[5.4.0]undecan-4-yl)-benzothiophene
5-(2-bromo-3-iodo)benzoylamino-3-(octahydroindolizin-7-yl)-benzofuran
5-(3,4-difluoro)benzoylamino-3-(octahydro-2H-quinolizin-2-yl)-1H-indole
5-(3-chloro-4-bromo)benzoylamino-3-(1-azabicyclo[5.4.0]undecan-4-yl)-benzothiophene
5-(2-bromo-4-fluoro)benzoylamino-(3-(octahydroindolizin-7-yl)-benzofuran
5-(2,4-diiodo)benzoylamino-(3-(octahydro-2H-quinolizin-2-yl)-1H-indole
5-(2-chloro-5-iodo)benzoylamino-(3-(1-azabicyclo[5.4.0]undecan-4-yl)-benzothiophene
5-(2-fluoro-6-iodo)benzoylamino-(3-(octahydroindolizin-7-yl)-benzofuran
5-(3-fluoro-5-chloro)benzoylamino-3-(octahydro-2H-quinolizin-2-yl)-1H-indole
5-(2-thienoyl)-N-butylamino-3-(1-azabicyclo[5.4.0]undecan-4-yl)-benzothiophene
5-(2-thienoyl)amino-3-(octahydroindolizin-7-yl)-benzofuran
5-(2-thienoyl)amino-3-(octahydro-2H-quinolizin-2-yl)-1H-indole
5-(2-thienoyl)amino-3-(1-azabicyclo[5.4.0]undecan-4-yl)-benzothiophene
5-(2-thienoyl)amino-3-(octahydroindolizin-7-yl)-benzofuran
5-(2-thienoyl)amino-3-(octahydro-2H-quinolizin-2-yl)-1H-indole
5-(2-thienoyl)amino-3-(1-azabicyclo[5.4.0]undecan-4-yl)-benzothiophene
5-(2-thienoyl)amino-3-(octahydroindolizin-7-yl)-benzofuran
5-(2-thienoyl)amino-3-(octahydro-2H-quinolizin-2-yl)-1H-indole
5-(2-thienoyl)amino-3-(1-azabicyclo[5.4.0]undecan-4-yl)-benzothiophene
5-(2-thienoyl)amino-3-(octahydroindolizin-7-yl)-benzofuran
5-(2-thienoyl)amino-3-(octahydro-2H-quinolizin-2-yl)-1H-indole
5-(3-thienoyl)amino-3-(1-azabicyclo[5.4.0]undecan-4-yl)-benzothiophene
5-(3-thienoyl)amino-3-(octahydroindolizin-7-yl)-benzofuran
5-(3-thienoyl)amino-3-(octahydro-2H-quinolizin-2-yl)-1H-indole
5-(3-thienoyl)amino-3-(1-azabicyclo[5.4.0]undecan-4-yl)-benzothiophene
5-(3-thienoyl)amino-3-(octahydroindolizin-7-yl)-benzofuran
5-(3-thienoyl)amino-3-(octahydro-2H-quinolizin-2-yl)-1H-indole
5-(3-thienoyl)amino-3-(1-azabicyclo[5.4.0]undecan-4-yl)-benzothiophene
5-(3-thienoyl)amino-3-(octahydroindolizin-7-yl)-benzofuran
5-(3-thienoyl)amino-3-(octahydro-2H-quinolizin-2-yl)-1H-indole
5-(3-thienoyl)amino-3-(1-azabicyclo[5.4.0]undecan-4-yl)-benzothiophene
5-(3-thienoyl)amino-3-(octahydroindolizin-7-yl)-benzofuran
5-(3-thienoyl)amino-3-(octahydro-2H-quinolizin-2-yl)-1H-indole
5-(2-furoyl)amino-3-(1-azabicyclo[5.4.0]undecan-4-yl)-benzothiophene
5-(2-furoyl)amino-3-(octahydroindolizin-7-yl)-benzofuran
5-(2-furoyl)amino-3-(octahydro-2H-quinolizin-2-yl)-1H-indole
5-(2-furoyl)amino-3-(1-azabicyclo[5.4.0]undecan-4-yl)-benzothiophene
5-(2-furoyl)amino-3-(octahydroindolizin-7-yl)-benzofuran
5-(2-furoyl)amino-3-(octahydro-2H-quinolizin-2-yl)-1H-indole
5-(2-furoyl)amino-3-(1-azabicyclo[5.4.0]undecan-4-yl)-benzothiophene
5-(2-furoyl)amino-3-(octahydroindolizin-7-yl)-benzofuran
5-(2-furoyl)amino-3-(octahydro-2H-quinolizin-2-yl)-1H-indole
5-(2-furoyl)amino-3-(1-azabicyclo[5.4.0]undecan-4-yl)-benzothiophene
5-(2-furoyl)amino-3-(octahydroindolizin-7-yl)-benzofuran
5-(2-furoyl)amino-3-(octahydro-2H-quinolizin-2-yl)-1H-indole
5-(3-furoyl)amino-3-(1-azabicyclo[5.4.0]undecan-4-yl)-benzothiophene
5-(3-furoyl)amino-3-(octahydroindolizin-7-yl)-benzofuran
5-(3-furoyl)amino-3-(octahydro-2H-quinolizin-2-yl)-1H-indole
5-(3-furoyl)amino-3-(1-azabicyclo[5.4.0]undecan-4-yl)-benzothiophene
5-(3-furoyl)amino-3-(octahydroindolizin-7-yl)-benzofuran
5-(3-furoyl)amino-3-(octahydro-2H-quinolizin-2-yl)-1H-indole
5-(3-furoyl)amino-3-(1-azabicyclo[5.4.0]undecan-4-yl)-benzothiophene
5-(3-furoyl)amino-3-(octahydroindolizin-7-yl)-benzofuran
5-(3-furoyl)amino-3-(octahydro-2H-quinolizin-2-yl)-1H-indole
5-(3-furoyl)amino-3-(1-azabicyclo[5.4.0]undecan-4-yl)-benzothiophene
5-(3-furoyl)amino-3-(octahydroindolizin-7-yl)-1H-indole
5-(3-furoyl)amino-3-(octahydro-2H-quinolizin-2-yl)-benzofuran
N-[pyridin-2-yl]-5-carboxamido-3-(1,2,5,6-tetrahydropyridin-4-yl)-1H-indole
N-[fur-3-yl]-5-carboxamido-3-(1,2,5,6-tetrahydropyridin-4-yl)-benzothiophene
N-[pyrazol-3-yl]-5-carboxamido-3-(1,2,5,6-tetrahydropyridin-4-yl)-benzofuran
N-[thiazol-2-yl]-5-carboxamido-3-(1,2,5,6-tetrahydropyridin-4-yl)-1H-indole
N-[quinolin-4-yl]-5-carboxamido-3-(1,2,5,6-tetrahydropyridin-4-yl)-benzothiophene
N-[imidazol-4-yl]-5-carboxamido-3-(1-azabicyclo[5.4.0]undecan-4-yl)-benzofuran N-[fur-3-yl]-5-carboxamido-3-(1,2,5,6-tetrahydropyridin-4-yl)-1H-indole N-[pyrimidin-5-yl]-5-carboxamido-3-(octahydroindolizin-7-yl)-benzothiophene N-[indol-2-yl]-5-carboxamido-3-(octahydro-2H-quinolizin-2-yl)-benzofuran N-[isoxazol-5-yl]-5-carboxamido-3-(1-azabicyclo[5.4.0]undecan-4-yl)-1H-indole 5-amino-3-(1,2,3,4,5,8-hexahydroindolizin-7-yl)pyrrolo[3,2-b]pyridine 5-(3-chlorophenyl)thio-3-(1,4,5,6,7,8,9-heptahydroquinolizin-2-yl)-2-methylpyrrolo[3,2-b]pyridine 5-(2-pyridinyl)thio-3-(1-azabicyclo[5.4.0]undec-3-en-4-yl)pyrrolo[3,2-b]pyridine decanoate 5-propanoyl-3-(1,2,3,4,5,8-hexahydroindolizin-7-yl)pyrrolo[3,2-b]pyridine suberate 5-(3,3-dimethylbutanoyl)-3-(1-azabicyclo[5.4.0]undec-3-en-4-yl)pyrrolo[3,2-b]pyridine 5-(3-fluorobenzoyl)-3-(1-azabicyclo[5.4.0]undec-3-en-4-yl)pyrrolo[3,2-b]pyridine 5-(3-pyridinecarbonyl)-3-(1,4,5,6,7,8,9-heptahydroquinolizin-2-yl)pyrrolo[3,2-b]pyridine 5-(N-phenyl)carboxamido-3-(1,2,3,4,5,8-hexahydroindolizin-7-yl)-2-methylpyrrolo[3,2-b]pyridine 2,4-dinitrobenzoate 5-(N-benzyl)carboxamido-3-(1,4,5,6,7,8,9-heptahydroquinolizin-2-yl)pyrrolo[3,2-b]pyridine 5-(N-(2-(4-chlorophenyl)ethyl))carboxamido-3-(1-azabicyclo[5.4.0]undec-3-en-4-yl)pyrrolo[3,2-b]pyridine 4-hydroxybenzoate 5-(N-isopropyl-N-sec-butanesulfonyl)amino-3-(1-azabicyclo[5.4.0]undecan-4-yl)pyrrolo[3,2-b]pyridine 5-(N-(tert-butyl)sulfonyl)amino-3-(octahydroindolizin-7-yl)pyrrolo[3,2-b]pyridine 5-(N,N-diethylaminosulfonyl)amino-3-(octahydro-2H-quinolizin-2-yl)pyrrolo[3,2-b]pyridine N-ethyl-N'-(3-(1,2,3,4,5,8-hexahydroindolizin-7-yl)pyrrolo[3,2-b]pyridin-5-yl)thiourea N-isopropyl-N'-(3-(1,4,5,6,7,8,9-heptahydroquinolizin-2-yl)pyrrolo[3,2-b]pyridin-5-yl)thiourea N-(3-methoxy)phenyl-N'-(3-(1-azabicyclo[5.4.0]undec-3-en-4-yl)pyrrolo[3,2-b]pyridin-5-yl)thiourea N-(2-bromo-3-iodo)phenyl-N'-(3-(1-azabicyclo[5.4.0]undec-3-en-4-yl)pyrrolo[3,2-b]pyridin-5-yl)urea N-(3,4-difluoro)phenyl-N'-(3-(1,2,3,4,5,8-hexahydroindolizin-7-yl)pyrrolo[3,2-b]pyridin-5-yl)urea N-(3-chloro-4-bromo)phenyl-N'-(3-(1,4,5,6,7,8,9-heptahydroquinolizin-2-yl)pyrrolo[3,2-b]pyridin-5-yl)urea N-(2-bromo-4-fluoro)phenyl-N'-(3-(1-azabicyclo[5.4.0]undec-3-en-4-yl)pyrrolo[3,2-b]pyridin-5-yl)urea N-methyl-N-propyl-N'-(3-(1,4,5,6,7,8,9-heptahydroquinolizin-2-yl)pyrrolo[3,2-b]pyridin-5-yl)urea N-ethyl-N-isopropyl-N'-(3-(1-azabicyclo[5.4.0]undec-3-en-4-yl)pyrrolo[3,2-b]pyridin-5-yl)urea N,N-dipropyl-N'-(3-(1,2,3,4,5,8-hexahydroindolizin-7-yl)pyrrolo[3,2-b]pyridin-5-yl)urea N-butyl-N-propyl-N'-(3-(1,4,5,6,7,8,9-heptahydroquinolizin-2-yl)pyrrolo[3,2-b]pyridin-5-yl)urea N-butyl-N-isopropyl-N'-(3-(1-azabicyclo[5.4.0]undec-3-en-4-yl)pyrrolo[3,2-b]pyridin-5-yl)urea N-hexyl-N'-(3-(octahydroindolizin-7-yl)pyrrolo[3,2-b]pyridin-5-yl)urea N-(2-buten-4-yl)-N'-(3-(octahydro-2H-quinolizin-2-yl)pyrrolo[3,2-b]pyridin-5-yl)urea N-cyclopentyl-N'-(3-(octahydroindolizin-7-yl)pyrrolo[3,2-b]pyridin-5-yl)urea 5-isopropoxycarbonylamino-3-(1,2,3,4,5,8-hexahydroindolizin-7-yl)-2-ethylpyrrolo[3,2-b]pyridine 5-(3-bromophenoxy)carbonylamino-3-(1,2,3,4,5,8-hexahydroindolizin-7-yl)pyrrolo[3,2-b]pyridine 5-(acetyl)amino-3-(1,4,5,6,7,8,9-heptahydroquinolizin-2-yl)pyrrolo[3,2-b]pyridine 5-(butyroyl)amino-3-(1-azabicyclo[5.4.0]undec-3-en-4-yl)pyrrolo[3,2-b]pyridine 5-(pentanoyl)amino-3-(1,2,3,4,5,8-hexahydroindolizin-7-yl)pyrrolo[3,2-b]pyridine glycollate 5-(cyclooctylcarbonyl)amino-3-(1,4,5,6,7,8,9-heptahydroquinolizin-2-yl)pyrrolo[3,2-b]pyridine 5-(4-phenylbutanoyl)amino-3-(1-azabicyclo[5.4.0]undec-3-en-4-yl)pyrrolo[3,2-b]pyridine 5-(phenoxyacetyl)amino-3-(1,2,3,4,5,8-hexahydroindolizin-7-yl)pyrrolo[3,2-b]pyridine 5-benzoylamino-3-(1-azabicyclo[5.4.0]undec-3-en-4-yl)pyrrolo[3,2-b]pyridine 5-(4-fluorobenzoyl)amino-3-(1,2,3,4,5,8-hexahydroindolizin-7-yl)pyrrolo[3,2-b]pyridine fumarate 5-(4-fluorobenzoyl)amino-3-(1,4,5,6,7,8,9-heptahydroquinolizin-2-yl)pyrrolo[3,2-b]pyridine 5-(2-thienoyl)amino-3-(1,2,3,4,5,8-hexahydroindolizin-7-yl)pyrrolo[3,2-b]pyridine 5-(2-furoyl)amino-3-(1-azabicyclo[5.4.0]undec-3-en-4-yl)pyrrolo[3,2-b]pyridine 5-(4-phenylbutanoyl)amino-3-(octahydro-2H-quinolizin-2-yl)pyrrolo[3,2-b]pyridine 5-(3-furoyl)amino-3-(1-azabicyclo[5.4.0]undecan-4-yl)pyrrolo[3,2-b]pyridine 5-(3-furoyl)amino-3-(octahydroindolizin-7-yl)pyrrolo[3,2-b]pyridine 5-(3-furoyl)amino-3-(octahydro-2H-quinolizin-2-yl)pyrrolo[3,2-b]pyridine The compounds of the invention may be prepared by procedures well known in the art. Those compounds where Y is hydrogen, hydroxy, amino, halo, or —NR$^5$C(O)R$^{10}$ may be prepared by reacting appropriately substituted 1H-indoles, pyrrolo[3,2-b]pyridines, benzofurans or benzothiophenes with compounds of Formula (A). This chemistry is illustrated in Synthetic Scheme I where Z is hydrogen, hydroxy, benzyloxy, nitro, halo, amino, or —NR$^5$C(O)R$^{10}$, Z$^1$ is hydrogen, hydroxy, halo, amino, or —NR$^5$C(O)R$^{10}$, and n and R are as defined supra.

Synthetic Scheme I

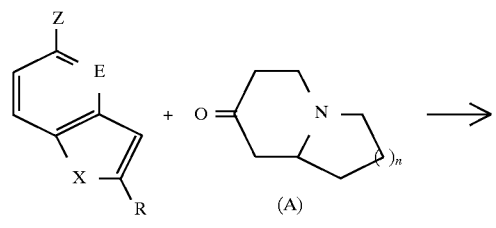

-continued
Synthetic Scheme I

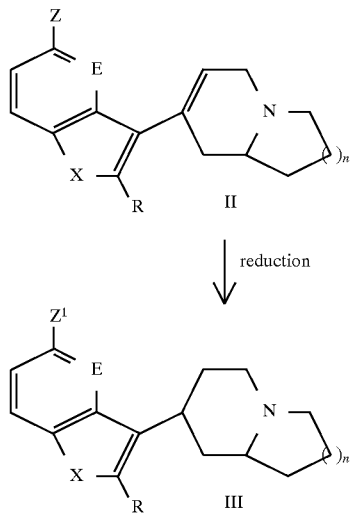

The indoles, pyrrolo[3,2-b]pyridines, benzofurans, or benzothiophenes can be condensed with a compound of Formula (A) in the presence of a suitable base to give the corresponding 3-(1,2,3,4,5,8-hexahydroindolizin-7-yl), 3-(1,4,5,6,7,8,9-heptahydroquinolizin-2-yl), or 3-(1-azabicyclo[5.4.0]undec-3-en-4-yl)-1H-indoles, -pyrrolo[3,2-b]pyridines, -benzofurans, or -benzothiophenes of Formula II. The indoles, pyrrolo[3,2-b]pyridines, or the 2-alkylbenzofurans or benzothiophenes and about 1.3 equivalents of a compound of Formula (A) are added to a solution of an excess of base, typically sodium or potassium hydroxide, in a lower alkanol, typically methanol or ethanol, and the reaction refluxed for 0.25 to 24 hours. The resulting compounds of Formula II may be isolated from the reaction mixture by the addition of water. Compounds which precipitate may be isolated directly by filtration while others may be extracted by adjusting the pH of the solution and extracting with a water immiscible solvent such as ethyl acetate or dichloromethane. The compounds recovered may be used directly in subsequent steps or first purified by silica gel chromatography or recrystallization from a suitable solvent.

The benzofuran or benzothiophene compounds of Formula II or III where R is hydrogen and Z is other than bromo or iodo are prepared by selective bromination of a suitable benzofuran or benzothiophene with bromine in acetic acid. The reaction is typically performed at about 50° C. for about 4 hours. The volatiles are then removed under reduced pressure and the residue is subjected to an extractive workup under basic conditions. The resulting 3-bromo-benzothiophene or benzofuran in diethyl ether is then treated with an alkyl lithium, typically n-butyl lithium, in the same solvent, at −78° C. to affect a halogen metal exchange. After stirring at this temperature for about 1 hour, the reaction mixture is treated with an equivalent of an appropriate compound of Formula (A). Once the addition of the compound of Formula (A) is complete, the reaction mixture is stirred at −78° C. for an additional 3 hours. It is critical to maintain the reaction mixture at this temperature to avoid equilibration of the anion to the 2-position of the benzofuran or benzothiophene ring. The reaction mixture is then allowed to warm to −20° C. over about 50 minutes. An excess of base, typically sodium or potassium hydroxide, in a lower alkanol, typically methanol or ethanol is then added and the reaction refluxed for 0.25 to 24 hours. The resulting compounds of Formula II may be isolated and purified as described supra.

Those benzofuran and benzothiophene compounds of the invention where Y is bromo or iodo and R is hydrogen may be accessed by subjecting the corresponding 5-amino derivative to Sandmeyer reaction conditions.

The skilled artisan will appreciate that the 5-bromo compounds of the invention may be converted to the corresponding 5-iodo compounds via halogen metal exchange described supra, followed by the addition of elemental iodine.

The compounds of Formula II may be used to prepare other compounds of the invention or, if desired, may be hydrogenated over a precious metal catalyst, such as palladium on carbon, to give the corresponding 3-(octahydroindolizin-7-yl), 3-(octahydro-2H-quinolizin-2-yl), or 3-(1-azabicyclo[5.4.0]-undecan-4-yl)-1H-indoles, -pyrrolo[3,2-b]pyridines, -benzofurans, or -benzothiophenes (F). When Z is bromo, a hydrogenation catalyst such as sulfided platinum on carbon, platinum oxide, or a mixed catalyst system of sulfided platinum on carbon with platinum oxide is used to prevent hydrogenolysis of the 5-bromo substituent during reduction of the hexahydroindolizinyl, heptahydroquinolizinyl, or azabicyclo[5.4.0]undecenyl double bond. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0°–60° C., preferably at ambient temperature to 40° C., for 1 hour to 3 days. Additional charges of hydrogen may be required to drive the reaction to completion depending on the specific substrate. The compounds of Formula III prepared in this manner are isolated by removal of the catalyst by filtration followed by concentration of the reaction solvent under reduced pressure. The product recovered may be used directly in a subsequent step or further purified by chromatography, or by recrystallization from a suitable solvent. The skilled artisan will appreciate that these hydrogenation conditions typically reduce aromatic nitro groups to the corresponding amines.

As an alternative to hydrogenation, the compounds of Formula II may be converted to the corresponding compounds of Formula III by treatment with trifluoroacetic acid/triethylsilane if desired. The compound of Formula II is dissolved in trifluoroacetic acid to which is added an excess, 1.1–10.0 equivalents, of triethylsilane. The reaction mixture is stirred at about ambient temperature for from about 1 to about 48 hours at which time the reaction mixture is concentrated under reduced pressure. The residue is then treated with 2N sodium or potassium hydroxide and the mixture extracted with a water immiscible solvent such as dichloromethane or diethyl ether. The resultant compounds of Formula III can be purified by column chromatography if necessary or desired.

The compounds of Formula (A) required for the preparation of the compounds of the invention may be prepared from methylvinyl ketone and an appropriate aminodialkylacetal or -cyclic acetal according to the procedures found in *Tet. Let.*, 24, 3281 (1983), and *J.C.S. Perk. I,* 447 (1986). These acetals are generally commercially available or can be synthesized by well known methods in the art from their corresponding commercially available 4-substituted butanals or 5-substituted pentanals. This chemistry is illustrated in Synthetic Scheme II, where m is 3,4, or 5, L and $L^1$ are independently $C_1$–$C_4$ alkyl, or L and $L^1$ taken together with the oxygen atom to which they are attached form a 5 or 6 membered cyclic acetal, and n is as defined supra.

Synthetic Scheme II

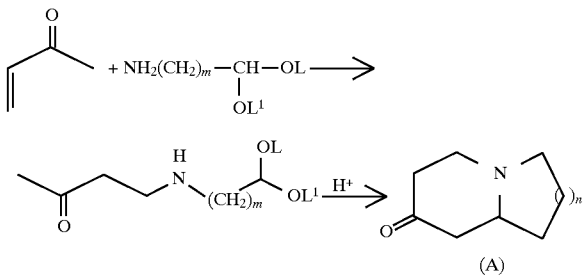

(A)

The compounds of Formula (A) are prepared by acid treatment of the addition product of methyl vinyl ketone and an aminobutanal, pentanal, or hexanal dialkylacetal, such as diethyl acetal. The reaction is performed by first dissolving the appropriate aminoacetal in an appropriate solvent, typically diethyl ether at 0° C., and then adding approximately 1.7 equivalents of methyl vinyl ketone. Typically the reaction is allowed to stir at 0° C. for approximately 2 hours before acidification by addition of, or extraction with, aqueous hydrochloric acid. Typically, the organic layer is removed before heating the aqueous layer to approximately 100° C. for 1 hour. The resulting 7-octahydroindolizinone, 2-octahydro-2H-quinolizinone, or 4-(1-azabicyclo[5.4.0] undecan)ones (A) may be isolated from the reaction mixture by adjusting the pH of the solution to alkaline and extracting with a water immiscible solvent such as ethyl acetate or dichloromethane. The compounds recovered may be used directly in subsequent steps or first purified by silica gel chromatography or vacuum distillation.

Compounds of Formula (A) prepared as described in Synthetic Scheme II are racemic and, if used as described in Synthetic Scheme I, will produce racemic compounds of the invention. Compounds of the invention that are optically enhanced in one enantiomer can be obtained by resolving the compounds of Formula (A) before use of said compounds in the chemistry described in Synthetic Scheme I. Methods of resolving enantiomeric compounds of this type are well known in the art. For example, resolution can be achieved by use of chiral chromatography. Furthermore, racemic compounds of Formula (A) can be converted to their corresponding diastereomeric mixture of salts by reaction with a chiral tartaric acid. The diastereomers can then be separated and purified by recrystallization. Once separated, the salts can each be converted back to the chiral free base compounds of Formula (A) by reacting the salts with an aqueous base, such as sodium hydroxide, then extracting the mixture with a common organic solvent. The optical purity in resolved compounds of Formula (A) is maintained while undergoing the chemistry described in this application to afford optically pure compounds of the invention.

Compounds of the invention where X is N—H and E is —CH— are substituted 1H-indoles. While the simple indoles (those which are 2,5-disubstituted or 5-monosubstituted) required for the preparation of these compounds are generally commercially available, their preparations are described in Robinson, *The Fischer Indole Synthesis*, Wiley, New York (1983); Hamel, et al., *Journal of Organic Chemistry*, 59, 6372 (1994); and Russell, et al., *Organic Preparations and Procedures International*, 17, 391 (1985).

Compounds of the invention where X is O are substituted benzofurans. Compounds of the invention where X is S are substituted benzothiophenes. These compounds can be derived from the corresponding benzofurans and benzothiophenes respectively (V), which may be prepared by the procedure described in Synthetic Scheme III, where halo is chloro or bromo, D is O or S, $Z^2$ is hydrogen, hydroxy, amino, nitro, halo, or Pg. Pg is an oxygen or nitrogen protected with an appropriate protecting group selected from Green, *Protective Groups in Organic Synthesis,* 2nd Ed., Wiley Interscience, 1991, and R is as defined supra.

Synthetic Scheme III

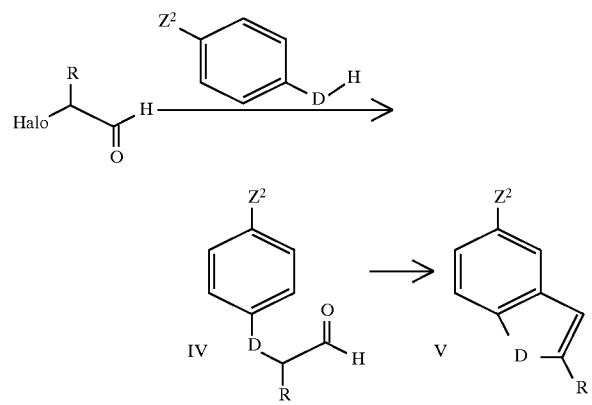

An α-halo-acetaldehyde, optionally protected as the corresponding acetal, is reacted with an appropriately substituted, commercially available, phenol or thiophenol under standard alkylating conditions to provide the corresponding ether or thioether IV. This ether or thioether is converted to the corresponding benzofuran or benzothiophene V by heating in the presence of an acid, typically polyphosphoric acid or sulfuric acid.

The skilled artisan will appreciate that where $Z^2$ is Pg the protecting group at the 5-position may be hydrolyzed during the cyclization step to provide the desired unprotected benzothiophenes or benzofurans V. Alternatively, the protecting group may be removed in a separate deprotection step if necessary or desired.

The α-halo aldehydes, or corresponding acetals, required for the preparation of the compounds of the invention are either commercially available or may be prepared from the corresponding acids or acid halides by methods well known to one of ordinary skill in the art. This chemistry is reviewed by Larock (*Comprehensive Organic Transformations*, pages 378–379, VCH Publishers, New York, 1989).

The compounds of the invention where E is —CH— and Y is —S—$R^1$ may be prepared from the corresponding 5-bromo or 5-iodo compounds as illustrated in Synthetic Scheme IV, where A, B, n, R and $R^1$ are as defined supra.

Synthetic Scheme IV

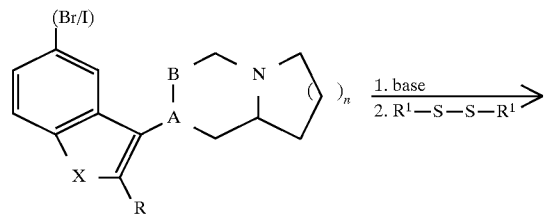

-continued
Synthetic Scheme IV

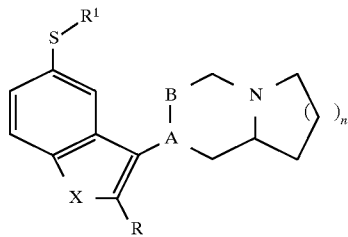

The 5-bromo or 5-iodo-1H-indole in a suitable aprotic solvent, such as diethyl ether or tetrahydrofuran, is cooled to about 0° C. and treated with potassium hydride to deprotonate the indole nucleus at the 1-position. While other hydrides are useful for this deprotonation, the resultant potassium salt is more soluble in typical reaction solvents. This anion mixture, or the 5-bromo- or 5-iodo- benzothiophene or benzofuran compound, dissolved in a suitable aprotic solvent, is then cooled to about −78° C. and halogen-metal exchange effected by the addition of two equivalents of t-butyllithium. To this dianion (X is N—H) or monoanion (X is O or S) solution are then added an appropriate disulfide and the reaction mixture allowed to warm to ambient temperature. The compound of the invention is isolated by treating the reaction mixture with aqueous base, such as sodium or potassium hydroxide, and then extracting with a water immisible solvent such as diethyl ether or dichloromethane. The reaction product may then be purified by column chromatography.

Compounds of the invention where E is —CH— and Y is —C(O)$R^2$ or —C(O)N$R^3R^4$ are prepared from the corresponding 5-bromo- or 5-iodo compounds as illustrated in Synthetic Scheme V, where A, B, n, R, $R^2$, $R^3$ and $R^4$ are as defined supra.

Synthetic Scheme

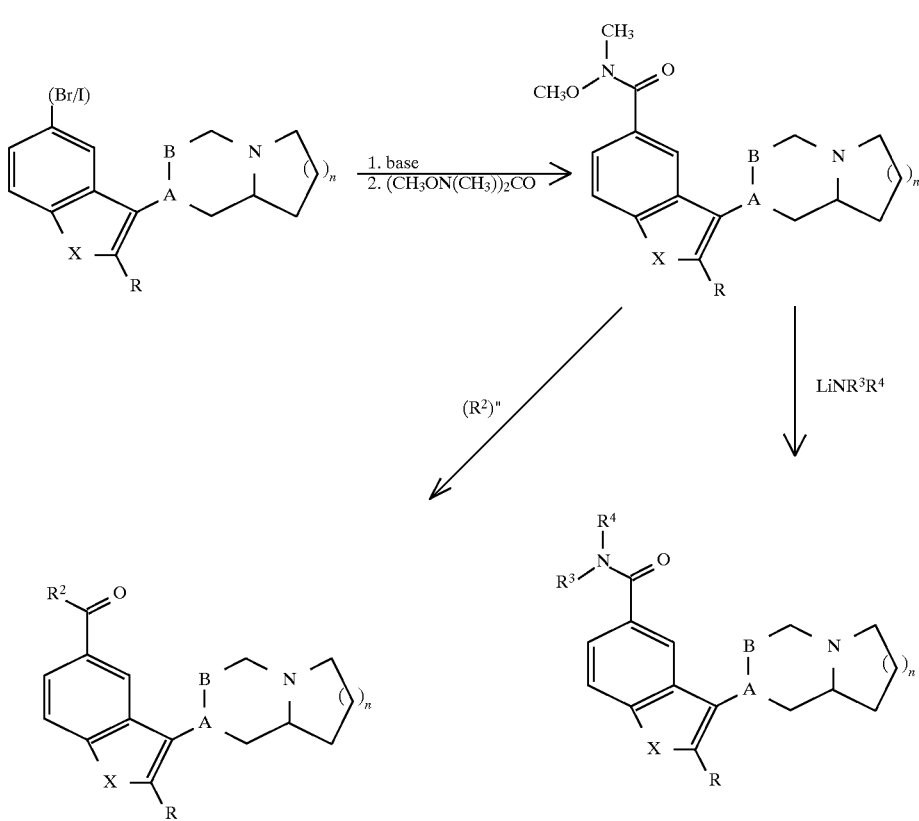

V

The dianion (X is N—H) or monoanion (X is O or S) solution is prepared as previously described and is then treated with N,N'-dimethyl-N,N'-dimethoxyurea. The resulting Weinreb amide is isolated by treating the reaction mixture with aqueous base, such as sodium or potassium hydroxide, and then extracting with a water immisible solvent such as diethyl ether or dichloromethane. The reaction product may then be purified by column chromatography.

Compounds of the invention where Y is —C(O)R$^2$ are prepared by reacting a solution of the Weinreb amide in a suitable solvent, such as diethyl ether or tetrahydrofuran, at about 0° C., with an appropriate reagent such as an aryl- or alkyllithium or an alkyl or aryl Grignard reagent. These reagents are either commercially available or may be prepared by methods well known to one of ordinary skill in the art. The aryl- or alkyllithium reagents are conveniently prepared by treating an appropriate aryl or alkyl halide with n-butyl-lithium. The aryl or alkyl Grignard reagents may be prepared by treating an appropriate aryl or alkyl halide with magnesium. The compounds of interest may be isolated by aqueous work-up followed by extraction into a water immiscible solvent such as diethyl ether or dichloromethane, and then purified by chromatography, or by recrystallization from a suitable solvent.

Compounds of the present invention where X is NH and E is N are pyrrolo[3,2-b]pyridines. The requisite 5-substituted pyrrolo[3,2-b]pyridines necessary for the preparation of the compounds of the present invention may be prepared as described in Synthetic Scheme VI where Z$^3$ is halo, C$_1$-C$_4$ alkoxy.

Synthetic Scheme VI

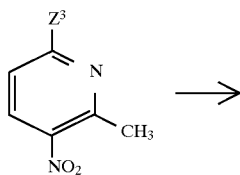

Synthetic Scheme VI
-continued

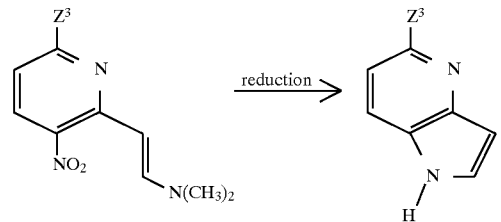

The 2-methyl-3-nitro-6-substituted pyridine may be reacted with either dimethylformamide dimethylacetal in dimethylformamide or tris(dimethylamino)methane in toluene at elevated temperature to prepare the corresponding iminoenamine. Where Z$^3$ is C$_1$-C$_4$ alkoxy, the iminoenamine in a lower alkanol, typically ethanol, or a mixture of the lower alkanol and tetrahydrofuran, is then hydrogenated over Raney nickel or a precious metal catalyst, typically either platinum or palladium on carbon, to provide the appropriate 5-(C$_1$-C$_4$ alkoxy)pyrrolo[3,2-b]pyridine. Where Z$^3$ is halo, the iminoenamine is reacted with metallic iron in toluene/-acetic acid to provide the desired 5-halopyrrolo[3,2-b]-pyridine. The 5-substituted pyrrolo[3,2-b]pyridines may be purified by recrystallization or chromatography as necessary or desired prior to use in the preparation of the compounds of the present invention.

The 6-substituted 3-nitro-2-picolines required to prepare the corresponding 5-substituted-pyrrolo[3,2-b]pyridines are either commercially available or may be prepared by methods well known to the skilled artisan.

The 5-aminopyrrolo[3,2-b]pyridines required to prepare certain compounds of the present invention may be prepared as described in Synthetic Scheme VII where A, B and n are as previously defined. The skilled artisan will appreciate that while the dimethyaminomethylimino substituents represented in Synthetic Scheme VII are drawn as existing in the "trans" form, that the actual products may be either "cis", "trans", or a mixture thereof.

Synthetic Scheme VII

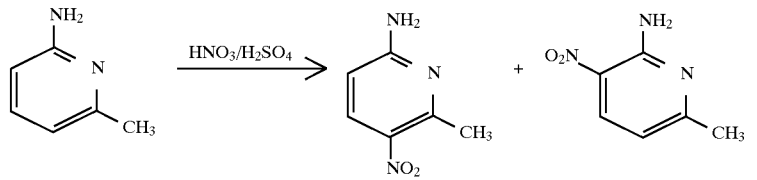

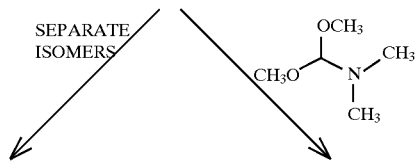

-continued
Synthetic Scheme VII

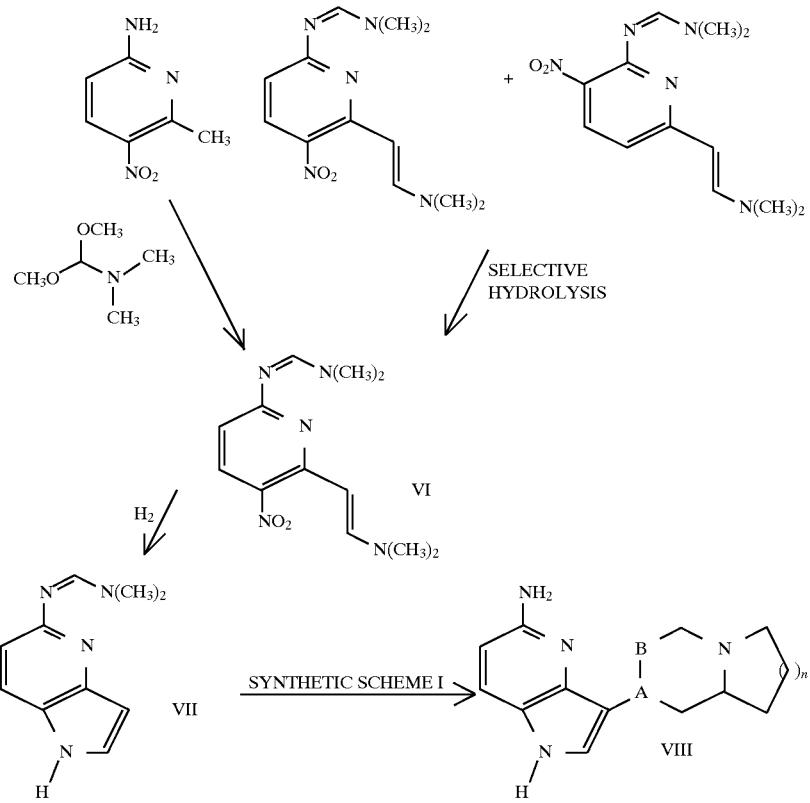

The nitration is performed by adding an equivalent of 90% nitric acid dissolved in an equal volume of concentrated sulfuric acid which has been precooled 0° C. to a solution of 6-amino-2-picoline (6-amino-2-methylpyridine) in five volumes (relative to volume of nitric acid solution) of concentrated sulfuric acid at −6° C. The nitric acid solution is added at a rate to maintain the temperature of the reaction mixture at about −2° C. The reaction mixture is stirred at about 0° C. for one hour and is then allowed to warm to about 10° C. over an hour. The temperature of the reaction mixture is maintained at about 10° C. for one hour and is then allowed to warm to about 20° C. over an hour. The reaction mixture is maintained at about 20° C. for 2 hours. The reaction mixture is then poured over ice, made basic (pH about 9) by the addition of an appropriate hydroxide base, typically potassium, sodium, or ammonium hydroxide, maintaining the temperature at about 20° C. by the addition of ice as needed. The resulting slurry is filtered, washed with water, and dried to provide a 2:1 mixture of 3-nitro-:5-nitro-6-amino-2-picoline.

The undesired 5-nitro-6-amino-2-picoline isomer may be removed by steam distillation, sublimation, or by fractional crystallization from a suitable solvent, preferably toluene. The desired 3-nitro-6-amino-2-picoline is then reacted with dimethylformamide dimethylacetal or tris(dimethylamino)-methane in a suitable solvent, typically dimethylformamide.

Once the reaction is complete the reaction mixture is treated with either water or isopropanol to precipitate the desired intermediate VI, which is isolated by filtration. Alternatively, intermediate VI may be prepared by directly subjecting the mixture of nitration isomers previously described to dimethylformamide dimethylacetal or tris(dimethylamino) methane. Treatment of the resulting reaction mixture with water results in the precipitation of intermediate VI which may be isolated by filtration.

Intermediate VI may then be hydrogenated in a lower alkanol, typically ethanol, in the presence of a palladium catalyst, typically 10% palladium on carbon. Once hydrogenation is complete, the reaction mixture is filtered and the filtrate concentrated under reduced pressure. The desired 5-(dimethylaminomethylimino)pyrrolo[3,2-b]pyridine VII may be used as recovered in subsequent reactions or first purified by slurry washing or by silica gel chromatography as necessary or desired. Reacting 5-(dimethylaminomethylimino)-pyrrolo[3,2-b]pyridine VII as described in Synthetic Scheme I provides the required intermediate 5-aminopyrrolo[3,2-b]pyridines VIII.

Alternatively, the intermediate VIII may be prepared by the procedure described in Synthetic Scheme VIII.

Synthetic Scheme VIII

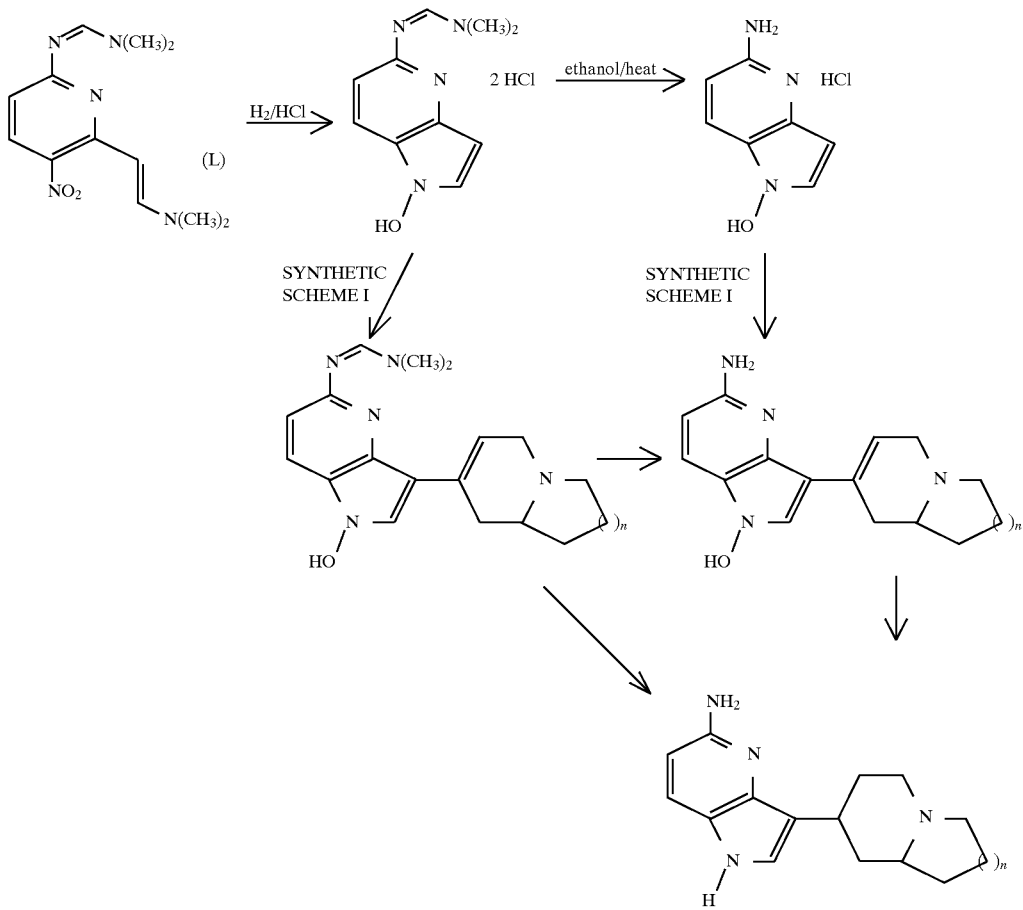

Intermediate VI is hydrogenated in methanol containing hydrogen chloride in the presence of a palladium catalyst, typically 10% palladium on carbon. The resulting 1-hydroxy-5-(dimethylaminomethaneimino)pyrrolo[3,2-b]pyridine dihydrochloride is isolated by filtration of the reaction mixture and may be further purified and removed from catalyst by recrystallization. The amidine functionality at the 5-position of the pyrrolo[3,2-b]pyridine may be removed to provide the corresponding amine by heating the amidine substrate in ethanol under acidic conditions or under neutral hydrogenation conditions. The amidine functionality at the 5-position may be removed either prior or subsequent to reaction with an appropriate ketone. Regardless of when the amidine functionality is removed, the 1-hydroxy substituent is removed by hydrogenation in a lower alkanol, typically methanol, in the presence of a palladium catalyst, typically 10% palladium on carbon.

Pyrrolo[3,2-b]pyridines of the invention where Y is $C_1$–$C_4$ alkoxy, while useful 5-$HT_{1F}$ agonists, are also useful intermediates for the preparation of other compounds of the invention as illustrated in Synthetic Scheme IX where A, B, n, $R_3$, and $R^4$ are as previously defined.

Synthetic Scheme IX

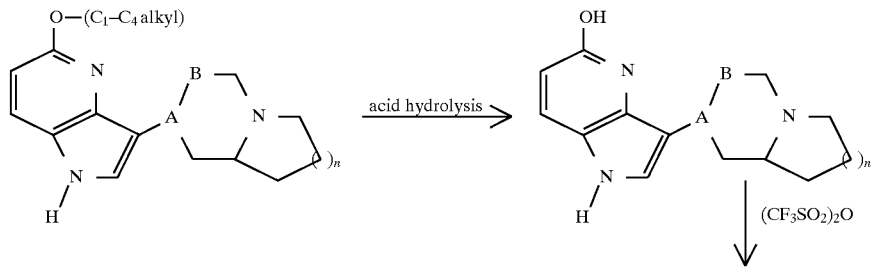

-continued
Synthetic Scheme IX

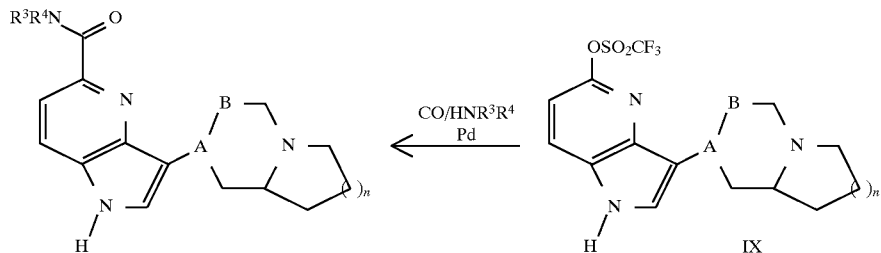

An appropriate 5-alkoxypyrrolo[3,2-b]pyridine is heated with an aqueous acid, typically hydrobromic acid, to prepare the corresponding 5-hydroxypyrrolo[3,2-b]pyridine. This 5-hydroxy derivative is then treated with trifluoromethanesulfonic anhydride in a suitable solvent, typically pyridine, to provide the corresponding triflate of Formula IX. The triflate of Formula IX is then subjected to palladium catalyzed carbonylation conditions in the presence of a suitable amine to provide the corresponding amide. A mixture of the triflate, palladium(II) acetate, 1,1'-bis(diphenylphosphine) ferrocene, a proton scavenger such as triethylamine or potassium carbonate, and a suitable amine are combined in a suitable solvent, typically acetonitrile or dimethylformamide. The mixture is saturated with carbon monoxide and is then heated until the reaction is complete. The corresponding amides are typically isolated by a standard extractive workup and purified by crystallization or chromatography. The skilled artisan will appreciate that the 5-hydroxypyrrolo[3,2-b]pyridine is a tautomeric mixture with the corresponding 5-keto form. The compound may exist completely in the hydroxy form, completely in the keto form, or as some tautomeric mixture.

Pyrrolo[3,2-b]pyridines of the invention where Y is —C(O)R² and R² is N-methyl-N-methoxyamino, while useful 5-HT$_{1F}$ agonists, are also useful intermediate Weinreb amides for the preparation of other compounds of the invention. These Weinreb amides may be treated with an appropriate an aryl- or alkyllithium or an alkyl or aryl Grignard reagent as described in Synthetic Scheme V.

The 5-hydroxypyrrolo(3,2-b)pyridines may also be treated with an appropriate halogenating agent, for example, phosphorus trihalide, phosphorus oxyhalide, or thionyl halide to prepare the corresponding 5-halopyrrolo[3,2-b] pyridine. These 5-halo compounds may then be treated with the anion of an appropriate thiol to provide the pyrrolo[3,2-b]pyridines of the present invention where Y is —S—R¹.

The compounds of the invention where Y is —NR⁵SO₂R⁶ may be prepared by modifying an appropriate 5-aminoindole, pyrrolo[3,2-b]pyridine, benzofuran, or benzothiophene as described in Synthetic Scheme X. When R⁵ is to be hydrogen, the 5-amino compound is reacted with an appropriate sulfonyl halide or anhydride to give the corresponding sulfonamide. When R⁵ is to be lower alkyl, however, the 5-amino compound is first acylated, and then reduced with an appropriate hydride reducing agent. Alternatively, the 5-amino compound may be reductively alkylated with an appropriate aldehyde or ketone in the presence of a suitable hydride reducing agent to give the appropriately substituted 1H-indole, pyrrolo[3,2-b]pyridine, benzofuran, or benzothiophene. These compounds are then reacted with a sulfonyl halide or anhydride to give the corresponding sulfonamide. This chemistry is illustrated below, where M is methoxy, ethoxy, methyl, ethyl, propyl, or isopropyl, LG is chloro or bromo, and n, E, X, R, R⁵, and R⁶ are as defined supra.

Synthetic Scheme X

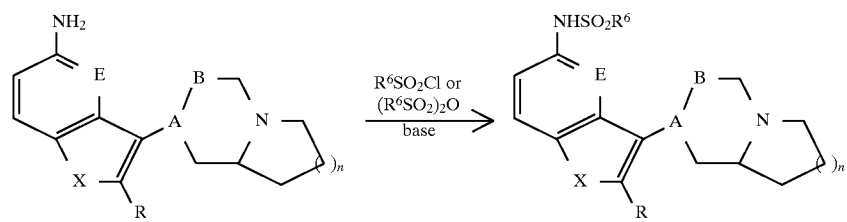

R⁵ = lower alkyl

-continued
Synthetic Scheme X

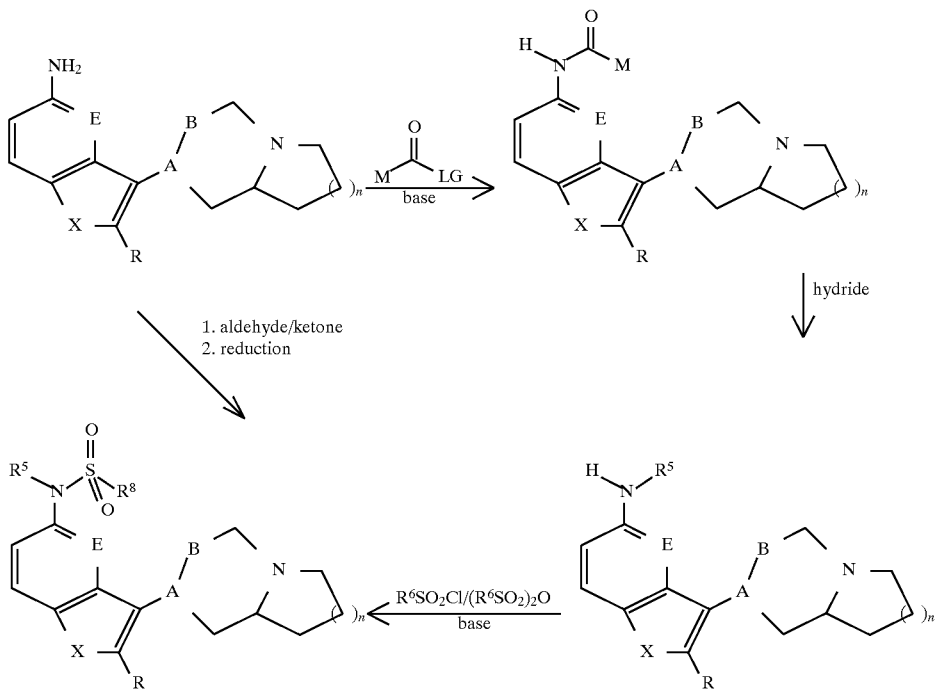

When $R^5$ is to be lower alkyl, a solution of a 5-amino-indole, pyrrolo[3,2-b]pyridine, benzofuran, or benzothiophene in a suitable solvent, such as tetrahydrofuran, dioxane, or diethyl ether, at a temperature from about ambient to about 0° C., is reacted with a compound of structure M-C(O)-halo in the presence of a suitable base such as pyridine or triethylamine. The resultant compound is isolated by dilution of the reaction mixture with water and extraction with a water immiscible solvent such as dichloromethane. This acylated product may either be purified chromatographically or used directly in the subsequent step. The acylated product is then dissolved in a suitable solvent, such as tetrahydrofuran or diethyl ether, at a temperature from about ambient to about 0° C., and is treated with a suitable hydride reducing agent such as diborane or lithium aluminum hydride. The reaction is stirred from 1 to 24 hours and is then treated with an aqueous solution of sodium sulfate. The resultant suspension is filtered, and the filtrate concentrated under reduced pressure. The product may be used for further reaction as is, purified by chromatography, or recrystallized from a suitable solvent.

Alternatively, a solution of a 5-amino- indole, pyrrolo[3,2-b]pyridine, benzofuran, or benzothiophene in a solvent suitable for the azeotropic removal of water, such as toluene, benzene or cyclohexane, is reacted at reflux with an appropriate aldehyde or ketone, such as formaldehyde, acetaldehyde, propanal, butanal or acetone, in the presence of 0.1–10% of a proton source such as p-toluenesulfonic acid. When the reaction is complete the volatiles are removed under reduced pressure and the residue redissolved in an alkanol such as methanol or ethanol. This solution is then subjected to hydrogenation conditions, or is treated with an appropriate hydride reducing agent, such as sodium borohydride or, preferably, sodium cyanoborohydride in the presence of an anhydrous acid such as hydrogen chloride. The reaction is then diluted with water, treated with base and extracted into a water immiscible solvent such as dichloromethane. The resulting product may be used as is for further reaction, purified by chromatography, or crystallized from a suitable solvent. This product is now treated with a commercially available $R^6$-sulfonyl halide or $R^6$-sulfonic anhydride as previously described to give the required sulfonamides.

Compounds of the invention where Y is —NHC(Q) $NR^7R^8$ —NHC(O)$OR^9$, or —$NR^5$C(O)$R^{10}$ are prepared by reacting an appropriate 5-amino- indole, pyrrolo[3,2-b] pyridine, benzofuran or benzothiophene with a suitable electrophile. These reactions are illustrated in Synthetic Scheme XI, where E, n, A, B, R, $R^5$, $R^7$, $R^8$, $R^9$, and $R^{10}$ are as previously described.

Synthetic Scheme XI

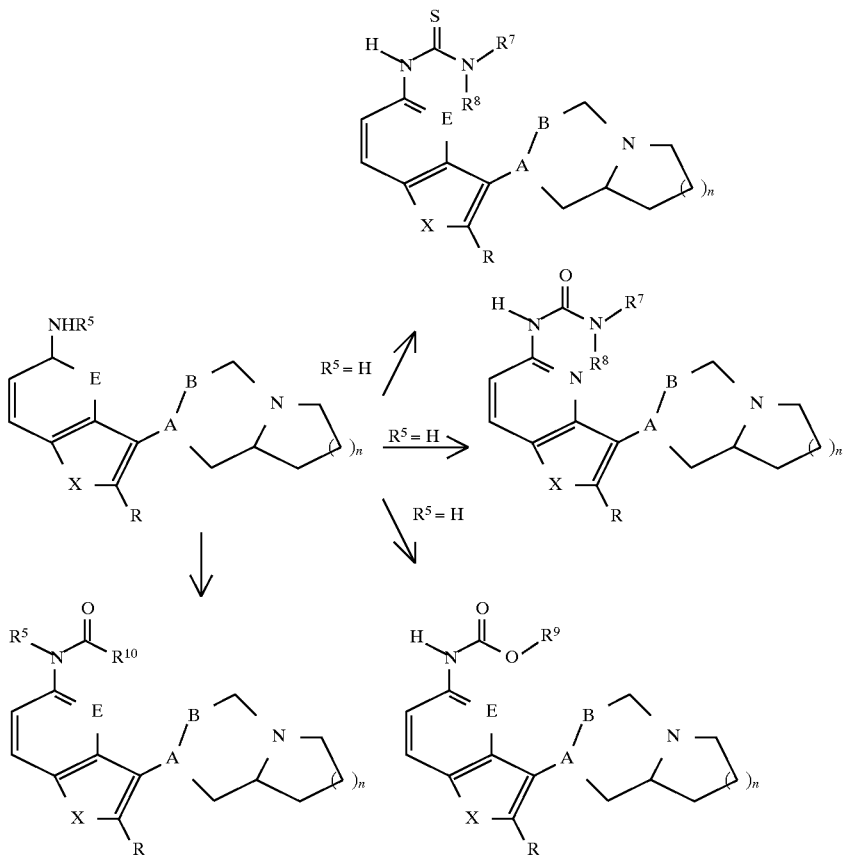

Compounds of the invention where Y is —NHC(Q)NR$^7$R$^8$ are prepared by treating a solution of the appropriate 5-amino compound in a suitable solvent, such as chloroform or dichloromethane, with an appropriate isocyanate, isothiocyanate, thiocarbamoyl chloride, carbamoyl chloride or carbamoyl bromide. Appropriate carbamoyl chlorides and thiocarbamoyl chlorides are available by treating an amine of formula HNR$^7$R8 with phosgene or thiophosgene, respectively. When a thiocarbamoyl chloride, carbamoyl chloride or carbamoyl bromide is used, the reactions are performed in the presence of a suitable base. Suitable bases include amines typically used as acid scavengers, such as pyridine or triethylamine, or commercially available polymer bound bases such as polyvinylpyridine. If necessary, an excess of the isocyanate, isothiocyanate, thiocarbamoyl chloride, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds of the invention which are ureas may be converted into the corresponding thiourea by treatment with [2,4-bis(4-methoxyphenyl)- 1,3-dithia-2,4-diphosphetane-2,4-disulfide] (Lawesson's Reagent) or phosphorus pentasulfide.

Compounds of the invention where Y is —NHC(O)OR$^9$ are prepared by reacting the appropriate 5-amino compound with an appropriately substituted chloroformate in the presence of a suitable amine under the conditions described in the previous paragraph. Likewise, compounds of the invention where Y is —NR$^5$C(O)R$^{10}$ are prepared by reacting the appropriate 5-amino compound with an appropriate carboxylic acid chloride, bromide or anhydride, optionally in the presence of an acylation catalyst such as dimethylaminopyridine, in the presence of a suitable base, such as those described supra.

Alternatively, compounds of the invention where Y is —NR$^5$C(O)R$^{10}$ are prepared by reacting the appropriate 5-amino compound with an appropriate carboxylic acid halide, carboxylic acid anhydride, or a carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters,* 34(48), 7685 (1993)) and is very useful for the preparation of the compounds of the present invention. The product from these reactions is isolated and purified as described above.

The skilled artisan will appreciate that the order in which the steps are performed to prepare the compounds of the present invention is not important in many cases. For example, the manipulations performed at the 5 position of compounds discussed and shown in Schemes IV–V and IX–XI may be performed prior to reaction with a compound of Formula (A) as is illustrated in Synthetic Scheme I. Additionally, the 3-( 1,2,3,4,5,8-hexahydroindolizin-7-yl), 3-(1,4,5,6,7,8,9-heptahydroquinolizin-2-yl), and 3-(l-azabicyclo[5.4.0]undec-3-en-4-yl)-1H-indoles, pyrrolo[3,2-b]pyridines, benzofurans, and benzothiophenes may also be reduced to the corresponding 3-(octahydroindolizin-7-yl), 3-(octahydro-2H-quinolizin-2-yl), and 3-(l-azabicyclo [5.4.0]undecan-4-yl)-1H-indoles, -pyrrolo[3,2-b]pyridines, -benzofurans, and -benzothiophenes at any convenient point in the synthetic sequence. These variations are made apparent in the following Preparations and Examples.

PREPARATION I

7-Octahydroindolizinone

The methylvinyl ketone (18.0 g, 256 mmol) was added dropwise to a solution of the 4,4-diethoxybutylamine (24.8 g, 154 mmol) in diethyl ether at 0° C. and stirred for one hour. The reaction was allowed to warm to room temperature and stir for 2 hours. The reaction was poured into 350 ml of 2N hydrochloric acid and the layers were separated. The aqueous layer was heated on a steam bath for 1 hour and then allowed to stir at 40° C. for 18 hours. The reaction was made basic with a sodium hydroxide solution and then extracted with methylene chloride. The extracts were dried over sodium sulfate and concentrated to give 20 g of an orange oil. This oil was distilled in vacuo at 74°–84° C./5 mmHg to give 6.68 g of racemic product. (31%). MS(FD) (m/e): 139.

PREPARATION II

Resolution of racemic 7-octahydroindolizinone
Preparation of the (+)-ditoluoyl tartaric acid salts of 7-octahydroindolizinone The (+)-ditoluoyl tartaric acid monohydrate (19.7 g, 49 mmol) was dissolved in 100 ml of warm methanol and the racemic 7-octahydroindolizinone (6.86 g, 49 mmol) in 25 ml of methanol was added. The reaction was thoroughly mixed and allowed to stand at room temperature for about 18 hours. No precipitate had formed so the material was concentrated by boiling and ethyl acetate was added. At the point where solid began to form, the reaction was cooled to room temperature and a precipitate formed. This material was collected by filtration. The filter cake was recrystallized twice from methanol/acetonitrile to give 7.87 g a product which was approximately a 2:1 mixture of diastereomers. (31%).

Calculated for $C_8H_{13}NO.C_{20}H_{18}O_8$: Theory: C, 63.99; H; 5.95; N, 2.67. Found: C, 63.92; H, 5.98; N, 2.55. OR(DMSO, C=1.0) (a): 589 nm 72.6°; 365 nm 393.4°.
Preparation of the chiral 7-octahydroindolizinone free amine The (+)-ditoluoyl tartaric acid salt of 7-octahydroindolizinone (7.42 g, 14 mmol) from Step 1 was suspended in methylene chloride/0.5M sodium hydroxide solution and stirred until no solid was visible. The layers were separated and the aqueous layer extracted with methylene chloride. The combined organic extracts were dried over sodium sulfate and concentrated to give 2.00 g of a light yellow oil. (100%).

MS(FD) (m//e): 139.

PREPARATION III

2-Octahydro-2H-quinolizinone
Preparation of 2-(3-cyanopropyl)-1.3-dioxolane

In a flame dried flask fitted with a nitrogen inlet, magnetic stirrer, and oil bath was dissolved the 2-(3-chloropropyl)-1,3-dioxolane (25.4 g, 169 mmol) in 70 ml of dimethylsulfoxide. Sodium cyanide (9.1 g, 186 mmol) in 100 ml of dimethylsulfoxide was added and the mixture was heated to 80° C. for 18 hours. The reaction was cooled to room temperature then poured onto ice water and stirred for 1 hour. The mixture was extracted thoroughly with diethyl ether, testing the aqueous after each extraction by TLC for the presence of product. The ether was washed with brine, dried over sodium sulfate, and concentrated in vacuo to give a colorless oil. The oil was purified by silica gel chromatography (50/50 ethyl acetate/hexane) to give 19.2 g of product. (80.7%).

Calculated for $C_7H_{11}NO_2$: Theory: C, 59.33; H, 7.63; N, 9.87. Found: C, 59.56; H, 7.85; N, 9.92.

MS(FD+)(m/e): 142.
Preparation of 2-(4-aminobutyl)-1,3-dioxolane

To a solution of 14.5 gm (10.3 mmol) 2-(3-Cyanopropyl) -1,3-dioxolane in anhydrous ammonia and ethanol was added 5% ruthenium on aluminum oxide. The reaction mixture was hydrogenated with an initial hydrogen pressure of 100 psi at ambient temperature for 32 hours. The reaction mixture was filtered and the filtrate concentrated under reduced pressure. The residue was purified by silica gel chromatography to give 12.0 gm (80.5%) of the product.

MS(FD+)(m/e): 146.
Preparation of 2-octahydro-2H-quinolizinone

The 2-(4-aminobutyl)-1,3-dioxolane (2.45 g, 16.9 mmol) and methylvinyl ketone (2.4 ml, 28.7 mmol) were converted to product by the procedure of Preparation I to yield 100 mg. (3.85%).

MS(FD+)(m/e): 153.

PREPARATION IV 3-(1,2,3,4,5,8-Hexahydroindolizin-7-yl)-5-hydroxybenzyl-1H-indole A mixture of 5-hydroxybenzyl-1H-indole (3.69 g, 16.5 mmol) and 7-octahydroindolizinone (2.98 g, 21.5 mmol) in methanolic potassium hydroxide (10% potassium hydroxide in methanol, 50 ml) was heated to reflux for 3.5 hours. The reaction was diluted with water and the precipitate was collected by filtration. The filter cake was triturated with hot diethyl ether and filtered. The filter cake was recrystallized from methanol and dried to give 1.45 g of tan flakes. (25.8%).

Calculated for $C_{23}H_{24}N_2O$: Theory: C, 80.20; H, 7.02; N, 8.13. Found: C, 80.24; H, 7.30; N, 8.09.

PREPARATION V 3-(1,2,3,4,5,8-Hexahydroindolizin-7-yl)-5-nitro-1H-indole

The 5-nitro-1H-indole (4.48 g, 27.6 mmol) and 7-octahydroindolizinone (5.0 g, 35.9 mmol) were converted to product by the procedure of Preparation IV to yield 2.99 g. (38.5%).

Calculated for $C_{16}H_{17}N_3O_2$: Theory: C, 67.83; H, 6.05; N, 14.83. Found: C, 68.07; H, 6.27; N, 14.82.

MS(FD) (m/e) 283.

PREPARATION VI

N-(4-fluorobenzoyl)-5-amino-1H-indole

The 4-fluorobenzoyl chloride (5.2 g, 33 mmol) in 30 ml of tetrahydrofuran was added dropwise to a solution of the 5-amino-1H-indole (3.96 g, 30.0 mmol) and triethylamine (4.04 g, 40 mmol) at room temperature. The reaction was stirred for 18 hours and then poured into water. The mixture was made basic with sodium hydroxide solution then extracted with methylene chloride. The extract was dried (sodium sulfate) and concentrated. The residue was recrystallized from ethyl acetate/hexanes to give 6.37 g of product. (84%).

MP=205°–207° C.

PREPARATION VII

N-(4-fluorobenzoyl)-5-amino-benzothiophene

The title compound is obtained from 4-fluorobenzoyl chloride and 5-aminobenzothiophene by the procedure of Preparation VI.

PREPARATION VIII

N-(4-fluorobenzoyl)-5-aminobenzofuran

The title compound is obtained from 4-fluorobenzoyl chloride and 5-aminobenzofuran by the procedure of Preparation VI.

PREPARATION IX

3-Bromo-5-chlorobenzothiophene

To a solution of 0.30 gm (1.77 mMol) 5-chlorobenzothiophene 1.0 mL acetic acid was added a solution of 0.31 gm (1.95 mMol) bromine in 1.0 mL acetic acid under a nitrogen atmosphere. The reaction was heated to 50° C. for 4 hours at which time the volatiles were removed under reduced pressure. The residue was partitioned between dichloromethane and aqueous sodium bicarbonate. The phases were separated and the organics were washed with saturated aqueous sodium chloride, dried over sodium sulfate and concentrated under reduced pressure to give 0.335 gm (76%) of the title compound as a tan solid.

m.p.=85°–86° C.

MS(FD): m/e=249 (M+2)

EA: Calculated for: $C_8H_4BrClS$: Theory: C, 38.82; H, 1.63. Found: C, 39.12; H, 1.72.

PREPARATION X

N-(4-fluorobenzoyl)-5-amino-3-bromobenzothiophene

The title compound is obtained from N-(4-fluorobenzoyl)-5-aminobenzothiophene by the procedure of Preparation IX.

PREPARATION XI

N-(4-fluorobenzoyl)-5-amino-3-bromobenzofuran

The title compound is obtained from N-(4-fluorobenzoyl)-5-amino-benzofuran by the procedure of Preparation IX.

PREPARATION XII 5-(dimethylaminomethylimino)pyrrolo[3,2-b]pyridine (VII)

Nitration of 6-amino-2-picoline pb 110gm (1.02 mole) molten 6-amino-2-picoline were added dropwise to 500 mL concentrated sulfuric acid which had been precooled to −15° C. at rate to maintain the temperature of the sulfuric acid solution under 20° C. The solution was then cooled to about −6° C. and then a solution of 49 mL 90% nitric acid (1.16 mole) in 49 mL sulfuric acid precooled to about 0° C. was added dropwise over about 30 minutes, maintaining the temperature at about 0° C. The reaction mixture was stirred at about 0° C. for one hour and was then allowed to warm to about 10° C. over an hour. The temperature of the reaction mixture was maintained at about 10° C. for one hour and was then allowed to warm to about 20° C. over an hour. The reaction mixture was maintained at about 20° C. for 2 hours. The reaction mixture was poured into 8 L of ice with vigorous stirring. The reaction mixture was then adjusted to pH ~9 by the addition of 1.5 L concentrated ammonium hydroxide, maintaining the temperature of the reaction mixture at about 24° C. by the addition of ice as needed. The resulting slurry was filtered and the solid washed several times with water. The solid was dried at 70° C. under vacuum for 3 days to provide 135.4 gm (87%) of a 2:1 mixture of 3-nitro-:5-nitro-6-amino-2-picoline.

Separation of nitration isomers by sublimation 20 gm lots of the nitration mixture were sublimed twice under vacuum at 125° C. for 6 hours each. The 5-nitro isomer was sublimed as a bright yellow powder and discarded. The 3-nitro isomer which remained in the bottom of the sublimation apparatus was collected. A total of 121 gm were sublimed to provide 60.9 gm (75.5%) of the crude 3-nitro isomer. 58 gm of the crude 3-nitro isomer were slurried in 200 mL hot 95:5 ethanol:water. The mixture was cooled to room temperature and diluted with 200 mL of water. After two hours the precipitate was collected by filtration and rinsed several times with water. The solid was dried under vacuum at room temperature to provide 38 gm (65% based on 58 gm crude) 3-nitro-6-amino-2-picoline.

MS(m/e): 153 (M$^+$)

Calculated for $C_6H_7N_3O_2$: Theory: C, 47.05; H, 4.61; N, 27.44. Found: C, 47.08; H, 4.53; N, 27.53.

Separation of nitration isomers by recrystallization

A mixture of 20 gm of the nitration mixture and 800 mL toluene were heated at reflux for 15 minutes. The mixture was filtered at 95° C. and the mother liquors allowed to cool to room temperature. After 4 hours the crystalline solid was collected, washed with 100 mL toluene, and dried under reduced pressure at 50° C. for 16 hours to provide 13.7 gm (68%) 3-nitro-6-amino-2-picoline.

Preparation of 2-(2-dimethylaminoethen-1-yl)-5-nitro-6-(dimethylaminomethylimino)pyrrolo[3,2-b]-pyridine (VI)

A mixture of 60 gm (0.39 mole) 3-nitro-6-amino-2-picoline 260 mL dimethylformamide was treated with 260 ml (1.83 mole) 94% dimethylformamide dimethylacetal and the solution was heated at reflux for 48 hours. The reaction was concentrated under reduced pressure and the residual solid slurried with toluene. The toluene was evaporated under reduced pressure. This procedure was repeated 5 times. The final residue was slurried with 300 mL methyl tert-butyl ether and then filtered. This solid was washed 3 times with 300 mL methyl tert-butyl ether and the black solid was finally dried under reduced pressure to provide 90.6 gm (88%) of the desired compound.

MS(m/e): 263.1 (M$^+$)

Calculated for $C_{12}H_{17}N_5O_2$: Theory: C, 54.74; H, 6.51; N, 26.60. Found: C, 54.84; H, 6.49; N, 26.79.

Hydrogenation

A mixture of 90 gm (0.34 mole) Intermediate VI and 6 gm 10% palladium on carbon in 650 mL ethanol was hydrogenated at 50 p.s.i. for 45 hours. The reaction mixture was filtered and the was concentrated under reduced pressure.

The residual solid was slurried for 30 minutes with 70:30 methyl tert-butyl ether:ethyl acetate, filtered and rinsed with 3×300 mL 70:30 methyl tert-butyl ether:ethyl acetate. The solid was powdered and then slurried with 200 mL 70:30 methyl tert-butyl ether:ethyl acetate. The solid was filtered and dried under reduced pressure to provide 54.5 gm (85%) of the title compound as a yellow solid.

MS(m/e): 188.2 (M$^+$)

PREPARATION XIII

Alternate isolation of Intermediate VI

A solution of 38.8 gm (0.25 mole) 3-nitro-6-amino-2-picoline in 172 mL dimethylformamide was treated with 172 mL dimethylformamide dimethylacetal and the mixture was heated at about 97° C. for 42 hours. The reaction mixture was then cooled to room temperature and was diluted with 650 mL isopropanol. The reaction mixture was allowed to stand for 18 hours at room temperature and was then coo ed to 3°–5° C. with stirring for an additional 2 hours. The slurry was filtered, the solid washed 2×75 mL isopropanol, and dried under reduced pressure at 45° C. for 16 hours to provide 58.9 gm (88%) of Intermediate VI.

PREPARATION XIV

Synthesis of Intermediate VI from Mixture of Nitration Isomers

A mixture of 133 gm (0.86 mole) of a 2:1 mixture of 3-nitro:5-nitro-6-amino-2-picoline in 500 mL dimethylformamide was treated with 500 mL (3.5 mole) 94% dimethylformamide dimethylacetal and heated at reflux for 40 hours. After cooling to room temperature, the reaction mixture was divided in half and each half was poured into 10 L of water at 0° C. with vigorous stirring. After 10 minutes, the mixture was filtered and the solid was slurried/rinsed with 3×1 L of water. The solid was dried under vacuum at 65° C. for 2.5 days to provide 183 gm (81%) of the title compound as a red solid.

PREPARATION XV

1-hydroxy-5-(dimethylaminomethylimino)pyrrolo[3,2-b]pyridine dihydrochloride A mixture of 23.4 gm (89 mMol) Intermediate VI and 0.7 gm 10% palladium on carbon in 234 mL anhydrous methanol were treated with 140 mL 5.9N ethanolic hydrogen chloride. The resulting mixture was hydrogenated for 1.5 hours under an initial hydrogen pressure of 30 p.s.i. The reaction mixture was diluted with 585 mL ethanol and was stirred at room temperature for 1 hour at room temperature. The precipitate was filtered and rinsed with 50 mL ethanol. The solid was taken up in 1.1 L methanol, filtered, and then concentrated under reduced pressure. The residual solid was dried under reduced pressure to provide 20.5 gm (83%) of the desired compound (containing 5% 5-(dimethylaminomethylimino)pyrrolo-[3,2-b]pyridine) as a yellow solid.

PREPARATION XVI

5-chloropyrrolo[3,2-b]pyridine
6-hydroxy-3-nitro-2-picoline

A suspension of 3.0 gm (19.6 mMol) 6-amino-3-nitro-2-picoline in 50 mL water containing 3.5 mL concentrated sulfuric acid was heated to effect solution. The resultant solution was cooled to 0° C. and a solution of 2.0 gm (29.4 mMol) sodium nitrite in 10 mL water was added with vigorous stirring at a rate to maintain the reaction mixture ≦10° C. After 4 hours the reaction mixture was filtered. The solid was washed with water and dried under reduced pressure to provide 2.4 gm (80%) of the desired compound as a pale yellow solid.

MS(m/e): 153 (M$^+$)

6-chloro-3-nitro-2-picoline

A mixture of 2.42 gm (15.7 mMol) 6-hydroxy-3-nitro-2-picoline, 1.0 gm phosphorus pentachloride, and 0.5 mL phosphorus oxychloride was heated at 110° C. for 2.5 hours. The reaction mixture was cooled to room temperature and then an additional 0.5 gm of phosphorus pentachloride and 0.5 mL phosphorus oxychloride were added. Heating was resumed for one hour at which point the reaction mixture poured into 100 mL of an ice/water slurry. The resultant slurry is filtered and the solid dried under vacuum to provide 2.3 gm (85%) of the desired compound as a brown solid.

2-(2-dimethylaminoethen-1-yl)-3-nitro-6-chloropyridine

A solution of 5 gm (29 mMol) 6-chloro-3-nitro-2-picoline in 40 mL dimethylformamide was treated with 5.83 mL (44 mMol) dimethylformamide dimethylacetal and the resulting mixture heated at 100° C. for 1.5 hours. At this point, 2 drops of triethylamine followed by 1.9 mL dimethylformamide dimethylacetal were added and heating continued for 2 more hours. The reaction mixture was concentrated under reduced pressure to provide the desired compound.

Reduction/ring closure

A mixture of 3.07 gm (13.5 mMol) 2-(2-dimethylamino-ethen-l-yl)-3-nitro-6-chloropyridine, 6.5 gm (.116 mole) iron and 16.4 gm silica gel in 170 mL 5:3 toluene:acetic acid was heated at 110° C. for 1 hour. The reaction mixture was filtered through a pad of celite. The filtrate was washed sequentially with aqueous sodium bisulfite, saturated aqueous sodium bicarbonate until the aqueous wash remains basic, and saturated aqueous sodium chloride. The remaining organics were dried over sodium sulfate and concentrated under reduced pressure. The residual solid was subjected to silica gel chromatography, eluting with dichloromethane containing from 0–5% methanol. Fractions containing product were combined and concentrated under reduced pressure to provide the title compound.

MS(m/e): 153 (M$^+$)

PREPARATION XVII

5-methoxypyrrolo[3,2-b]pyridine
6-methoxy-3-nitro-2-picoline 0.46 gm (20 mMol) sodium were dissolved in 15 mL anhydrous methanol. To this solution were added 2.3 gm 6-chloro-3-nitro-2-picoline in portions. The resulting mixture was stirred for 18 hours at room temperature and then 1 hour at reflux. The reaction mixture was poured into 100 mL of ice water with vigorous stirring. The suspension was filtered and the solid dried at 30° C. under reduced pressure for 18 hours to provide 2.04 gm (91%) of the desired compound as a tan solid.

2-(2-dimethylaminoethen-2-yl)-3-nitro-6-methoxypyridine

A mixture of 2.0 gm (11.9 mMol) 6-methoxy-3-nitro-2-picoline and 16 mL (119 mMol) dimethylformamide dimethylacetal in 20 mL dimethylformamide was heated at 100° C. for 7 hours. The reaction mixture was concentrated under reduced pressure. The residue was treated with toluene and concentrated under reduced pressure. The residual solid was dried at 50° C. under reduced pressure for 1 hour to provide 2.70 gm (100%) of the desired compound as a red solid.

Reduction/ring closure

A mixture of 2.5 gm (11.2 mMol) 2-(2-dimethylamino-ethen-2-yl)-3-nitro-6-methoxypyridine and 0.30 gm 10% palladium on carbon was hydrogenated at room temperature for 18 hours at an initial hydrogen pressure of 30 p.s.i. The reaction mixture was filtered and the filtrate concentrated under reduced pressure. The residue was subjected to silica gel chromatography, eluting with dichloromethane. Fractions containing product were combined and concentrated under reduced pressure to provide 1.22 gm (74%) of the title compound as a colorless solid.

m.p.=171°–174° C. (dec.)

MS(m/e): 364(M+1)

Calculated for $C_{14}H_{16}N_3O_3SF_3$-0.25 $H_2O$: Theory: C, 45.73; H, 4.52; N, 11.42. Found: C, 45.63; H, 4.45; N, 11.20.

EXAMPLE 1

3-(Octahydroindolizin-7-yl)-5-amino-1H-indole

The 3-(1,2,3,4,5,8-hexahydroindolizin-7-yl)-5-nitro-1H-indole (2.21 g, 6.90 mmol) was dissolved in 95 ml of ethanol and 50 ml of tetrahydrofuran. 5% palladium over carbon was added (550 mg) and the mixture was placed under an atmosphere of hydrogen, at an initial pressure of 60 psi, at room temperature, for 24 hours. The reaction mixture was filtered and the filtrate concentrated under reduced pressure to give 1.51 g of a purple foam. (85%).

EXAMPLE 2

3-(1,2,3,4,5,8-Hexahydroindolizin-7-yl)-1H-indole

Potassium hydroxide (10% in methanol, 15 ml, 26.8 mmol), 1H-indole (1.5 g, 13 mmol), and 7-indolizinone (1.39 g, 10 mmol) were combined and heated to reflux for 15 hours. The mixture was diluted with water and the precipitate was filtered. The brown filter cake was triturated with hot methanol, cooled to room temperature, and the solid collected to give 1.99 g of desired product. (84%).

Calculated for $C_{16}H_{18}N_2$: Theory: C, 80.63; H, 7.61; N, 11.75. Found: C, 80.81; H, 7.74; N, 11.92.

MS(FD) (m/e): 238.

EXAMPLE 3

3-(1,2,3,4,5,8-Hexahydroindolizin-7-yl)-5-fluoro-1H-indole

The 5-fluoro-1H-indole (910 mg, 6.7 mmol) and 7-indolizinone (1.40 g, 10.1 mmol) were converted to product by the procedure of Example 2 to give 1.22 g. (70.9%).

Calculated for $C_{16}H_{17}N_2F$: Theory: C, 74.97; H, 6.69; N, 10.93. Found: C, 74.78; H, 6.90; N, 11.05.

MS(FD) (m/e): 256

EXAMPLE 4

3-(1,2,3,4,5,8-Hexahydroindolizin-7-yl)-5-chloro-1H-indole

The 5-chloro-1H-indole (1.00 g, 6.63 mmol) and 7-indolizinone (1.39 g, 9.95 mmol) were converted to product by the procedure of Example 2 to give 595 mg. (33.1%).

Calculated for $C_{16}H_{17}N_2Cl$: Theory: C, 70.45; H, 6.28; N, 10.27. Found: C, 70.60; H, 6.46; N, 10.28.

MS(FD) (m/e): 272.

EXAMPLE 5

3-(1,2,3,4,5,8-Hexahydroindolizin-7-yl)-5-carboxamido-1H-indole

The 5-carboxamido-1H-indole (1.27 g, 7.95 mmol) and 7-indolizinone (1.44 g, 10.3 mmol) were converted to product by the procedure of Example 2 to give 1.80 g. (80%).

Calculated for $C_{17}H_{19}N_3O$: Theory: C, 72.57; H, 6.81; N, 14.93. Found: C, 72.48; H, 6.72; N, 14.91.

MS(FD) (m/e): 281.

EXAMPLE 6

N-(4-fluorobenzoyl)-3-(1,2,3,4,5,8-hexahydroindolizin-7-yl)-5-amino-1H-indole

The N-(4-fluorobenzoyl)-5-amino-1H-indole (813 mg, 3.20 mmol) and the 7-indolizinone (560 mg, 4.00 mmol) were converted to product by the procedure of Example 2 to give 818 mg. (68%).

Calculated for $C_{23}H_{22}N_3OF$: Theory: C, 73.58; H, 5.91; N, 11.19. Found: C, 73.84; H, 5.90; N, 11.26.

MS(FD) (m/e): 375.

EXAMPLE 7

N-(4-fluorobenzoyl)-3-(1,2,3,4,5,8-heptahydroquinolizin-7-yl)-5-amino-1H-indole

The N-(4-fluorobenzoyl)-5-amino-1H-indole (144 mg, 0.57 mmol) and the 2-octahydro-2H-quinolizinone (87 mg, 0.57 mmol) were converted to product by the procedure of Example 2 to give 60 mg. (27%).

MS(FD) (m/e) : 389.

EXAMPLE 8

N-(methanesulfonyl)-3-(1,2,3,4,5,8-hexahydroindolizin-7-yl)-5-amino-1H-indole

The N-(methanesulfonyl)-5-amino-1H-indole (1.06 g, 5.00 mmol) and the 7-indolizinone (900 mg, 6.50 mmol) were converted to product by the procedure of Example 2 to give 807 mg. (48.7%).

Calculated for $C_{17}H_{21}N_3O_2S$: Theory: C, 61.61; H, 6.39; N, 12.68. Found: C, 61.72; H, 6.38; N, 12.56.

MS(FD)(m/e): 331.

EXAMPLE 9

3-(Octahydroindolizin-7-yl)-5-hydroxy-1H-indole

The 3-(1,2,3,4,5,8-hexahydroindolizin-7-yl)-5-hydroxybenzyl-1H-indole hydrochloride salt (560 g, 1.47 mmol) was dissolved in 90 ml of ethanol and 5 ml of water and hydrogenated at an initial pressure of 60 psi, at room temperature, over 28 hours, using 5% palladium over carbon (280 mg). This mixture was filtered and the filtrate concentrated to give a white solid. The residue was taken up in water, made basic with aqueous sodium hydroxide, and extracted with methylene chloride. An attempt was made to dry the solution with sodium sulfate but upon addition of the sodium sulfate, the product came out of solution. Methanol was added to the mixture and the mixture filtered and the filtrate concentrated. The residue was recrystallized from methanol/methylene chloride to give 84 mg of product. (22%).

MS(FD) (m/e): 256.

MP=250–253 (dec).

EXAMPLE 10

3-(Octahydroindolizin-7-yl)-5-fluoro-1H-indole

The 3-(1,2,3,4,5,8-hexahydroindolizin-7-yl)-5-fluoro-1H-indole hydrochloride salt (450 mg, 1.53 mmol) was converted to product by the procedure of Example 9 to give 807 mg. (24%).

Calculated for $C_{16}H_{19}N_2F$: Theory: C, 74.39; H, 7.41; N, 10.84. Found: C, 74.76; H, 7.69; N, 10.84.

MS(FD)(m/e): 258.

EXAMPLE 11

Alternate Synthesis of 3-(octahydroindolizin-7-yl)-5-fluoro-1H-indole

The 3-(1,2,3,4,5,8-hexahydroindolizin-7-yl)-5-fluoro-1H-indole hydrochloride salt (450 mg, 1.54 mmol) was dissolved in trifluoroacetic acid (7.5 ml) forming an orange solution. The triethylsilane (197 mg, 1.7 mmol) was added and the reaction became colorless. TLC after 5 minutes showed no starting material present. The reaction was concentrated and the resulting oil poured into water and extracted with methylene chloride. The extract was washed with base, dried over sodium sulfate, and concentrated to give the product as a colorless oil.

EXAMPLE 12

N-(methanesulfonyl)-3-(octahydroindolizin-7-yl)-5-amino-1H-indole

The methanesulfonyl chloride (215 mg, 1.87 mmol) was added dropwise to a solution of the 3-(octahydroindolizin-7-yl)-5-amino-1H-indole (320 mg, 1.25 mmol) and triethylamine (0.5 ml) in 10 ml of dimethylformamide. The reaction was stirred at room temperature for 2.5 hours. The reaction was diluted with methanol and concentrated to give a dark semi-solid. This material was dissolved in a mixture of methylene chloride and water, made basic with an ammonium hydroxide solution, then extracted with methylene chloride. The extract was dried over sodium sulfate and concentrated to give a reddish brown oil. The material was purified on a flash column using silica gel (20% methanol in methylene chloride (ammonium hydroxide) as eluent) to give 210 mg of product. (49.7%).

MS(FD)(m/e): 333.

EXAMPLE 13

Alternate Synthesis of N-(methanesulfonyl)-3-(octahydro-indolizin-7-yl)-5-amino-1H-indole The N-(methanesulfonyl)-3-(1,2,3,4,5,8-hexahydro-indolizin-7-yl)-5-amino-1H-indole was converted to product by the procedure of Example 11 to give 351 mg of the desired products. (100%).

EXAMPLE 14

N-methyl-N'-(3-(octahydroindolizin-7-yl)-1H-indol-5-yl)urea

The methylisocyanate (220 mg, 3.9 mmol) was added to a solution of 3-(octahydroindolizin-7-yl)-5-amino-1H-indole (500 mg, 1.95 mmol) in 10 ml of dimethylformamide. The reaction was allowed to stir for 72 hours. TLC indicated the reaction was complete so the reaction was concentrated to give a purple gum. This material was chromatographed on a short FLORISIL™ column using 20% methanol in methylene chloride (ammonium hydroxide) as solvent to give 340 mg of a white foam. The white foam was recrystallized from methanol/ethyl acetate to give 165 mg of product. (27.1%).

MS(FD+)(m/e): 313.

EXAMPLE 15

Alternate Synthesis of N-methyl-N'-(3-(octahydroindolizin-7-yl)-1H-indol-5-yl)urea The trimethylsilyl isocyanate (288 mg, 2.50 mmol) was added to a solution of 3-(octahydroindolizin-7-yl)-5-amino-1H-indole (322 mg, 1.26 mmol) in 5 ml of dimethylformamide. The reaction was stirred at room temperature for 24 hours. TLC indicated consumption of starting material so the reaction was concentrated to give a purple foam which solidified. This material was chromatographed on a FLUORISIL™ column using 20% methanol in methylene chloride (ammonium hydroxide) as solvent to give 164 mg of product. (43.7%).

MS(FD)(m/e): 298.

EXAMPLE 16

N-(4-fluorobenzoyl)-3-(1,2,3,4,5,8-hexahydroindolizin-7-yl)-5-amino-benzothiophene A solution of 1.55 mL n-butyllithium in diethyl ether is cooled to −78° C. under a nitrogen atmosphere. To this cooled solution is added a solution of N-(4-fluorobenzoyl)-3-bromo-5-aminobenzothiophene (0.90 eq.) in diethyl ether. The reaction mixture is stirred at −78° C. for 1 hour and then to it is added dropwise a solution of 7-indolizinone (1.08 eq.) in diethyl ether. The reaction is stirred an additional 2 hours at −78° C. and is then gradually warmed to −20° C. over 55 minutes. The reaction mixture is then quenched with saturated aqueous sodium bicarbonate, diluted with additional diethyl ether and the phases separated. The organic phase is washed with saturated aqueous sodium chloride, dried over sodium sulfate and concentrated under reduced pressure. The residue is taken up in aqueous potassium hydroxide (10% in water) and heated to reflux for 15 hours. The mixture is concentrated in vacuo and the residue is subjected to flash silica gel chromatography. Fractions shown to contain product are combined and then concentrated under reduced pressure to give the title compound.

EXAMPLE 17

N-(4-fluorobenzoyl)-3-(1,2,3,4,5,8-hexahydroindolizin-7-yl)-5-amino-benzofuran

The title compound is obtained from N-(4-fluorobenzoyl)-3- bromo-5-amino-benzofuran and 7-indolizinone by the procedure of Example 16.

EXAMPLE 18

5-amino-3-(1,2,3,4,5,8-hexahydroindolizin-7-yl) pyrrolo[3,2-b]pyridine

To a solution of 0.185 gm (7.98 mMol) sodium in 8 mL methanol were added 0.50 gm (2.66 mMol) 5-(dimethylaminomethanimino)pyrrolo[3,2-b]pyridine followed by a solution of 0.55 gm (3.98 mMol) 1,2,3,4,5,6,8-heptahydroindolizin-7-one in 2 mL methanol. The resulting solution was heated at 75° C. for 18 hours. The reaction mixture was then cooled to room temperature and concentrated under reduced pressure. The residue was dissolved in chloroform and washed sequentially with water and saturated aqueous sodium chloride. The remaining organics were dried over sodium sulfate and concentrated under reduced pressure. The resulting brown residue was dissolved in 1:1 tetrahydrofuran:1N sodium hydroxide and the solution was heated at reflux for about 3 hours. The residue was concentrated under reduced pressure and the residue partitioned between water and 3:1 chloroform:isopropanol. The phases were separated and the organic phase washed well with saturated aqueous sodium chloride. The remaining organics were dried over sodium sulfate and concentrated under reduced pressure. The residue was subjected to flash silica gel chromatography, eluting with chloroform containing 10% methanol and 1% ammonium hydroxide. Fractions containing the desired product were combined and concentrated under reduced pressure to provide 0.348 gm (51%) of the title compound as an ivory solid.

MS(FD) (m/e): 253 ($M_+$)

Calculated for $C_{15}H_{18}N_4$: Theory: C, 70.84; H, 7.13; N, 22.03. Found: C, 70.84; H, 7.06; N, 21.84.

EXAMPLE 19

N-[4-fluorobenzoyl]-5-amino-3-(1,2,3,4,5,8-hexahydroindolizin-7-yl)pyrrolo[3,2-b]pyridine A mixture of 0.10 gm (0.39 mMol) 5-amino-3-(1,2,3,4,5,8-hexahydroindolizin-7-yl)pyrrolo[3,2-b]pyridine and 0.56 μL (0.47 mMol) 4-fluorobenzoyl chloride in 10 mL pyridine was stirred at 55° C. for 18 hours. The reaction mixture was then partitioned between 1N sodium hydroxide and 3:1 chloroform:isopropanol. The phases were separated and the organic phase washed with saturated aqueous sodium chloride, dried over magnesium sulfate, and concentrated under reduced pressure. The residue was subjected to radial chromatography (2 mm silica plate) eluting with dichloromethane containing 10% methanol and 1% ammonium hydroxide. Fractions containing product were combined and concentrated under reduced pressure to provide 0.077 gm (57%) of the title compound. The title compound was recrystallized twice from ethanol:water and dried under reduced pressure to provide a sample for analysis.

MS(FD) (m/e): 376 ($M_+$)

Calculated for $C_{22}H_{21}N_4FO$: Theory: C, 70.20; H, 5.62; N, 14.88. Found: C, 70.38; H, 5.78; N, 14.68.

EXAMPLE 20

N-[acetyl]-5-amino-3-(1,2,3,4,5,8-hexahydroindolizin-7-yl)pyrrolo[3,2-b]pyridine Beginning with 0.10 gm (0.39 mMol) 5-amino-3-(1,2,3,4,5,8-hexahydroindolizin-7-yl)pyrrolo[3,2-b]pyridine and 0.35 μL (0.47 mMol) acetyl chloride, 0.084 gm (73%) of the title compound were recovered by the procedure of Example 19.

MS(FD)(m/e): 296 ($M_+$)

The discovery that the $5\text{-HT}_{1F}$ receptor mediates neurogenic meningeal extravasation, thereby causing the pain associated with migraine and associated disorders, is disclosed in U.S. Pat. No. 5,521,196, herein incorporated by reference in its entirety. To demonstrate the use of the compounds of this invention in the treatment of migraine, their ability to bind to the $5\text{-HT}_{1F}$ receptor subtype was determined. The ability of the compounds of this invention to bind to the $5\text{-HT}_{1F}$ receptor subtype was measured essentially as described in N. Adham, et al., *Proceedings of the National Academy of Sciences (USA)*, 90, 408–412 (1993).

Membrane Preparation

Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200× g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200× g for 5 minutes at 4° C. to pellet large fragments which were discarded. The supernatant was collected and centrifuged at 40,000× g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding

[$^3$H-5-HT] binding was performed using slight modifications of the $5\text{-HT}_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 mL of buffer (50 mM Tris, 10 mM $MgCl_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (*Biochem. Pharmacol.*, 22, 3099–3108 (1973). All experiments were performed in triplicate. Representative compounds of this invention were found to have affinity for the $5\text{-HT}_{1F}$ receptor as measured by the procedure described supra.

As was reported by R. L. Weinshank, et al., W093/14201, the $5\text{-HT}_{1F}$ receptor is functionally coupled to a G-protein as measured by the ability of serotonin and serotonergic drugs to inhibit forskolin stimulated cAMP production in NIH3T3 cells transfected with the $5\text{-HT}_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the National Academy of Sciences* (USA), 89,3630–3634 (1992)), and the references cited therein.

Measurement of cAMP formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% $CO_2$. Drug dose-effect curves were then conducted by adding 6 different final concentrations of drug, followed immediately by the addition of forskolin (10 mM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500× g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention were tested and found to be agonists at the $5\text{-HT}_{1F}$ receptor in the cAMP assay.

Protein Extravasation

Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) are lowered through the holes in both hemispheres to a depth of 9 mm (rats) or 10.5 mm (guinea pigs) from dura.

The femoral vein is exposed and a dose of the test compound injected intravenously (1 mL/kg). Approximately 7 minutes later, a 50 mg/kg dose of Evans Blue, a fluorescent dye, is also injected intravenously. The Evans Blue complexes with proteins in the blood and functioned as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are killed and exsanguinated with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of Evans Blue dye in each sample. An excitation wavelength of approximately 535 nm is utilized and the emission intensity at 600 nm is determined. The microscope is equipped with a motorized stage and also interfaced with a personal computer. This facilitates the computer-controlled movement of the stage with fluorescence measurements at 25 points (500 µm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion is stimulated). This allows the other (unstimulated) half of the dura to be used as a control. The ratio of the amount of extravasation in the dura from the stimulated side compared to the unstimulated side dura is calculated. Saline controls yield a ratio of approximately 2.0 in rats and 1.8 in guinea pigs. In contrast, a compound which effectively prevents the extravasation in the dura from the stimulated side would have a ratio of approximately 1.0. A dose-response curve is generated and the dose that inhibited the extravasation by 50% ($ID_{50}$) is approximated.

Sumatriptan, a commercially available treatment for migraine, exhibits low bio-availability and relatively short duration of action. Its affinity for a number of serotonin receptor subtypes gives rise to undesirable side effects, particularly vasoconstriction, which severely limits its utility in the treatment of migraine. Since compounds of this invention are potent agonists of the $5\text{-HT}_{1F}$ receptor, extremely low doses are required to maintain therapeutic levels. Additionally, since compounds which are selective for the $5\text{-HT}_{1F}$ receptor relative to other receptors do not cause vasoconstriction, complications due to vasoconstriction are avoided. Compounds of this invention also inhibit protein extravasation if administered prior or subsequent to stimulation of the trigeminal ganglia, suggesting they may be administered prior to an incipient migraine attack to prevent pain, or during a migraine attack to alleviate pain.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, intranasal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 12 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 13 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Compound of Example 14 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Compound of Example 4 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Compound of Example 19 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Compound of Example 6 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Compound of Example 7 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Compound of Example 8 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Compound of Example 9 | 250.0 mg |
| Isotonic saline | 1000 ml |

Formulation Example 10

A topical formulation may be prepared as follows:

| Ingredient | Quantity |
|---|---|
| Compound of Example 10 | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
|---|---|
| Compound of Example 20 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°14 55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:
1. A compound of Formula I:

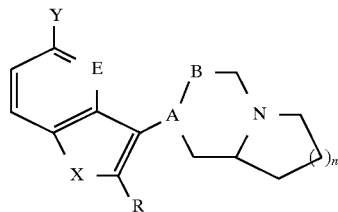

in which
A—B is —CH—CH$_2$— or —C=CH—;
n is 1, 2, or 3;
R is hydrogen or C$_1$-C$_4$ alkyl;
X is N—H, O or S;
Y is hydrogen, hydroxy, amino, halo, —S—R$^1$, —C(O)R$^2$, —C(O)NR$^3$R$^4$, —NR$^5$SO$_2$R$^6$, —NHC(Q)NR$^7$R$^8$, —NHC(O)OR$^9$, or —NR$^5$C(O)R$^{10}$;
wherein:
Q is O or S;
R$^1$ is phenyl, substituted phenyl, phenyl(C$_1$-C$_4$ alkylene), phenyl(C$_1$-C$_4$ alkylene) substituted in the phenyl ring, or pyridinyl;
R$^2$ is C$_1$-C$_6$ alkyl, phenyl(C$_1$-C$_4$ alkylene), phenyl(C$_1$-C$_4$ alkylene) substituted in the phenyl ring, naphthyl, amino, N-methyl-N-methoxyamino, heteroaryl, substituted heteroaryl, heteroaryl(C$_1$-C$_4$ alkyl), or substituted heteroaryl(C$_1$-C$_4$ alkyl);
R$^3$ is hydrogen, C$_1$-C$_6$ alkyl, heteroaryl, substituted heteroaryl, heteroaryl(C$_1$-C$_4$ alkyl), or substituted heteroaryl(C$_1$-C$_4$ alkyl);
R$^4$ is hydrogen or C$_1$-C$_6$ alkyl; or
R$^3$ and R$^4$ taken together with the nitrogen atom, to which they are attached, form a pyrrolidine, piperidine, substituted piperidine, piperazine, 4-substituted piperazine, morpholine or thiomorpholine ring;
R$^5$ is hydrogen or C$_1$-C$_4$ alkyl;
R$^6$ is C$_1$-C$_4$ alkyl, phenyl, substituted phenyl, or di(C$_1$-C$_4$ alkyl)amino;
R$^7$ and R$^8$ are independently selected from the group consisting of C$_1$-C$_6$ alkyl, C$_3$-C$_6$ alkenyl, C$_3$-C$_8$ cycloalkyl, phenyl, substituted phenyl, phenyl(C$_1$-C$_4$ alkylene), phenyl(C$_1$-C$_4$ alkylene) substituted in the phenyl ring, ((C$_1$-C$_4$ alkyl or C$_1$-C$_4$ alkoxycarbonyl substituted)C$_1$-C$_4$ alkyl)phenyl, C$_1$-C$_4$ alkyl a-substituted with C$_1$-C$_4$ alkoxycarbonyl; or
R$^7$ and R$^8$ taken together with the nitrogen atom form a pyrrolidine, piperidine, piperazine, 4-substituted piperazine, morpholine or thiomorpholine ring;
R$^9$ is C$_1$-C$_6$ alkyl, C$_3$-C$_6$ alkenyl, phenyl, substituted phenyl, C$_3$-C$_8$ cycloalkyl, C$_1$-C$_4$ alkyl w-substituted with C$_1$-C$_4$ alkoxy;
R$^{10}$ is C$_1$-C$_{10}$ alkyl optionally substituted with up to three substituents selected from the group consisting of hydroxy, C$_1$-C$_4$ alkoxy, halo, aryloxy, C$_1$-C$_4$ alkoxycarbonyl and heteroaryloxy, C$_2$-C$_{10}$ alkenyl, C$_2$-C$_{10}$ alkynyl, C$_3$-C$_8$ cycloalkyl, phenyl, substituted phenyl, naphthyl, phenyl(C$_1$-C$_4$ alkylene), phenyl(C$_1$-C$_4$ alkylene) substituted on the phenyl ring, 2-phenylethylen-1-yl, diphenylmethyl, benzofused C$_4$-C$_8$ cycloalkyl, C$_1$-C$_4$ alkylene w-substituted with C$_3$-C$_6$ cycloalkyl, or a heterocycle;
E is —CH— or N provided that E may not be N when X is O or S; or pharmaceutically acceptable acid addition salts and solvates thereof.
2. A compound of claim 1, in which A—B is —C=CH—.
3. A compound of claim 1, in which A—B is —CH—CH$_2$—.
4. A compound of claim 1, where X is N—H.
5. A compound of claim 1, where n is 1.
6. A compound of claim 1, where Y is —NR$^5$C(O)R$^{10}$.
7. A pharmaceutical formulation which comprises, in association with a pharmaceutically acceptable carrier, diluent, or excipient, a compound of Formula I:

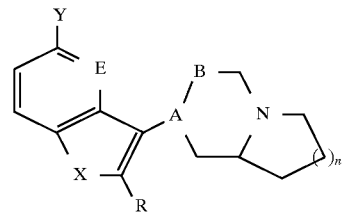

in which
A—B is —CH—CH$_2$— or —C=CH—;
n is 1, 2, or 3;
R is hydrogen or C$_1$-C$_4$ alkyl;
X is N—H, O, or S;
Y is hydrogen, hydroxy, amino, halo, —S—R$^1$, —C(O)R$^2$, —C(O)NR$^3$R$^4$, —NR$^5$SO$_2$R$^6$, —NHC(Q)NR$^7$R$^8$, —NHC(O)OR$^9$, or —NR$^5$C(O)R$^{10}$;
wherein:
Q is O or S;
R$^1$ is phenyl, substituted phenyl, phenyl(C$_1$-C$_4$ alkylene), phenyl(C$_1$-C$_4$ alkylene) substituted in the phenyl ring, or pyridinyl;
R$^2$ is C$_1$-C$_6$ alkyl, phenyl(C$_1$-C$_4$ alkylene), phenyl(C$_1$-C$_4$ alkylene) substituted in the phenyl ring, naphthyl, amino, N-methyl-N-methoxyamino, heteroaryl, substituted heteroaryl, heteroaryl(C$_1$-C$_4$ alkyl), or substituted heteroaryl(C$_1$-C$_4$ alkyl);
R$^3$ is hydrogen, C$_1$-C$_6$ alkyl, heteroaryl, substituted heteroaryl, heteroaryl(C$_1$-C$_4$ alkyl), or substituted heteroaryl(C$_1$-C$_4$ alkyl);
R$^4$ is hydrogen or C$_1$-C$_6$ alkyl; or
R$^3$ and R$^4$ taken together with the nitrogen atom, to which they are attached, form a pyrrolidine, piperidine, substituted piperidine, piperazine, 4-substituted piperazine, morpholine or thiomorpholine ring;
R$^5$ is hydrogen or C$_1$-C$_4$ alkyl;
R$^6$ is C$_1$-C$_4$ alkyl, phenyl, substituted phenyl, or di(C$_1$-C$_4$ alkyl)amino;
R$^7$ and R$^8$ are independently selected from the group consisting of C$_1$-C$_6$ alkyl, C$_3$-C$_6$ alkenyl, C$_3$-C$_8$ cycloalkyl, phenyl, substituted phenyl, phenyl(C$_1$-C$_4$ alkylene), phenyl(C$_1$-C$_4$ alkylene) substituted in the phenyl ring, ((C$_1$-C$_4$ alkyl or C$_1$-C$_4$ alkoxycarbonyl substituted)C$_1$-C$_4$ alkyl)phenyl, C$_1$-C$_4$ alkyl a-substituted with C$_1$-C$_4$ alkoxycarbonyl; or
R$^7$ and R$^8$ taken together with the nitrogen atom form a pyrrolidine, piperidine, piperazine, 4-substituted piperazine, morpholine or thiomorpholine ring;
R$^9$ is C$_1$-C$_6$ alkyl, C$_3$-C$_6$ alkenyl, phenyl, substituted phenyl, C$_3$-C$_8$ cycloalkyl, C$_1$-C$_4$ alkyl w-substituted with C$_1$-C$_4$ alkoxy;
R$^{10}$ is C$_1$-C$_{10}$ alkyl optionally substituted with up to three substituents selected from the group consisting of hydroxy, $C_1$–$C_4$ alkoxy, halo, aryloxy, $C_1$–$C_4$ alkoxycarbonyl and heteroaryloxy, $C_2$–$C_{10}$ alkenyl, $C_2$–$C_{10}$ alkynyl, $C_3$–$C_8$ cycloalkyl, phenyl, substituted phenyl, naphthyl, phenyl($C_1$–$C_4$ alkylene), phenyl($C_1$–$C_4$ alkylene) substituted on the phenyl ring, 2-phenylethylen-1-yl, diphenylmethyl, benzofused $C_4$–$C_8$ cycloalkyl, $C_1$–$C_4$ alkylene w-substituted with $C_3$–$C_6$ cycloalkyl, or a heterocycle;

E is —CH— or N provided that E may not be N when X is O or S; or pharmaceutically acceptable acid addition salts and solvates thereof.

8. A method for the activation of 5-$HT_{1F}$ receptors in mammals, comprising administering to a mammal in need of such activation, an effective amount of a compound of Formula I:

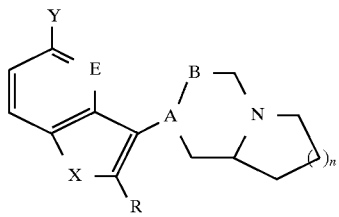

I in which

A—B is —CH—$CH_2$— or —C=CH—;

n is 1, 2, or 3;

R is hydrogen or $C_1$–$C_4$ alkyl;

X is N—H, O, or S;

Y is hydrogen, hydroxy, amino, halo, —S—$R^1$, —C(O)$R^2$, —C(O)$NR^3R^4$, —$NR^5SO_2R^6$, —NHC(Q)$NR^7R^8$, —NHC(O)$OR^9$, or —$NR^5$C(O)$R^{10}$;

wherein:

Q is O or S;

$R^1$ is phenyl, substituted phenyl, phenyl($C_1$–$C_4$ alkylene), phenyl($C_1$–$C_4$ alkylene) substituted in the phenyl ring, or pyridinyl;

$R^2$ is $C_1$–$C_6$ alkyl, phenyl($C_1$–$C_4$ alkylene), phenyl ($C_1$–$C_4$ alkylene) substituted in the phenyl ring, naphthyl, amino, N-methyl-N-methoxyamino, heteroaryl, substituted heteroaryl, heteroaryl($C_1$–$C_4$ alkyl), or substituted heteroaryl($C_1$–$C_4$ alkyl);

$R^3$ is hydrogen, $C_1$–$C_6$ alkyl, heteroaryl, substituted heteroaryl, heteroaryl($C_1$–$C_4$ alkyl), or substituted heteroaryl($C_1$–$C_4$ alkyl);

$R^4$ is hydrogen or $C_1$–$C_6$ alkyl; or $R^3$ and $R^4$ taken together with the nitrogen atom, to which they are attached, form a pyrrolidine, piperidine, substituted piperidine, piperazine, 4-substituted piperazine, morpholine or thiomorpholine ring;

$R^5$ is hydrogen or $C_1$–$C_4$ alkyl;

$R^6$ is $C_1$–$C_4$ alkyl, phenyl, substituted phenyl, or di($C_1$–$C_4$ alkyl)amino;

$R^7$ and $R_8$ are independently selected from the group consisting of $C_1$–$C_6$ alkyl, $C_3$–$C_6$ alkenyl, $C_3$–$C_8$ cycloalkyl, phenyl, substituted phenyl, phenyl($C_1$–$C_4$ alkylene), phenyl($C_1$–$C_4$ alkylene) substituted in the phenyl ring, (($C_1$–$C_4$ alkyl or $C_1$–$C_4$ alkoxycarbonyl substituted)$C_1$–$C_4$ alkyl)phenyl, $C_1$–$C_4$ alkyl a-substituted with $C_1$–$C_4$ alkoxycarbonyl; or $R^7$ and $R^8$ taken together with the nitrogen atom form a pyrrolidine, piperidine, piperazine, 4-substituted piperazine, morpholine or thiomorpholine ring;

$R^9$ is $C_1$–$C_6$ alkyl, $C_3$–$C_6$ alkenyl, phenyl, substituted phenyl, $C_3$–$C_8$ cycloalkyl, $C_1$–$C_4$ alkyl w-substituted with $C_1$–$C_4$ alkoxy;

$R^{10}$ is $C_1$–$C_{10}$ alkyl optionally substituted with up to three substituents selected from the group consisting of hydroxy, $C_1$–$C_4$ alkoxy, halo, aryloxy, $C_1$–$C_4$ alkoxycarbonyl and heteroaryloxy, $C_2$–$C_{10}$ alkenyl, $C_2$–$C_{10}$ alkynyl, $C_3$–$C_8$ cycloalkyl, phenyl, substituted phenyl, naphthyl, phenyl($C_1$–$C_4$ alkylene), phenyl($C_1$–$C_4$ alkylene) substituted on the phenyl ring, 2-phenylethylen-1-yl, diphenylmethyl, benzofused $C_4$–$C_8$ cycloalkyl, $C_1$–$C_4$ alkylene w-substituted with $C_3$–$C_6$ cycloalkyl, or a heterocycle;

E is —CH— or N provided that E may not be N when X is O or S; or pharmaceutically acceptable acid addition salts and solvates thereof.

9. A method for the inhibition of neuronal protein extravasation in mammals, comprising administering to a mammal in need of such inhibition, an effective amount of a compound of Formula I:

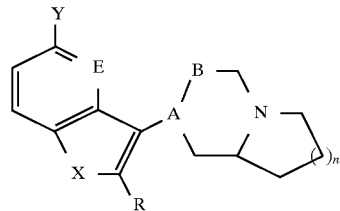

I in which

A—B is —CH—$CH_2$— or —C=CH—;

n is 1, 2, or 3;

R is hydrogen or $C_1$–$C_4$ alkyl;

X is N—H, O, or S;

Y is hydrogen, hydroxy, amino, halo, —S—$R^1$, —C(O)$R^2$, —C(O)$NR^3R^4$, —$NR^5SO_2R^6$, —NHC(Q)$NR^7R^8$, —NHC(O)$OR^9$, or —$NR^5$C(O)$R^{10}$;

wherein:

Q is O or S;

$R^1$ is phenyl, substituted phenyl, phenyl($C_1$–$C_4$ alkylene), phenyl($C_1$–$C_4$ alkylene) substituted in the phenyl ring, or pyridinyl;

$R^2$ is $C_1$–$C_6$ alkyl, phenyl($C_1$–$C_4$ alkylene), phenyl ($C_1$–$C_4$ alkylene) substituted in the phenyl ring, naphthyl, amino, N-methyl-N-methoxyamino, heteroaryl, substituted heteroaryl, heteroaryl($C_1$–$C_4$ alkyl), or substituted heteroaryl($C_1$–$C_4$ alkyl);

$R^3$ is hydrogen, $C_1$–$C_6$ alkyl, heteroaryl, substituted heteroaryl, heteroaryl($C_1$–$C_4$ alkyl), or substituted heteroaryl($C_1$–$C_4$ alkyl);

$R^4$ is hydrogen or $C_1$–$C_6$ alkyl; or $R^3$ and $R^4$ taken together with the nitrogen atom, to which they are attached, form a pyrrolidine, piperidine, substituted piperidine, piperazine, 4-substituted piperazine, morpholine or thiomorpholine ring;

$R^5$ is hydrogen or $C_1$–$C_4$ alkyl;

$R^6$ is $C_1$–$C_4$ alkyl, phenyl, substituted phenyl, or di($C_1$–$C_4$ alkyl)amino;

$R^7$ and $R^8$ are independently selected from the group consisting of $C_1$–$C_6$ alkyl, $C_3$–$C_6$ alkenyl, $C_3$–$C_8$ cycloalkyl, phenyl, substituted phenyl, phenyl($C_1$–$C_4$ alkylene), phenyl($C_1$–$C_4$ alkylene) substituted in the phenyl ring, (($C_1$–$C_4$ alkyl or $C_1$–$C_4$ alkoxycarbonyl substituted)$C_1$–$C_4$ alkyl)phenyl, $C_1$–$C_4$ alkyl a-substituted with $C_1$–$C_4$ alkoxycarbonyl; or $R^7$ and $R^8$ taken together with the nitrogen atom form a pyrrolidine, piperidine, piperazine, 4-substituted piperazine, morpholine or thiomorpholine ring;

$R^9$ is $C_1$–$C_6$ alkyl, $C_3$–$C_6$ alkenyl, phenyl, substituted phenyl, $C_3$–$C_8$ cycloalkyl, $C_1$–$C_4$ alkyl w-substituted with $C_1$–$C_4$ alkoxy;

$R^{10}$ is $C_1$–$C_{10}$ alkyl optionally substituted with up to three substituents selected from the group consisting of hydroxy, $C_1$–$C_4$ alkoxy, halo, aryloxy, $C_1$–$C_4$ alkoxycarbonyl and heteroaryloxy, $C_2$–$C_{10}$ alkenyl, $C_2$–$C_{10}$ alkynyl, $C_3$–$C_8$ cycloalkyl, phenyl, substituted phenyl, naphthyl, phenyl($C_1$–$C_4$ alkylene), phenyl($C_1$–$C_4$ alkylene) substituted on the phenyl ring, 2-phenylethylen-1-yl, diphenylmethyl, benzofused $C_4$–$C_8$ cycloalkyl, $C_1$–$C_4$ alkylene w-substituted with $C_3$–$C_6$ cycloalkyl, or a heterocycle;

E is —CH— or N provided that E may not be N when X is O or S; or pharmaceutically acceptable acid addition salts and solvates thereof.

\* \* \* \* \*